(12) United States Patent
Lou et al.

(10) Patent No.: US 11,768,205 B2
(45) Date of Patent: Sep. 26, 2023

(54) METHODS AND MATERIALS FOR IDENTIFYING AND TREATING CANCERS HAVING ELEVATED LEVELS OF PHOSPHORYLATED UBIQUITIN

(71) Applicant: Mayo Foundation for Medical Education and Research, Rochester, MN (US)

(72) Inventors: Zhenkun Lou, Rochester, MN (US); Min Deng, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 437 days.

(21) Appl. No.: 16/762,088

(22) PCT Filed: Nov. 6, 2018

(86) PCT No.: PCT/US2018/059309
§ 371 (c)(1),
(2) Date: May 6, 2020

(87) PCT Pub. No.: WO2019/090284
PCT Pub. Date: May 9, 2019

(65) Prior Publication Data
US 2021/0373023 A1    Dec. 2, 2021

Related U.S. Application Data

(60) Provisional application No. 62/636,615, filed on Feb. 28, 2018, provisional application No. 62/582,003, filed on Nov. 6, 2017.

(51) Int. Cl.
*G01N 33/574*    (2006.01)
*A61K 45/06*    (2006.01)

(52) U.S. Cl.
CPC ....... *G01N 33/57415* (2013.01); *A61K 45/06* (2013.01); *G01N 2333/47* (2013.01); *G01N 2440/14* (2013.01)

(58) Field of Classification Search
None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 8,053,183 B2 | 11/2011 | Nakamura et al. | |
| 9,804,174 B2 | 10/2017 | Matsuda et al. | |
| 2010/0152055 A1 | 6/2010 | Kozono et al. | |

FOREIGN PATENT DOCUMENTS

WO    WO 1991/011465    8/1991

OTHER PUBLICATIONS

Swaney et al (2015) (Phosphorylation of ubiquitin at Ser65 affects its polymerization, targets, and proteome-wide turnover, EMBO, 2015), (Year: 2015).*
Lacoursiere et al (Acetylation, Phosphorylation, Ubiquitination (Oh My!): Following Post-Translational Modifications on the Ubiquitin Road, Biomolecules, 2022) (Year: 2022).*
Swatek et al (2016) (Ubiquitin modifications, Cell Research, vol. 26, 2016), (Year: 2016).*
Hepowit et al (2021) (Regulation of ubiquitin and ubiquitin-like modifiers by phosphorylation, FebsJournal, 2021), (Year: 2021).*
Chen et al., "Nonproteolytic functions of ubiquitin in cell signaling," Mol. Cell, Feb. 13, 2009, 33(3):275-286.
Hershko et al., "The ubiquitin system," Annu. Rev. Biochemistry, 1998, 67:425-479.
Komander et al., "The ubiquitin code," Annu. Rev. Biochemistry, 2012, 81:203-229.
Randow et al., "Self and nonself: how autophagy targets mitochondria and bacteria," Cell Host Microbe, Apr. 9, 2014, 15(4):403-411.
Shaid et al., "Ubiquitination and selective autophagy," Cell Death Differentiation, Jun. 22, 2012, 20(1):21-30.
Assoian et al., "Coordinate signaling by integrins and receptor tyrosine kinases in the regulation of G1 phase cell-cycle progression," Curr. Opin. Genet. Development, Feb. 2001, 11(1):48-53.
Baines et al., "Purification of Immunoglobulin G (IgG)," Methods in Molecular Biology: Immunochemical Protocols, 1992, 10:79-104.
Barbas et al., "Combinatorial Immunoglobulin Libraries on the Surface of Phage (Phabs): Rapid Selection of Antigen-Specific Fabs," Methods, Apr. 1991, 2(2):119-124.
Blume-Jensen et al., "Oncogenic kinase signalling," Nature, May 2001, 411(6835):355-365.
Carpenter et al., "Epidermal growth factor stimulates phosphorylation in membrane preparations in vitro," Nature, Nov. 1978, 276(5686):409-410.
Carpenter, "Receptors for Epidermal Growth Factor and Other Polypeptide Mitogens," Ann. Rev. Biochemistry, Jul. 1987, 56(1):881-914.
Carter et al., "Humanization of an anti-p185HER2 antibody for human cancer therapy," Proc. Nat. Acad. Sci. USA, May 1992, 89(10):4285-4289.
Ciardiello et al., "EGFR Antagonists in Cancer Treatment," N. Engl. J. Medicine, Mar. 13, 2008, 358(11):1160-1174.
Current Protocols in Immunology, 1st ed., Coligan et al. (eds.), 1996, Chapter 2, 176 pages.

(Continued)

*Primary Examiner* — Laura B Goddard
*Assistant Examiner* — Sarah A Alsomairy
(74) *Attorney, Agent, or Firm* — Fish & Richardson P.C.

(57) ABSTRACT

This document provides methods and materials involved in identifying mammals (e.g., humans) having cancer cells with an elevated level of phosphorylated Ub polypeptides (e.g., an elevated level of Y59 phosphorylated Ub polypeptides). For example, methods and materials for detecting the presence of cancer cells having an elevated level of Y59 phosphorylated Ub polypeptides are provided.

14 Claims, 40 Drawing Sheets

Specification includes a Sequence Listing.

(56) References Cited

OTHER PUBLICATIONS

Current Protocols in Immunology, 1st ed., Coligan et al. (eds.), 1996, Chapter 9, 164 pages.

Dall'Acqua et al., "Antibody humanization by framework shuffling," Methods, May 2005, 36(1):43-60.

Damschroder et al., "Framework shuffling of antibodies to reduce immunogenicity and manipulate functional and biophysical properties." Mol. Immunology. Apr. 2007, 44(11):3049-3060.

Deng et al., "Deubiquitination and Activation of AMPK by USP10," Mol. Cell, Feb. 2016, 61(4):614-624.

Ettenberg et al., "Cbl-b-dependent Coordinated Degradation of the Epidermal Growth Factor Receptor Signaling Complex," J. Biol. Chemistry, Jul. 2001, 276(29):27677-27684.

Fonseca et al., "A Balance of Protein Synthesis and Proteasome-Dependent Degradation Determines the Maintenance of LTP," Neuron, Oct. 2006, 52(2):239-245.

Green et al., "Antigen-specific human monoclonal antibodies from mice engineered with human Ig heavy and light chain YACs," Nat. Genetics, May 1994, 7(1):13-21.

Griffiths et al., "Isolation of high affinity human antibodies directly from large synthetic repertoires," EMBO Journal, Jul. 1994, 13(14):3245-3260.

Gulve et al., "Regulation of protein synthesis and degradation in L8 myotubes. Effects of serum, insulin and insulin-like growth factors," Biochem. Journal, Jun. 1989, 260(2):377-387.

Hornbeck et al., "PhosphoSitePlus, 2014: mutations, PTMs and recalibrations," Nucleic Acids Research, Jan. 2015, 43(Database issue):D512-D520.

Huse et al., "Generation of a Large Combinatorial Library of the Immunoglobulin Repertoire in Phage Lambda," Science, Dec. 1989, 246(4935):1275-1281.

Hwang et al., "Use of human germline genes in a CDR homology-based approach to antibody humanization," Methods, May 2005, 36(1):35-42.

Jones et al., "Replacing the complementarity-determining regions in a human antibody with those from a mouse," Nature, May 1986, 321(6069):522-525.

Kashmiri et al., "SDR grafting—a new approach to antibody humanization," Methods, May 2005, 36(1):25-34.

Kimball et al., "Regulation of Protein Synthesis by Insulin," Annu. Rev. Physiology, 1994, 56:321-348.

Kirkpatrick et al., "Quantitative analysis of in vitro ubiquitinated cyclin B1 reveals complex chain topology," Nat. Cell Biology, Jul. 2006, 8(7):700-710.

Knappik et al., "Fully Synthetic Human Combinatorial Antibody Libraries (HuCAL) Based on Modular Consensus Frameworks and CDRs Randomized with Trinucleotides," J. Mol. Biology, Feb. 2000, 296(1):57-86.

Kohler et al., "Continuous cultures of fused cells secreting antibody of predefined specificity," Nature, Aug. 1975, 256(5517):495-497.

Lazar et al., "A molecular immunology approach to antibody humanization and functional optimization," Mol. Immunology, Mar. 2007, 44(8):1986-1998.

Lecker et al., "Protein Degradation by the Ubiquitin-Proteasome Pathway in Normal and Disease States," J. Am. Soc. Nephrology, Jul. 2006, 17(7):1807-1819.

Levkowitz et al., "Ubiquitin Ligase Activity and Tyrosine Phosphorylation Underlie Suppression of Growth Factor Signaling by c-Cbl/Sli-1," Mol. Cell, Dec. 1999, 4(6):1029-1040.

Li et al., "A ubiquitin ligase transfers preformed polyubiquitin chains from a conjugating enzyme to a substrate," Nature, Mar. 2007, 446(7133):333-337.

Lonberg et al., "Antigen-specific human antibodies from mice comprising four distinct genetic modifications," Nature, Apr. 1994, 368(6474):856-859.

Longva et al., "Ubiquitination and proteasomal activity is required for transport of the EGF receptor to inner membranes of multivesicular bodies," J. Cell Biology, Feb. 25, 2002, 156(5):843-854.

Losman et al., "Baboon Anti-idiotype Antibodies Mimic a Carcinoembryonic Antigen Epitope," Int. J. Cancer, Aug. 1990, 46(2):310-314.

MacLean et al., "Skyline: an open source document editor for creating and analyzing targeted proteomics experiments," Bioinfonnatics, Apr. 2010, 26(7):966-968.

Nathan et al., "Why do cellular proteins linked to K63-polyubiquitin chains not associate with proteasomes?" EMBO Journal, Feb. 2013, 32(4):552-565.

Nedelsky et al., "Autophagy and the ubiquitin-proteasome system: collaborators in neuroprotection," Biochim. Biophys. Acta., Dec. 2008, 1782(12):691-699.

Nisonhoff et al., "Separation of Univalent Fragments from the Bivalent Rabbit Antibody Molecule by Reduction of Disulfide Bonds," Arch. Biochem. Biophysics, Aug. 1960, 89:230-244.

Orlandi et al., "Cloning immunoglobulin variable domains for expression by the polymerase chain reaction," Proc. Nat. Acad. Sci. USA, May 1989, 86(10):3833-3837.

Pao et al., "Rational, biologically based treatment of EGFR-mutant non-small-cell lung cancer," Nat. Rev. Cancer, Nov. 2010, 10(11):760-774.

Pardee, "G1 Events and Regulation of Cell Proliferation," Science, Nov. 1989, 246(4930):603-608.

PCT International Preliminary Report on Patentability in International Application No. PCT/US2018/059309 dated May 12, 2020, 6 pages.

PCT International Search Report and Written Opinion in International Application No. PCT/US2018/059309 dated Feb. 27, 2019, 9 pages.

Polet et al., "Effects of epidermal growth factor on protein degradation, the translocation of non-histone proteins to the nucleus and DNA synthesis," Biochim. Biophys. Acta, Oct. 1989, 1013(3):279-286.

Porter, "The Hydrolysis of Rabbit γ-Globulin and Antibodies with Crystalline Papain," Biochem. Journal, Sep. 1959, 73(1):119-127.

Pray et al., "Cell cycle regulatory E3 ubiquitin ligases as anticancer targets," Drug Resist. Updates, Dec. 2002, 5(6):249-258.

Rader et al., "A phage display approach for rapid antibody humanization: Designed combinatorial V gene libraries," Proc. Nat. Acad. Sci. USA, Jul. 1998, 95(15):8910-8915.

Riechmann et al., "Reshaping human antibodies for therapy," Nature, Mar. 1988, 332(6162):323-327.

Rosok et al., "A Combinatorial Library Strategy for the Rapid Humanization of Anticarcinoma BR96 Fab," J. Biol. Chemistry, Sep. 1996, 271(37):22611-22618.

Sandhu et al., "Protein Engineering of Antibodies," Crit. Rev. Biotechnology, 1992, 12(5-6):437-462.

Schubert et al., "Structure of PINK in complex with its substrate ubiquitin," Nature, Dec. 2017, 552(7683):51-56.

Schweppe et al., "Quantitative phosphoproteomic profiling of human non-small cell lung cancer tumors," J. Proteomics, Oct. 2013, 91:286-296.

Sengupta et al., "Regulation of the mTOR Complex 1 Pathway by Nutrients, Growth Factors, and Stress," Mol. Cell, Oct. 2010, 40(2):310-322.

Shim et al., "c-Myc transactivation of LDH-A: Implications for tumor metabolism and growth," Proc. Nat. Acad. Sci. USA, Jun. 1997, 94(13):6658-6663.

Singer et al., "Optimal humanization of 1B4, an anti-CD18 murine monoclonal antibody, is achieved by correct choice of human V-region framework sequences," J. Immunology, Apr. 1993, 150(7):2844-2857.

Suraweera et al., "Failure of Amino Acid Homeostasis Causes Cell Death following Proteasome Inhibition," Mol. Cell, Oct. 2012, 48(2):242-253.

Swaney et al., "Phosphorylation of ubiquitin at Ser65 affects its polymerization, targets, and proteome-wide turnover," EMBO Reports, Sep. 2015, 16(9):1131-1144.

Taelman et al., "Wnt Signaling Requires Sequestration of Glycogen Synthase Kinase 3 inside Multivesicular Endosomes," Cell, Dec. 2010, 143(7):1136-1148.

(56) References Cited

OTHER PUBLICATIONS

Taylor et al., "Human immunoglobulin transgenes undergo rearrangement, somatic mutation and class switching in mice that lack endogenous IgM," Int. Immunology, Apr. 1994, 6(4):579-591.
Turla et al., "Mechanisms of Angiotensin II-and Arginine Vasopressin-Induced Increases in Protein Synthesis and Content in Cultured Rat Aortic Smooth Muscle Ceils: Evidence for Selective Increases in Smooth Muscle Isoactin Expression," Circ. Research, Jan. 1991, 68(1):288-299.
Verhoeyen et al., "Reshaping Human Antibodies: Grafting an Antilysozyme Activity," Science, Mar. 1988, 239(4847):1534-1536.
Villa et al., "Parkin-Independent Mitophagy Controls Chemotherapeutic Response in Cancer Cells," Cell Reports, Sep. 2017, 20(12):2846-2859.
Voorhees et al., "The Proteasome as a Target for Cancer Therapy," Clin. Cancer Research, Dec. 2003, 9(17):6316-6325.
Wei et al., "EGFR-Mediated Beclin 1 Phosphorylation in Autophagy Suppression, Tumor Progression, and Tumor Chemoresistance," Cell, Sep. 2013, 154(6):1269-1284.
Wieduwilt et al., "The epidermal growth factor receptor family: biology driving targeted therapeutics," Cell. Mol. Life Sciences, May 2008, 65(10):1566-1584.
Winter et al., "Making Antibodies bv Phage Display Technologv," Annu. Rev. Immunology, Apr. 1994, 12(1):433-455.
Xu et al., "A Ubiquitin Replacement Strategy in Human Cells Reveals Distinct Mechanisms of IKK Activation by TNFα and IL-1β," Mol. Cell, Oct. 2009, 36(2):302-314.
Zhao et al., "FoxO3 Coordinately Activates Protein Degradation by the Autophagic/Lysosomal and Proteasomal Pathways in Atrophying Muscle Cells," Cell Metabolism, Dec. 2007, 6:472-483.

\* cited by examiner

| Peptide Name | Peptide sequence | Light mass | Heavy mass | Light (m/z) | Heavy (m/z) | Fragment ions |
|---|---|---|---|---|---|---|
| 64-74 | ESTLHLVLR | 1066.61324 | 1,073.63 | 356.5449+++ | 358.8049+++ | y5, y4, y3, y2 |
| 43-54 K48(8) | LFAGK(GG)QLEDGR | 1459.77064 | 1,466.80 | 487.6008+++ | 489.9399+++ | y6, y5, y4, y3, y2 |
| 55-72 K63(88) | TLSDYNIQK(GG)ESTLHLVLR | 2243.19104 | 2,250.21 | 561.8055+++ | 563.5601+++ | y10, y9, y8, y5, y4, y3 |
| 7-27 K11(g) | TLTGK(GG)TITLEVEPSDTIEN(X)K | 2401.2592 | 2,407.37 | 601.4276+++ | 603.4322+++ | y11, y10, y9, y8, y7, y6 |
| 30-44 K39(gg) | IQDK(GG)EGIPPDQQR | 1836.9172 | 1,842.93 | 460.6101+++ | 461.6102+++ | y6, y5, y3 |
| 55-63 | TLSDYNIQK | 1080.54584 | 1,087.56 | 541.2808++ | 544.7094++ | y7, y5, y4, y3, y2 |
| 1-11 M1(gg) | MQIFVK(GG)TLTGK | 1378.76404 | 1,385.78 | 465.9370+++ | 468.2601+++ | y5, y4, y3, y2 |
| 12-29 K27(gg) | TITLEVEPSDTIENVK(GG)AK | 2100.0952 | 2,106.11 | 701.0396+++ | 703.0442+++ | 11, y7, y6, y5, y3 |
| 1-9 M1(g) | MQIFVK(g) | 878.46918 | 884.493 | 440.2403++ | 443.2394++ | y6, y5, y4, y3, y2 |
| 55-72 | TLSDYNIQKESTLHLVLR | 2129.14864 | 2,136.17 | 710.7243+++ | 713.0632+++ | y12, y11, y10, y9, y4 |
| 28-33 K29(gg) | AK(GG)IQDK | 815.450514 | 821.450 | 449.3200++ | 451.2250++ | y5, y4, y3, y2 |
| 55-63 pY59 | TLSDYNIQK | 1160.51184 | 1,167.53 | 581.2638++ | 584.7724++ | y7, y6, y5 |
| 55-72 | TLSDYNIQKESTLHLVLR | 2323.15784 | 2,330.18 | 775.3999+++ | 777.7332+++ | y9, y7, y6, y5, y4, y3 |
| 64-72(80) pY59 | | | | | | |
| 55-72 pY59 | TLSDYNIQKESTLHLVLR | 2209.11484 | 2,216.13 | 737.3795+++ | 739.7186+++ | y5, y7, y6, y5, y4, y3 |

A

B

C

D

E

F

E

F

G

H

I

C

D

E

F

F

G

H

E

F

A

B

C

D

E

SEQUENCE LISTING

```
<160> NUMBER OF SEQ ID NOS: 2

<210> SEQ ID NO 1
<211> LENGTH: 15
<212> TYPE: PRT
<213> ORGANISM: human
<220> FEATURE:
<221> NAME/KEY: MOD_RES
<222> LOCATION: (4)..(4)
<223> OTHER INFORMATION: PHOSPHORYLATION

<400> SEQUENCE: 1

Leu Ser Asp Tyr Asn Ile Gln Lys Glu Ser Thr Leu His Leu Cys
1               5                   10                  15

<210> SEQ ID NO 2
```

```
-continued

<211> LENGTH: 15
<212> TYPE: PRT
<213> ORGANISM: human

<400> SEQUENCE: 2

Leu Ser Asp Tyr Asn Ile Gln Lys Glu Ser Thr Leu His Leu Cys
1               5                   10                  15
```

METHODS AND MATERIALS FOR IDENTIFYING AND TREATING CANCERS HAVING ELEVATED LEVELS OF PHOSPHORYLATED UBIQUITIN

CROSS-REFERENCE TO RELATED APPLICATIONS

This application is a National Stage application under 35 U.S.C. § 371 of International Application No. PCT/US2018/059309, having an International Filing Date of Nov. 6, 2018, which claims priority to U.S. Application Serial Nos. 62/636,615, filed on Feb. 28, 2018 and 62/582,003, filed Nov. 6, 2017. The disclosure of the prior applications are considered part of the disclosure of this application, and are incorporated in their entirety into this application.

BACKGROUND

1. Technical Field

This document relates to methods and materials involved in identifying and treating mammals having cancer cells with an elevated level of phosphorylated ubiquitin (Ub) polypeptides (e.g., an elevated level of Y59 phosphorylated Ub polypeptides). For example, this document provides methods and materials for administering one or more tyrosine kinase inhibitors (e.g., epidermal growth factor receptor (EGFR) or fibroblast growth factor receptor (FGFR) inhibitors) and/or one or more proteasome inhibitors to mammals identified as having cancer cells with an elevated level of phosphorylated Ub polypeptides.

2. Background Information

Cells possess mechanisms to coordinate protein synthesis with degradation to maintain an adequate supply of amino acids and to maintain protein homeostasis, as even a small persistent imbalance between these processes can disrupt cell and tissue physiology (Suraweera et al., *Mol. Cell*, 48:242-253 (2012); and Fonseca et al., *Neuron*, 52:239-245 (2006)). Cell surface growth factor receptors couple environmental cues to promote anabolic processes, such as protein synthesis (Sengupta et al., *Mol. Cell*, 40:310-322 (2010); Turla et al., *Circ. Res.*, 68:288-299 (1991); Kimball et al., *Annu. Rev. Physiol.*, 56:321-348 (1994); Pardee et al., *Science*, 246:603-608 (1989); and Assoian et al., *Curr. Opin. Genet. Dev.*, 11:48-53 (2001)), and aberrant activation of such receptors is a common feature of human malignancies (Ciardiello et al., *N. Engl. J. Med.*, 358:1160-1174 (2008); and Blume-Jensen et al., *Nature*, 411:355-365 (2001)). EGFR, an oncogenic receptor tyrosine kinase, links extracellular signals to cellular homeostasis (Wieduwilt et al., *Cell. Mol. Life Sci.*, 65:1566-1584 (2008); and Carpenter et al., Nature, 276:409-410 (1978)).

SUMMARY

This document provides methods and materials involved in identifying mammals (e.g., humans) having cancer cells with an elevated level of phosphorylated Ub polypeptides (e.g., an elevated level of Y59 phosphorylated Ub polypeptides). For example, this document provides methods and materials for detecting the presence of cancer cells having an elevated level of Y59 phosphorylated Ub polypeptides. As described herein, mammals (e.g., humans) identified as having cancer cells (e.g., breast cancer cells) having an elevated level of phosphorylated Ub polypeptides (e.g., an elevated level of Y59 phosphorylated Ub polypeptides) can be treated with one or more tyrosine kinase inhibitors (e.g., EGFR or FGFR inhibitors) to reduce the number of cancer cells within that mammal. Identifying mammals having cancer cells with an elevated level of phosphorylated Ub polypeptides (e.g., an elevated level of Y59 phosphorylated Ub polypeptides) as described herein can allow clinicians to proceed with proper treatment options for cancer patients.

This document also provides methods and materials involved in treating mammals identified as having cancer cells with an elevated level of phosphorylated Ub polypeptides (e.g., an elevated level of Y59 phosphorylated Ub polypeptides). For example, this document provides methods and materials for administering one or more tyrosine kinase inhibitors (e.g., one or more EGFR and/or FGFR inhibitors) and/or one or more proteasome inhibitors to mammals identified as having cancer cells with an elevated level of phosphorylated Ub polypeptides (e.g., an elevated level of Y59 phosphorylated Ub polypeptides) to reduce the number of cancer cells within that mammal. As described herein, mammals having cancer cells with an elevated level of phosphorylated Ub polypeptides (e.g., an elevated level of Y59 phosphorylated Ub polypeptides) can be administered one or more tyrosine kinase inhibitors (e.g., one or more EGFR and/or FGFR inhibitors) to reduce the number of such cancer cells within that mammal, thereby treating that mammal's cancer. Having the ability to use one or more tyrosine kinase inhibitors (e.g., one or more EGFR and/or FGFR inhibitors) to reduce the number of cancer cells within a mammal identified as having cancer cells with an elevated level of phosphorylated Ub polypeptides (e.g., an elevated level of Y59 phosphorylated Ub polypeptides) can allow clinicians and patients to proceed with effective treatment options.

In addition, this document provides antibody preparations containing an antibody that has binding specificity for a Ub polypeptide epitope containing a phosphorylated Y59 residue and lacks binding specificity for the same Ub polypeptide epitope containing a Y59 residue that is not phosphorylated. For example, this document provides anti-pY59 Ub polypeptide antibodies such as rabbit anti-UbpY59. As described herein, anti-pY59 Ub polypeptide antibodies can be used to identify mammals having cancer cells with an elevated level of phosphorylated Ub polypeptides (e.g., an elevated level of Y59 phosphorylated Ub polypeptides). Having the ability to identify mammals having cancer cells with an elevated level of phosphorylated Ub polypeptides (e.g., an elevated level of Y59 phosphorylated Ub polypeptides) using an anti-pY59 Ub polypeptide antibody as described herein can allow clinicians to make effective assessments of cancer patients in a manner that allows them to proceed with proper treatment options.

In general, one aspect of this document features a method for identifying a mammal as having cancer cells comprising an elevated level of phosphorylated Ub polypeptides. The method comprises, or consists essentially of, (a) determining the presence or absence of the cancer cells within a sample obtained from the mammal, and (b) classifying the mammal as having the cancer cells if the presence is determined in the step (a). The mammal can be a human. The cancer cells can be breast cancer cells. The determining step (a) can comprise detecting the presence of the cancer cells. The determining step (a) can comprise detecting the absence of the cancer cells. The phosphorylated Ub polypeptides can be phosphorylated Y59 Ub polypeptides.

In another aspect, this document features a method for treating cancer. The method comprises, or consists essentially of, (a) identifying a mammal as having cancer cells comprising an elevated level of phosphorylated Ub polypeptides, and (b) administering a tyrosine kinase inhibitor to the mammal, thereby reducing the number of the cancer cells within the mammal. The mammal can be a human. The cancer can be breast cancer. The tyrosine kinase inhibitor can be Erlotinib, PD153035 HCl, PD168393, AZD3759, Cetuximab, AZD9291, Gefinitib, Panitumumab, ZD1839, Afatinib, Tyrphostin (AG-1478), Lapatinib, Rociletinib (CO-1686), Neratinib, Infigratinib (BGJ398), BLU9931, AZD4547, FGF401, Debio-1347, JNJ-42756493, TAS 120, FIIN-2, LY2874455, Derazantinib ARQ 087, BAY 1163877, Nintedanib, RO4383596 AZD2171 (cediranib), Dovitinib (TKI 258), Ponatinib, PD173074, Sorafenib, Sunitinib (SU11248), Vandetanib ZD6474, Pazopanib, or Brivanib. In some cases, the tyrosine kinase inhibitor can be an epidermal growth factor receptor (EGFR) inhibitor. The EGFR inhibitor can be PD153035 HCl, PD168393, Erlotinib, AZD3759, Cetuximab, AZD9291, Gefinitib, Panitumumab, ZD1839, Afatinib, Tyrphostin (AG-1478), Lapatinib, Rociletinib (CO-1686), and Neratinib. In some cases, the tyrosine kinase inhibitor can be a fibroblast growth factor receptor (FGFR) inhibitor. The FGFR inhibitor can be Infigratinib (BGJ398), BLU9931, AZD4547, FGF401, Debio-1347, JNJ-42756493, TAS 120, FIIN-2, LY2874455, Derazantinib ARQ 087, or BAY 1163877.

In another aspect, this document features an anti-phosphorylated Ub polypeptide antibody. The antibody can be an anti-phosphorylated Y59 Ub polypeptide antibody. The antibody can be a polyclonal antibody produced using SEQ ID NO:1.

In another aspect, this document features a composition comprising an anti-phosphorylated Ub polypeptide antibody. The antibody can be an anti-phosphorylated Y59 Ub polypeptide antibody. The antibody can be a polyclonal antibody produced using SEQ ID NO:1.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

and FIG. 9E (B). (C). WT Ub- and Ub Y59F-replacement cells were serum starved and DOX induced for 72 hours to replace endogenous Ub with Ub WT or Ub Y59F and then treated with 20 ng EGF for different times. K63-linked conjugates were determined by Western blot. (D and E) Ub WT- and Ub Y59F-replacement cells were treated as in FIG. 9F, except that 10 µM chloroquine (D) or 20 nM bortezomib (E) was present in the chase media. The rate of protein degradation was shown as the fraction of radiolabeled protein remaining over time. Data were mean±SD of three independent experiments. (**: p<0.01, by two-way ANOVA). (F). WT Ub- and Ub Y59F-replacement cells were serum starved and DOX induced for 72 hours to replace endogenous Ub with Ub WT or Ub Y59F and then treated with 20 ng EGF for different times. Cell lysates were harvested and blotted with anti-EGFR and anti-Actin antibodies. (G). WT Ub- and Ub Y59F-replacement cells were serum starved and DOX induced for 72 hours to replace endogenous Ub with Ub WT or Ub Y59F and then treated with 20 ng EGF and MG132 for 2 hours. Cells without DOX induction were used as negative control. Cell lysates were harvested and immunoprecipitated with anti-HA beads. Samples were run on SDS-PAGE gel and blotted with indicated antibodies. MG132 was included to equalize the expression level of HA-Ub and HA-Ub Y59F.

DETAILED DESCRIPTION

Figure 1:
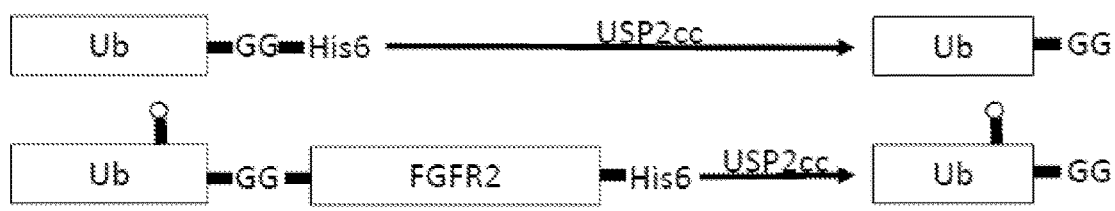
FIG. 1. Phosphorylation of Ub promotes Ub chain assembly. (A). Strategy of ubiquitin and phos-Ub production. Ub and Ub-FGFR2 were fused with a his6 at the c-terminal and transformed into Bl21, and protein expression was induced with IPTG. Cell lysates were then purified with Ni-NTA, and purified protein was cut with his-USP2cc to remove the C-terminal tag. The phosphorylation efficiency of ubiquitin was checked by phos-tag gel. (B). Purified ubiquitin and phos-ubiquitin were loaded on phos-tag gel (upper panel) or non phos-tag gel (lower panel). The proteins were blotted with anti-Ub and anti-pY59 antibodies. (C). The assembly of ubiquitin chains was determined at 30° C. in the presence of Ube1, Ube2g2, gp78, and indicated Ub variants. Samples were taken at the indicated time points, and polyubiquitin chains were detected by immunoblotting with an anti-Ub antibody. (D). The assembly of ubiquitin chains was determined at 30° C. in the presence of Ube1, Ube2D3, MDM2, and indicated Ub variants. Samples were taken at the indicated time points, and polyubiquitin chains were detected by immunoblotting with an anti-Ub antibody. (E). The assembly of ubiquitin chains was determined at 30° C. in the presence of Ube1, Ube2D2, XIAP, and indicated Ub variants. Samples were taken at the indicated time points, and polyubiquitin chains were detected by immunoblotting with an anti-Ub antibody. (F). HSP70/40 were first incubated with Glow Fold protein at 43° C. for 7 minutes. After incubated on ice for 10 minutes, Ube1, Ube2d3, CHIP, and indicated Ub variants were added and incubated at 30° C. Samples were taken at the indicated time points, and ubiquitin of Glow Flow protein was detected by immunoblotting with an anti-Glow Fold antibody. (G). E1-mediated charging of E2 enzymes by Ub and phos-Ub in a time-course analysis. Reactions were stopped with 2× non-reducing buffer and processed to non-reducing SDS-PAGE. "~Ub~" refers to generation of a thioester with E2 enzyme.
Figure 1:
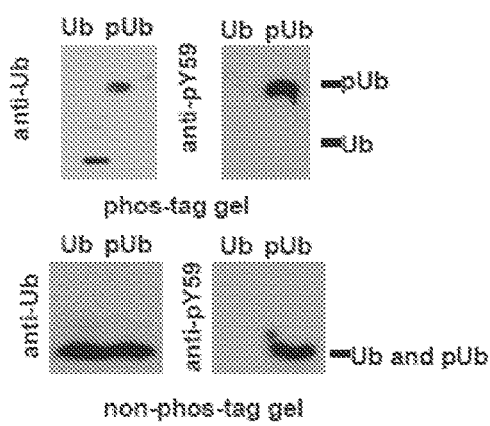
Figure 1:
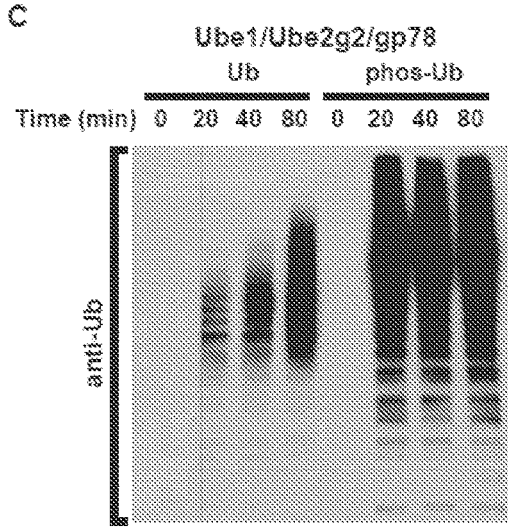
Figure 1:
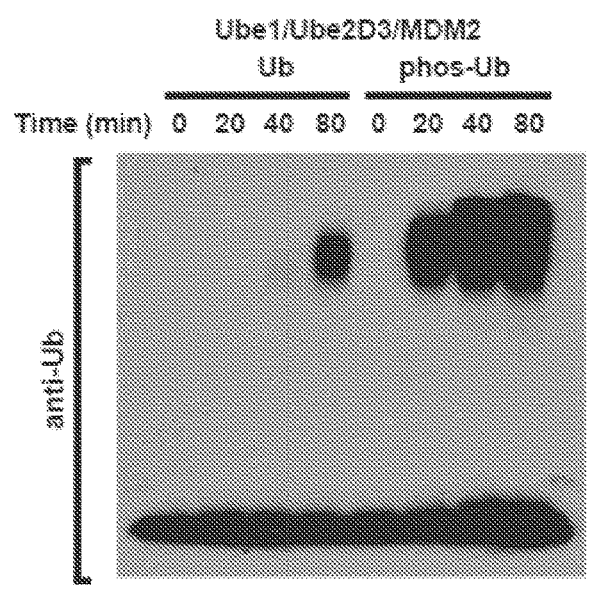
Figure 1:
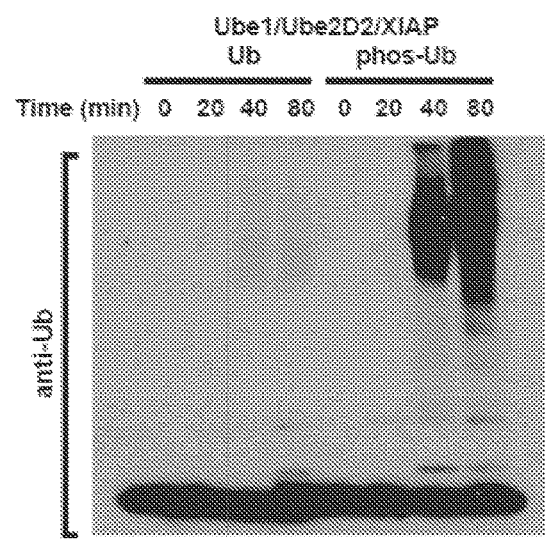
Figure 1:
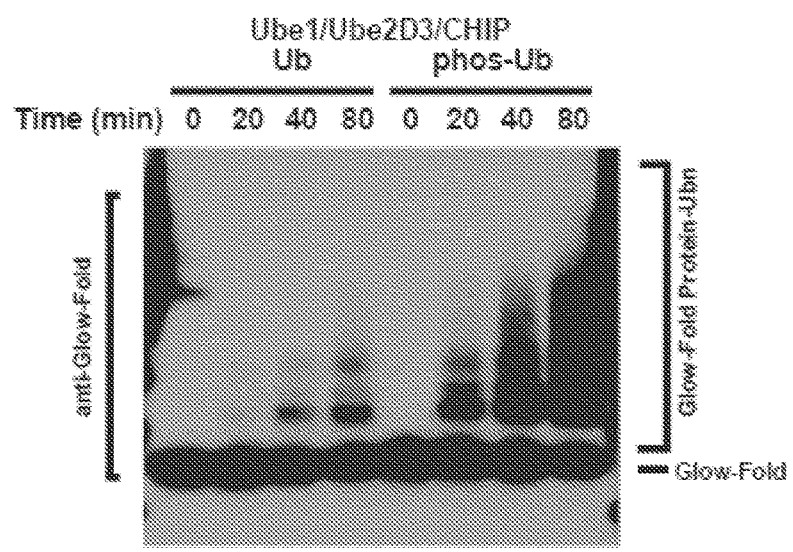
Figure 1:
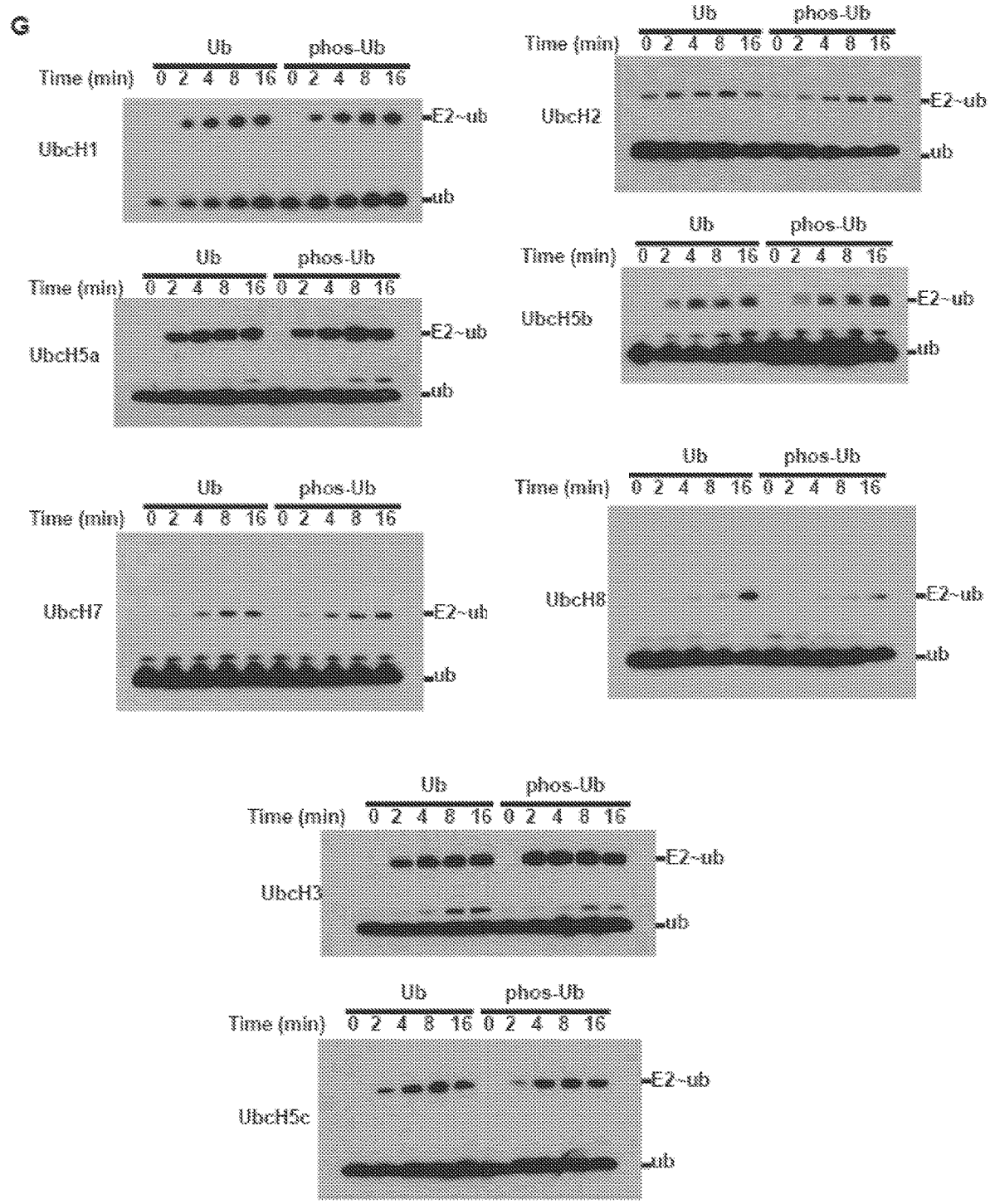

This document provides methods and materials for identifying and/or treating cancers where cancer cells have an elevated level of phosphorylated Ub polypeptides (e.g., an elevated level of Y59 phosphorylated Ub polypeptides). For example, this document provides methods and materials for identifying a mammal (e.g., a human) as having cancer cells having an elevated level of phosphorylated Ub polypeptides (e.g., an elevated level of Y59 phosphorylated Ub polypeptides). Any appropriate mammal can be identified as having cancer cells having an elevated level of phosphorylated Ub polypeptides (e.g., an elevated level of Y59 phosphorylated Ub polypeptides). For example, humans and other primates such as monkeys can be identified as having cancer cells having an elevated level of phosphorylated Ub polypeptides (e.g., an elevated level of Y59 phosphorylated Ub polypeptides). In some cases, dogs, cats, horses, cows, pigs, sheep, mice, or rats can be identified as having cancer cells having an elevated level of phosphorylated Ub polypeptides (e.g., an elevated level of Y59 phosphorylated Ub polypeptides) as described herein.

Any appropriate cancer can be assessed as described herein to determine whether it includes cancer cells having an elevated level of phosphorylated Ub polypeptides (e.g., an elevated level of Y59 phosphorylated Ub polypeptides). For example, breast cancer (e.g., triple-negative breast cancer (TNBC), inflammatory breast cancer (IBC), or HER2-enriched breast cancer), liver cancer, prostate cancer, pancreatic cancer, colon cancer, or brain cancer can be assessed as described herein to determine whether it includes cancer cells having an elevated level of phosphorylated Ub polypeptides (e.g., an elevated level of Y59 phosphorylated Ub polypeptides).

Any appropriate method can be used to assess cancer cells for an elevated level of phosphorylated Ub polypeptides (e.g., an elevated level of Y59 phosphorylated Ub polypeptides). For example, immunohistochemistry (IHC) and Western blot techniques can be used to determine or measure the level of phosphorylated Ub polypeptides within cancer cells. In some cases, an anti-pY59 Ub polypeptide antibody provided herein can be used to detect the presence of Y59 phosphorylated Ub polypeptides within cancer cells. A wild-type human Ub polypeptide can have the amino acid sequence as set forth in GenBank Accession No. AB003730.1

The term "elevated level" as used herein with respect to phosphorylated Ub polypeptide levels refers to a level of phosphorylated Ub polypeptide present within cancer cells (e.g., breast cancer cells) that is greater (e.g., at least 25, 35, 45, 50, 55, 65, 75, 80, 90, or 100 percent greater) than the median level of phosphorylated Ub polypeptide present within normal cells or tissues (e.g., MCF10A or human mammary epithelia cells (HMEC)).

Once a mammal (e.g., a human) is identified as having cancer cells with an elevated level of phosphorylated Ub polypeptides (e.g., an elevated level of Y59 phosphorylated Ub polypeptides) as described herein, the mammal can be classified as having cancer cells with an elevated level of phosphorylated Ub polypeptides (e.g., an elevated level of Y59 phosphorylated Ub polypeptides).

As described herein, this document also provides methods and materials for treating a mammal identified as having cancer cells with an elevated level of phosphorylated Ub polypeptides (e.g., an elevated level of Y59 phosphorylated Ub polypeptides). For example, a mammal (e.g., a human) identified as having cancer cells with an elevated level of phosphorylated Ub polypeptides (e.g., an elevated level of Y59 phosphorylated Ub polypeptides) can be administered one or more tyrosine kinase inhibitors (e.g., one or more EGFR and/or FGFR inhibitors) and/or one or more proteasome inhibitors to reduce the number of cancer cells within that mammal.

Any appropriate mammal identified as having cancer cells with an elevated level of phosphorylated Ub polypeptides (e.g., an elevated level of Y59 phosphorylated Ub polypeptides) can be administered one or more tyrosine kinase inhibitors (e.g., one or more EGFR and/or FGFR inhibitors) and/or one or more proteasome inhibitors to reduce the number of cancer cells within that mammal. For example, humans and other primates such as monkeys identified as having cancer cells with an elevated level of phosphorylated Ub polypeptides (e.g., an elevated level of Y59 phosphorylated Ub polypeptides) can be administered one or more tyrosine kinase inhibitors (e.g., one or more EGFR and/or FGFR inhibitors) and/or one or more proteasome inhibitors to reduce the number of cancer cells within that mammal. In some cases, dogs, cats, horses, cows, pigs, sheep, mice, or rats identified as having cancer cells with an elevated level of phosphorylated Ub polypeptides (e.g., an elevated level of Y59 phosphorylated Ub polypeptides) can be administered one or more tyrosine kinase inhibitors (e.g., one or more EGFR and/or FGFR inhibitors) and/or one or more proteasome inhibitors to reduce the number of cancer cells within that mammal. In addition, any appropriate cancer identified as including cancer cells having an elevated level of phosphorylated Ub polypeptides (e.g., an elevated level of Y59 phosphorylated Ub polypeptides) can be exposed to one or more tyrosine kinase inhibitors (e.g., one or more EGFR and/or FGFR inhibitors) and/or one or more proteasome inhibitors to reduce the number of cancer cells present within a mammal. For example, breast cancer (e.g., triple-negative breast cancer (TNBC), inflammatory breast cancer (IBC), or HER2-enriched breast cancer), liver cancer, prostate cancer, pancreatic cancer, colon cancer, or brain cancer identified as including cancer cells having an elevated level of phosphorylated Ub polypeptides (e.g., an elevated level of Y59 phosphorylated Ub polypeptides) can be exposed to one or more tyrosine kinase inhibitors (e.g., one or more EGFR and/or FGFR inhibitors) and/or one or more proteasome inhibitors to reduce the number of cancer cells present within a mammal.

Any appropriate tyrosine kinase inhibitor or combination of tyrosine kinase inhibitors can be administered to a mammal identified as having cancer cells with an elevated level of phosphorylated Ub polypeptides (e.g., an elevated level of Y59 phosphorylated Ub polypeptides) to reduce the number of cancer cells present within that mammal. Examples of tyrosine kinase inhibitors that can be used as described herein to reduce the number of cancer cells present within a mammal include, without limitation, AG-1478 (available commercially from Selleckchem; Catalog #S2728), PD153035 HCl (available commercially from Selleckchem; Catalog #S1079), PD168393 (available commercially from Selleckchem; Catalog #S7039), Erlotinib (available commercially from Selleckchem; Catalog #S7786), AZD3759 (available commercially from Selleckchem; Catalog #S7971), Dovitinib (available commercially from Selleckchem; Catalog #S1018), and MK-2461 (available commercially from Selleckchem; Catalog #S2774). Additional examples of tyrosine kinase inhibitors that can be used as described herein to reduce the number of cancer cells present within a mammal include, without limitation, Cetuximab (available commercially from Selleckchem; Catalog #A2000), AZD9291 (available commercially from Selleckchem; Catalog #S7297), Gefinitib (available commercially from Selleckchem; Catalog #S1025), Panitumumab (available commercially from McKesson; Catalog #226-310), ZD1839 (available commercially from Selleckchem; Catalog #S1025), Afatinib (available commercially from Selleckchem; Catalog #S1011), Lapatinib (available commercially from Selleckchem; Catalog #S2111), Rociletinib (CO-1686) (available commercially from Selleckchem; Catalog #S7284), Neratinib (available commercially from Selleckchem; Catalog #S2150), Infigratinib (BGJ398) (available commercially from Selleckchem; Catalog #S2183), BLU9931 (available commercially from Selleckchem; Catalog #S7819), AZD4547 (available commercially from Selleckchem; Catalog #S2801), FGF401 (available commercially from Cayman Chemical; Catalog #23029), Debio-1347 (available commercially from Selleckchem; Catalog #S7665), JNJ-42756493 (available commercially from Selleckchem; Catalog #S8401), TAS 120 (available commercially from Cayman Chemical; Catalog #21136), FIIN-2 (available commercially from Cayman Chemical; Catalog #19837), LY2874455 (available commercially from Selleckchem; Catalog #S7057), Derazantinib ARQ 087 (available commercially from MedchemExpress; Catalog #HY-19981), BAY 1163877 (available commercially from MedchemExpress; Catalog #HY-100019), Nintedanib (available commercially from Selleckchem; Catalog #S1010), R04383596 (available commercially from Roche), AZD2171 (cediranib) (available commercially from Selleckchem; Catalog #S1017), Ponatinib (available commercially from Selleckchem; Catalog #S1490), PD173074 (available commercially from Selleckchem; Catalog #S1264), Sorafenib (available commercially from Selleckchem; Catalog #S7397), Sunitinib (SU11248) (available commercially from Selleckchem; Catalog #S7781), Vandetanib ZD6474 (available commercially from Selleckchem; Catalog #S1046), Pazopanib (available commercially from Selleckchem; Catalog #S3012), or Brivanib (available commercially from Selleckchem; Catalog #S1084). See, also, Table 1. In some cases, two or more (e.g., two, three, four, five, six, or more) tyrosine kinase inhibitors can be administered to a mammal identified as having cancer cells with an elevated level of phosphorylated Ub polypeptides (e.g., an elevated level of Y59 phosphorylated Ub polypeptides). For example, two different tyrosine kinase inhibitors can be administered to a human identified as having cancer cells (e.g., breast cancer) with an elevated level of phosphorylated Ub polypeptides (e.g., an elevated level of Y59 phosphorylated Ub polypeptides).

TABLE 1
Tyrosine kinase inhibitors
| Name | Structure |
|---|---|
| Erlotinib | 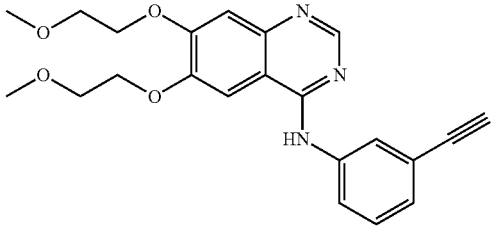 [SMILES: C#Cc1cccc(Nc2ncnc3cc(OCCOC)c(OCCOC)cc23)c1] |
| Gefinitib | 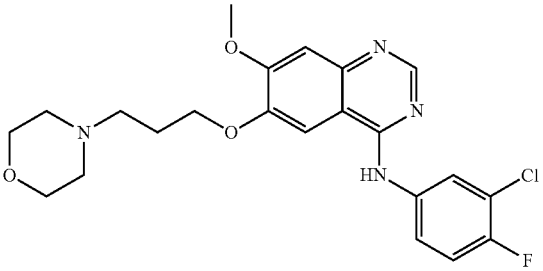 [SMILES: COc1cc2ncnc(Nc3ccc(F)c(Cl)c3)c2cc1OCCCN1CCOCC1] |
| Afatinib | 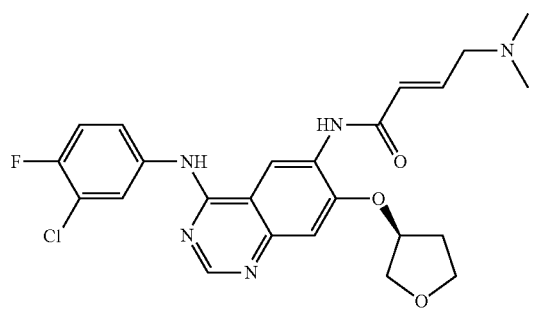 [SMILES: CN(C)C/C=C/C(=O)Nc1cc2c(Nc3ccc(F)c(Cl)c3)ncnc2cc1O[C@H]1CCOC1] |
| Lapatinib | 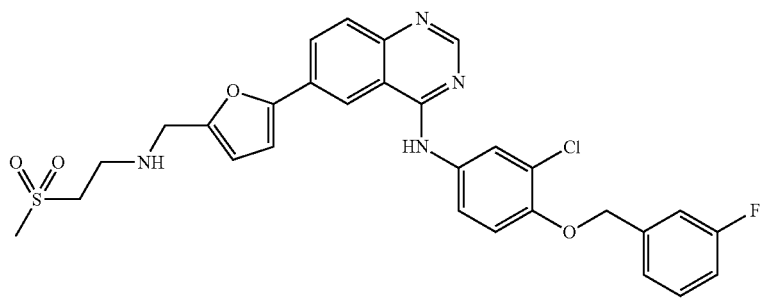 [SMILES: CS(=O)(=O)CCNCc1ccc(-c2ccc3ncnc(Nc4ccc(OCc5cccc(F)c5)c(Cl)c4)c3c2)o1] |
| Rociletinib (CO-1686) | 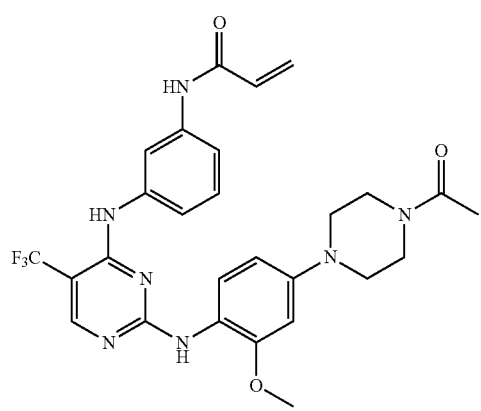 [SMILES: C=CC(=O)Nc1cccc(Nc2nc(Nc3ccc(N4CCN(C(C)=O)CC4)cc3OC)ncc2C(F)(F)F)c1] |

TABLE 1-continued

| Tyrosine kinase inhibitors | |
|---|---|
| Name | Structure |
| Neratinib | |
| Tyrphostin (AG-1478) | |
| AZD9291 | |
| ZD1839 | |
| Infigratinib (BGJ398) | |

TABLE 1-continued

Tyrosine kinase inhibitors

| Name | Structure |
| --- | --- |
| FGF401 | 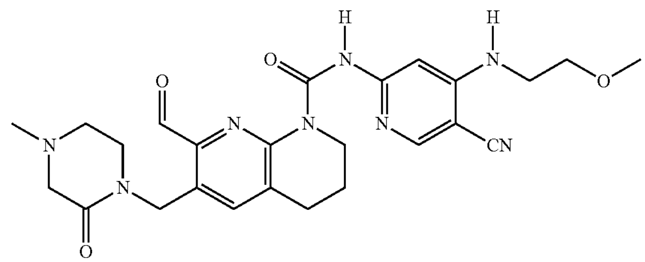 |
| TAS 120 | 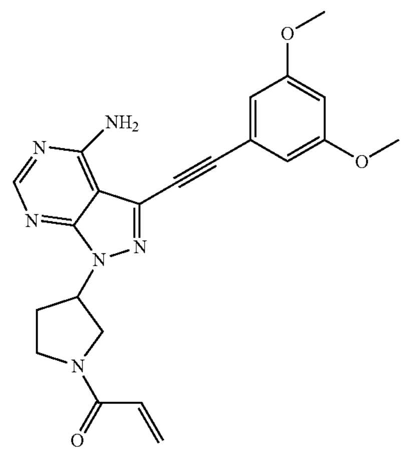 [SMILES: C=CC(=O)N1CCC(n2nc(C#Cc3cc(OC)cc(OC)c3)c3c(N)ncnc32)C1] |
| Derazanitinib ARQ 087 | 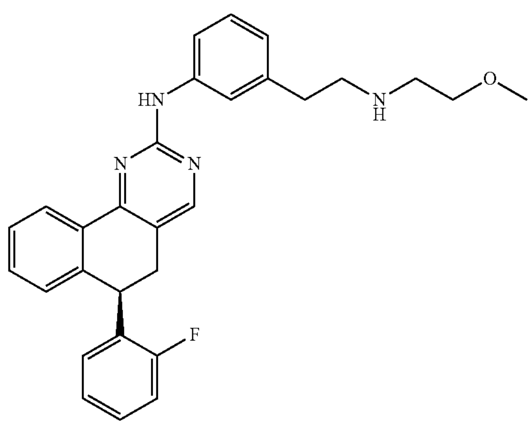 [SMILES: COCCNCCc1cccc(Nc2ncc3c(n2)-c2ccccc2[C@H](c2ccccc2F)C3)c1] |
| BLU9931 | 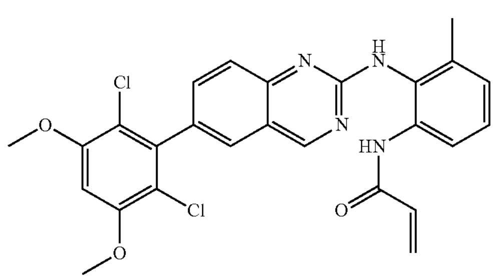 [SMILES: C=CC(=O)Nc1cccc(C)c1Nc1ncc2cc(-c3c(Cl)c(OC)cc(OC)c3Cl)ccc2n1] |

TABLE 1-continued
Tyrosine kinase inhibitors
| Name | Structure |
|---|---|
| Debio-1347 | 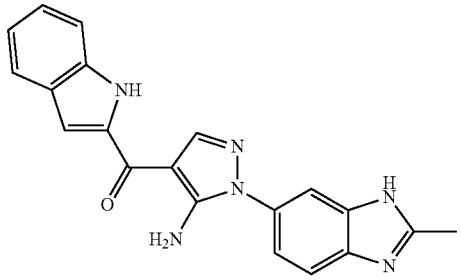 [SMILES: Cc1nc2ccc(-n3ncc(C(=O)c4cc5ccccc5[nH]4)c3N)cc2[nH]1] |
| FIIN-2 | 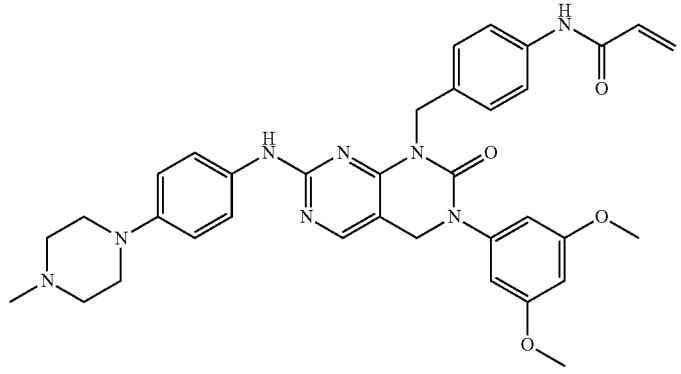 [SMILES: C=CC(=O)Nc1ccc(CN2C(=O)N(c3cc(OC)cc(OC)c3)Cc3cnc(Nc4ccc(N5CCN(C)CC5)cc4)nc32)cc1] |
| BAY 1163877 | 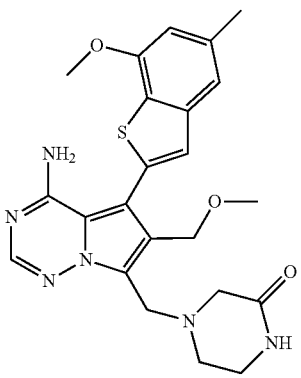 [SMILES: COCc1c(-c2cc3cc(C)cc(OC)c3s2)c2c(N)ncnn2c1CN1CCNC(=O)C1] |
| AZD4547 | 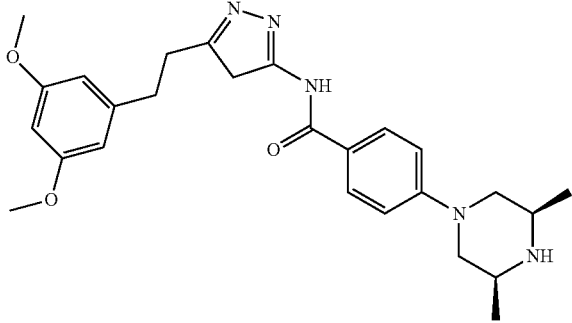 |

TABLE 1-continued

Tyrosine kinase inhibitors

| Name | Structure |
| --- | --- |
| JNJ-42756493 | 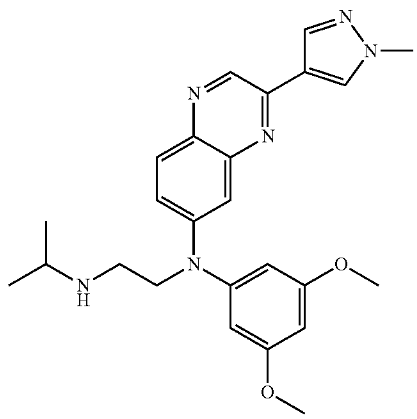 [SMILES: COc1cc(OC)cc(N(CCNC(C)C)c2ccc3ncc(-c4cnn(C)c4)nc3c2)c1] |
| LY2874455 | 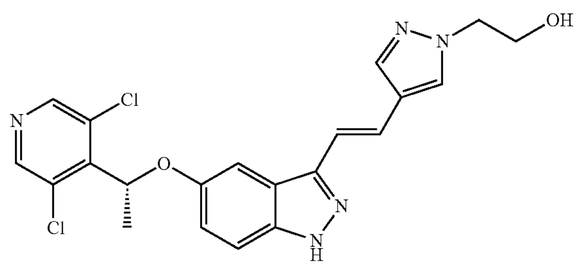 [SMILES: C[C@@H](Oc1ccc2[nH]nc(/C=C/c3cnn(CCO)c3)c2c1)c1c(Cl)cncc1Cl] |
| Nintedanib | 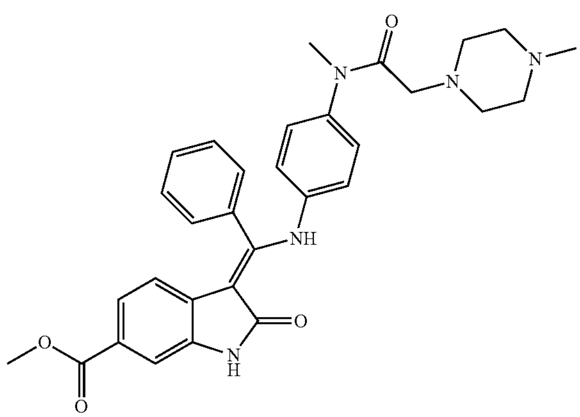 |
| RO4383596 | 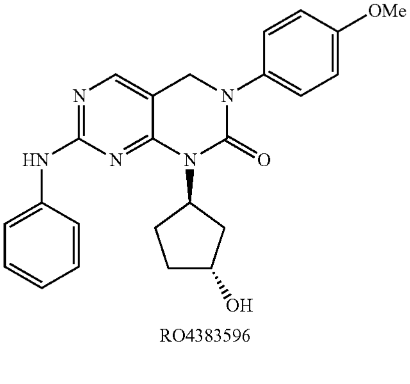 |

TABLE 1-continued
Tyrosine kinase inhibitors
| Name | Structure |
| --- | --- |
| AZD2171 (cediranib), | 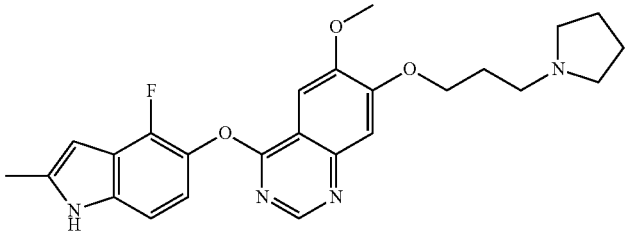 [SMILES: COc1cc2c(Oc3ccc4[nH]c(C)cc4c3F)ncnc2cc1OCCCN1CCCC1] |
| Dovitinib (TKI 258) | 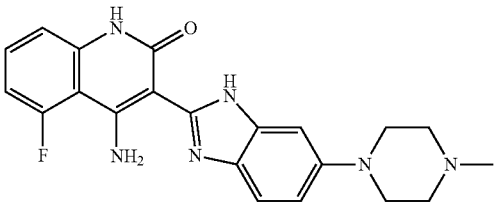 |
| Ponatinib | 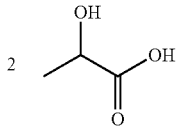 |
| PD173074 | 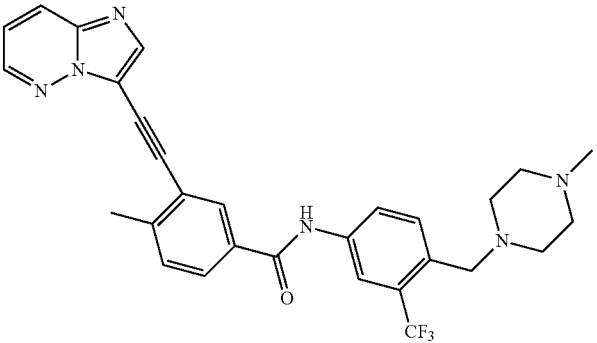 [SMILES: Cc1ccc(C(=O)Nc2ccc(CN3CCN(C)CC3)c(C(F)(F)F)c2)cc1C#Cc1cnc2cccnn12] |

TABLE 1-continued

Tyrosine kinase inhibitors

| Name | Structure |
|---|---|
| Sorafenib | 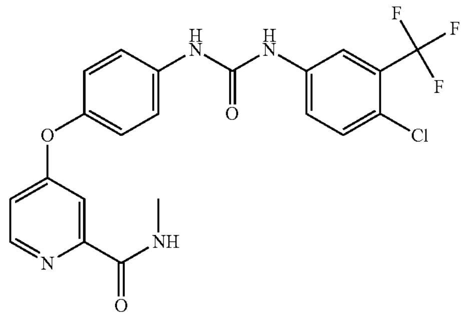 [SMILES: CNC(=O)c1cc(Oc2ccc(NC(=O)Nc3ccc(Cl)c(C(F)(F)F)c3)cc2)ccn1] |
| Sunitinib (SU11248) | 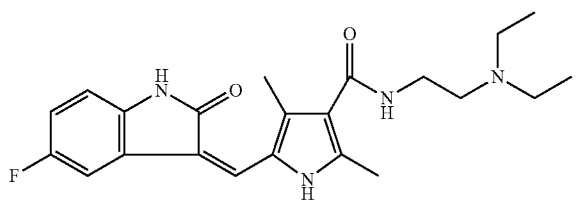 [SMILES: CCN(CC)CCNC(=O)c1c(C)[nH]c(/C=C2\C(=O)Nc3ccc(F)cc32)c1C] |
| Vandetanib ZD6474 | 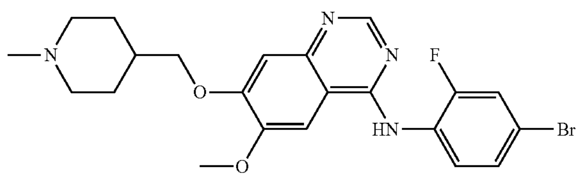 [SMILES: COc1cc2c(Nc3ccc(Br)cc3F)ncnc2cc1OCC1CCN(C)CC1] |
| Pazopanib | 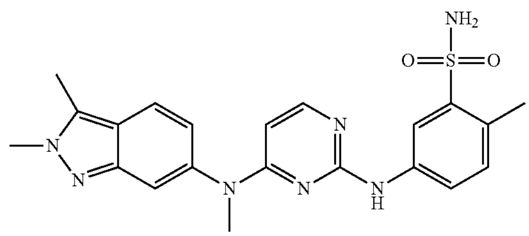 |
| Brivanib | 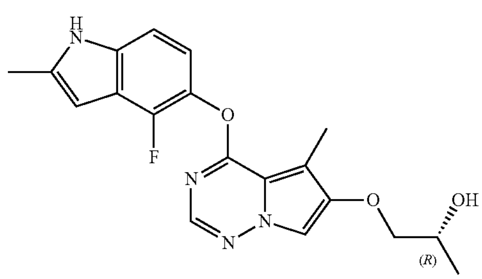 |

In some cases, one or more tyrosine kinase inhibitors and/or one or more proteasome inhibitors can be administered to a mammal once or multiple times over a period of time ranging from days to months. In some cases, one or more tyrosine kinase inhibitors can be formulated into a pharmaceutically acceptable composition for administration to a mammal having cancer cells with an elevated level of phosphorylated Ub polypeptides (e.g., an elevated level of Y59 phosphorylated Ub polypeptides) to reduce the number of cancer cells within that mammal. For example, a therapeutically effective amount of a tyrosine kinase inhibitor (e.g., Erlotinib) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more tyrosine kinase inhibitors and/or one or more proteasome inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more tyrosine kinase inhibitors and/or one or more proteasome inhibitors can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments, and the judgment of the treating physician.

An effective amount of a composition containing one or more tyrosine kinase inhibitors can be any amount that reduces the number of cancer cells within a mammal having cancer cells with an elevated level of phosphorylated Ub polypeptides (e.g., an elevated level of Y59 phosphorylated Ub polypeptides) without producing significant toxicity to the mammal. For example, an effective amount of a tyrosine kinase inhibitor such as Erlotinib can be from about 0.25 mg/kg to about 100 mg/kg (e.g., from about 0.3 mg/kg to about 11 mg/kg, from about 1 mg/kg to about 10 mg/kg, from about 2 mg/kg to about 10 mg/kg, from about 5 mg/kg to about 10 mg/kg, from about 6 mg/kg to about 10 mg/kg, from about 6 mg/kg to about 8 mg/kg, or from about 7 mg/kg to about 9 mg/kg). In some cases, from about 100 mg to about 1000 mg (e.g., from about 250 mg to about 1000 mg, from about 300 mg to about 1000 mg, from about 400 mg to about 1000 mg, from about 100 mg to about 900 mg, from about 100 mg to about 800 mg, from about 400 mg to about 800 mg, or from about 500 mg to about 700 mg) of a tyrosine kinase inhibitor can be administered to an average sized human (e.g., about 75-85 kg human) per administration (e.g., per daily or weekly administration) for about two to about twelve weeks. In some cases, a tyrosine kinase inhibitor can be administered daily within one of these dose ranges for 21 days followed by a seven-day rest period.

If a particular mammal fails to respond to a particular amount, then the amount of a tyrosine kinase inhibitor and/or a proteasome inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of a tyrosine kinase inhibitor and/or a proteasome inhibitor can be any amount that reduces the number of cancer cells within a mammal having cancer cells with an elevated level of phosphorylated Ub polypeptides (e.g., an elevated level of Y59 phosphorylated Ub polypeptides) without producing significant toxicity to the mammal. For example, the frequency of administration of a tyrosine kinase inhibitor can be from about once a day to about once a month (e.g., from about once a week to about once every other week). The frequency of administration of a tyrosine kinase inhibitor can remain constant or can be variable during the duration of treatment. A course of treatment with a composition containing a tyrosine kinase inhibitor can include rest periods. For example, a composition containing one or more tyrosine kinase inhibitors and/or one or more proteasome inhibitors can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more tyrosine kinase inhibitors and/or one or more proteasome inhibitors can be any duration that reduces the number of cancer cells within a mammal having cancer cells with an elevated level of phosphorylated Ub polypeptides (e.g., an elevated level of Y59 phosphorylated Ub polypeptides) without producing significant toxicity to the mammal. In some cases, the effective duration can vary from several days to several months. In general, the effective duration for reducing the number of cancer cells within a mammal having cancer cells with an elevated level of phosphorylated Ub polypeptides (e.g., an elevated level of Y59 phosphorylated Ub polypeptides) can range in duration from about six weeks to about six months. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and/or the severity of one or more symptoms related to the condition being treated (e.g., cancer) can be monitored. Any appropriate method can be used to determine whether or not the number of cancer cells (e.g., the number of cancer cells with an elevated level of phosphorylated Ub polypeptides such as an elevated level of Y59 phosphorylated Ub polypeptides) present within a mammal is reduced. For example, techniques (e.g., cell staining techniques) can be performed to determine the number of cancer cells having an elevated level of phosphorylated Ub polypeptides (e.g., an elevated level of Y59 phosphorylated Ub polypeptides) present within a mammal following administration one or more tyrosine kinase inhibitors.

This document also provides anti-phosphorylated Ub polypeptide antibody preparations, methods for making anti-phosphorylated Ub polypeptide antibody preparations, and methods for using anti-phosphorylated Ub polypeptide antibody preparations to detect phosphorylated Ub polypeptides. For example, this document provides anti-phosphorylated Ub polypeptide antibodies (also referred to herein as anti-pUb polypeptide antibodies or anti-pUb antibodies). Examples of anti-pUb polypeptide antibodies provided herein include, without limitation, anti-phosphorylated Y59 Ub polypeptide antibodies (also referred to herein as anti-pY59 Ub polypeptide antibodies or anti-pY59 Ub antibodies).

In some cases, an anti-pUb antibodies provided herein (e.g., an anti-pY59 Ub antibody) can bind to a phosphorylated version of a Ub polypeptide with little or no detectable binding to the unphosphorylated version of that Ub polypeptide. For example, an anti-pY59 Ub antibody such as rabbit anti-UbpY59 antibody can bind to LSD(pY)NIQKESTLHLC (SEQ ID NO:1) with little or no detectable binding to LSDYNIQKESTLHLC (SEQ ID NO:2).

The term "antibody" as used herein refers to intact antibodies as well as antibody fragments that retain some ability to bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

Any appropriate method can be used to produce Fab fragments from intact antibodies. For example, standard papain digestion methods can be used to make a Fab antibody preparation. In some cases, an anti-pUb antibody (e.g., anti-pY59 Ub antibody) preparation provided herein can be a preparation of whole antibodies or Fab fragments of humanized or fully-human anti-pUb antibodies (e.g., anti-pY59 Ub antibodies).

Antibodies provided herein can be prepared using any appropriate method. For example, a sample containing LSD(pY)NIQKESTLHLC (SEQ ID NO:1) can be used as an immunogen to elicit an immune response in an animal such that specific antibodies are produced. The immunogen used to immunize an animal can be chemically synthesized. In some cases, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well known to those skilled in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan et al., Unit 9, Current Protocols in Immunology, Wiley Interscience, 1994).

The preparation of monoclonal antibodies also is well known to those skilled in the art. See, e.g., Kohler & Milstein, Nature 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, VOL. 10, pages 79 104 (Humana Press 1992).

In addition, methods of in vitro and in vivo multiplication of monoclonal antibodies are well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

In some cases, the antibodies provided herein can be made using non-human primates. General techniques for raising therapeutically useful antibodies in baboons can be found, for example, in Goldenberg et al., International Patent Publication WO 91/11465 (1991) and Losman et al., Int. J. Cancer, 46:310 (1990).

In some cases, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., Proc. Nat'l. Acad. Sci. USA 86:3833 (1989). Techniques for producing humanized monoclonal antibodies are described, for example, by Jones et al., Nature 321:522 (1986); Riechmann et al., Nature 332:323 (1988); Verhoeyen et al., Science 239:1534 (1988); Carter et al., Proc. Nat'l. Acad. Sci. USA 89:4285 (1992); and Sandhu, Crit.

Rev. Biotech. 12:437 (1992); Singer et al., *J. Immunol.* 150:2844 (1993). In some cases, humanization such as super humanization can be used as described elsewhere (Hwang et al., *Methods,* 36:35-42 (2005)). In some cases, SDR grafting (Kashmiri et al., *Methods,* 36:25-34 (2005)), human string content optimization (Lazar et al., *Mol. Immunol.,* 44:1986-1998 (2007)), framework shuffling (Dall'Acqua et al., *Methods,* 36:43-60 (2005); and Damschroder et al., *Mol. Immunol.,* 44:3049-3060 (2007)), and phage display approaches (Rosok et al., *J. Biol. Chem.,* 271:22611-22618 (1996); Radar et al., *Proc. Natl Acad. Sci.* USA, 95:8910-8915 (1998); and Huse et al., *Science,* 246:1275-1281 (1989)) can be used to obtain anti-pUb antibody preparations. In some cases, fully human antibodies can be generated from recombinant human antibody library screening techniques as described elsewhere (Griffiths et al., *EMBO J.,* 13:3245-3260 (1994); and Knappik et al., *J. Mol. Biol.,* 296:57-86 (2000)).

Antibodies provided herein can be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., *Ann. Rev. Immunol.* 12: 433 (1994). Cloning and expression vectors that are useful for producing a human immunoglobulin phage library can be obtained, for example, from STRATAGENE Cloning Systems (La Jolla, Calif.).

In addition, antibodies provided herein can be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody secreting hybridomas. Methods for obtaining human antibodies from transgenic mice are described by Green et al. (*Nature Genet.,* 7:13 (1994)), Lonberg et al. (Nature, 368:856 (1994)), and Taylor et al. (*Int. Immunol.,* 6:579 (1994)).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, Fab fragments can be produced by enzymatic cleavage of antibodies with papain. In some cases, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036,945 and 4,331,647). See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used provided the fragments retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated. Thus, a substantially pure antibody is any antibody that is removed from its natural environment and is at least 60 percent pure. A substantially pure antibody can be at least about 65, 70, 75, 80, 85, 90, 95, or 99 percent pure.

As described herein, anti-pUb antibodies (e.g., anti-pY59 Ub antibodies) provided herein can be used to detect phosphorylated Ub polypeptides (e.g., pY59 Ub polypeptides).

The invention will be further described in the following examples, which do not limit the scope of the invention described in the claims.

EXAMPLES

Example 1—Tyrosine Phosphorylation of Ubiquitin Regulates Cellular Protein Turnover Materials and Methods Materials Reagents were obtained from the indicated sources: antibodies to Ub (Santa Cruz, sc-8017), K48-linked Ub (Millipore, 05-1307), K63-linked Ub (EPR8590-448; (ab179434)), p-Tyr (Cell signaling technology, 9411), Phospho-Akt (Ser473) Antibody (Cell signaling technology, #9271), Phospho-p44/42 MAPK (Cell signaling technology, #4370), ADRM1 (Proteintech), actin (Sigma, A2228). $^{32}$P-ATP and $^{35}$S-methionine were obtained from PerkinElmer Life Sciences. ATP, L-methionine, chloroquine, MG132, cycloheximide, trichloroacetic acid were obtained from Sigma. EGF and FGF basic, methionine-free DMEM, L-GlutaMAX, and transfection reagents Lipofectamine 2000 were obtained from Thermo Fisher Scientific Inc. Bortezomib, FGFR inhibitor TKI-258, EGFR inhibitor AG-1478, PI3k inhibitor LY294002, and MEK Inhibitor U0126 were obtained from Selleck Chemicals Inc. The Mdm2/HDM2 Ubiquitin Ligase Kit (K-200B), cIAP-1/HIAP2 Ubiquitin Ligase Kit (K-260), ITCH/AIP4 Ubiquitin Ligase Kit (K-270), CHIP Ubiquitin Ligase Kit (K-280), UBE1, Ub, and Ub-VS were obtained from RnD Inc. Biotin-Ahx-ubiquitin (pTyr59) and Biotin-Ahx-ubiquitin (synthetic) were obtained from Ubiquigent Inc. Phos-Tag gels were obtained from Wako chemicals.

DNA Constructs

Ub wild type was cloned into pET-28a vector (Novagen). pBabe EGFR (L858R/T790M) (Plasmid #32073) were obtained from Addgene. FGFR2 WT and FGFR2 KR were obtained from Dr. Taro Hitosugi. pTO-sh Ub and pTO-Ub-WT plasmids were obtained from Dr. Z. James Chen (UT Southwestern). EGFR wild type and Y1045F mutant were obtained from Dr. Yosef Yarden (Weizmann Institute of Science). Ub Y59F mutants were generated by site-directed mutagenesis (Stratagene). Plasmid encoding for His-tag USP2cc (pET15-USP2cc) was obtained from Wade Haprer (Harvard Medical School) and Eric J. Bennett (University of California-San Diego).

Cell Lines

NIH-3T3, MDA-MB-468, and HEK293 cell lines were maintained in DMEM containing 10% fetal bovine serum and were *mycoplasma* free. The MDA-MB-468 cell line stably expressing Ub shRNA and Ub WT and Y59F mutant were maintained in DMEM containing 10% tetracycline-free fetal bovine serum. Dox were added to the medium when indicated.

Ub Replacement System

MDA-MB-468 parental Ub-replacement cells were generated as described elsewhere (Xu et al., *Mol. Cell,* 36:302-314 (2009)). All Ub-replacement cells were made as described elsewhere (Xu et al., *Mol. Cell,* 36:302-314 (2009)).

Protein Synthesis with Metabolic Radiolabeling

Cells were serum starved for 48 hours in 6-well plate. To assess protein synthesis, cells were starved for 30 minutes with methionine-free DMEM and radiolabeled for 20 to 30 minutes with $^{35}$S-Met. Cells were lysed in RIPA buffer (50 mM Tris-HCl, pH 7.4, 1% sodium deoxycholate, 0.1% SDS, 1% NP-40, 150 mM NaCl, 1 mM EDTA, 10 mM sodium pyrophosphate, 10 mM glycerol 2-phosphate, 50 mM NaF, 0.5 mM sodium orthovanadate and protease inhibitor cocktail). Following centrifugation at 13,000 g, supernatants were spotted on a Whatman 3 MM paper preblocked with 0.1% Methionine. Dry paper pieces containing the spotted samples were placed in 10% cold Trichloroacetic acid (TCA) for 20 minutes and transferred into a boiling solution of 5% TCA for 15 minutes to hydrolyze radioactive charged Met-tRNA. Paper fragments were then washed again with 5% TCA and 95% ethanol at room temperature and dried. The radioactivity of each sample was determined by scintillation counting. The relative rates of protein synthesis were normalized to control group.

Measurement of Protein Degradation

To assess protein degradation, cells were starved for 30 minutes with methionine-free DMEM and pulse labelled for 16-24 hours with 0.5 mL of medium containing 0.1 mCi of $^{35}$S-Met. Cells were then washed with Met-free DMEM and chased for 4 hours in DMEM containing 2 mM non-radioactive Met. After washing in cold PBS, cells were treated in chase medium for various times, and the remaining radioactivity in cells was measured as described elsewhere (Taelman et al., *Cell,* 143:1136-1148 (2010)).

Measurement of Intracellular Amino Acid Levels

Amino acid levels were quantified using an L-Amino Acid Assay Kit (Abcam) following the manufacturer's instructions. Briefly, cells were washed with PBS and lysed in Assay Buffer. A standard curve for quantification was established, using L-Amino Acid Standards in a concentration range from 0 to 80 nMol/mL. 100 µL Reaction Mix was added to each well containing the L-Amino Acid standard or test samples, and the reaction was incubated for 30 minutes at 37° C. Fluorescence was monitored in an Infinite® M1000 PRO Fluorometer (TECAN) at excitation and emission wavelengths of 535 nm and 590 nm, respectively, and was normalized to cell numbers in parallel wells. Relative intracellular amino acid levels were normalized to control group.

Immunoblotting

Cell lysates were prepared, and immunoprecipitation and immunoblotting were performed as described elsewhere (Deng et al., *Mol. Cell,* 61:614-624 (2016)). In brief, cells were lysed with NETN buffer (20 mM Tris-HCl, pH 8.0, 100 mM NaCl, 1 mM EDTA, 0.5% Nonidet P-40) containing 50 mM β-glycerophosphate, 10 mM NaF, and 1 mg/mL each of pepstatin A and aprotinin. Whole cell lysates were centrifuged at 12000 rpm for 15 minutes. Whole cell lysates were incubated with 2 of antibody and protein A or protein G Sepharose beads (Amersham Biosciences) for 2 hours or overnight at 4° C. The immunocomplexes were then washed with NETN buffer for three times and separated by SDS-PAGE. Immunoblotting was performed following standard procedures.

Ub Purification

Constructs of his6-tagged Ub and Ub Y59F for bacterial expression were expressed in BL21 cells by inducing with 150 µM IPTG (0D600~1.0) at 18° C. The cells were grown at 18° C. for 12 hours and lysed by sonication in His-Binding Buffer (50 mM Tris-Cl (pH8.0), 5 mM Imidazole, 100 mM NaCl, 0.1 mM EDTA, 1 mM PMSF). After centrifugation (45000×g, 30 minutes, 4° C.), the supernatant was applied to Ni-NTA agarose beads (QIAGEN), agitated for 1 hour at 4° C., and subsequently washed in His-Wash Buffer (50 mM Tris-Cl (pH8.0), 300 mM NaCl, 10-20 mM Imidazole, 0.1 mM EDTA). The his6 tagged protein was eluted in His-Elution Buffer (50 Mm Tris-Cl (pH8.0), 50 mM NaCl, 300 mM Imidazole, 0.1 mM EDTA). Protein containing fractions were pooled, dialyzed to PBS, concentrated using a 3-kDa MWCO spin concentrator (Millipore), and flash frozen in liquid nitrogen.

For purification of untagged ubiquitin, human ubiquitin DNA was subcloned into pET28a with N-terminal 6His-tag removed through site mutagenesis. For phosphorylated ubiquitin, the FGFR2 kinase domain (456-770) was fused to the c-terminal of ubiquitin encoding ubiquitin-FGFR2-6His-tag to force the phosphorylation of Ub Y59 (FIG. 1A). Both ubiquitin-6His-tag and ubiquitin-FGFR2-6His-tag were produced in Rossetta (DE3) *E. coli* cells and purified by Ni-NTA beads followed by removal of the c-terminal fusion protein by incubation with His-USP2cc for overnight. His-USP2cc and c-terminal fusion proteins were removed by Ni-NTA binding. Ubiquitin and phosphorylated ubiquitin were filtered through a 30 kDa filter to remove other unspecific contamination, concentrated in a 3 kDa molecular-mass cut-off filter, and dialyzed to PBS buffer. The phosphorylation status of Ub and phos-Ub was checked with phos-tag gel (FIG. 1B).

In Vitro Ubiquitination Assay

Substrate free ubiquitination experiments were performed as described elsewhere (Li et al., *Nature,* 446:333-337 (2007)). Briefly, E1 (60 nM), Ube2g2 (200 nM), and gp78c (300 nM) were incubated with ubiquitin (10 µM) at 30° C. in buffers containing 25 mM Tris HCl, pH 7.4, 2 mM ATP, 5 mM MgCl$_2$, 5 mM MnC$_2$ and 0.1 mM DTT. p53 ubiquitination were performed as follow. Briefly, E1 (60 nM), UBE2D3 (200 nM), MDM2 (300 nM), and 1 µM p53 were incubated with ubiquitin (10 µM) at 30° C. in buffers containing 25 mM Tris HCl, pH 7.4, 2 mM ATP, 5 mM MgCl$_2$, 5 mM MnCl$_2$, and 0.1 mM DTT. Auto-ubiquitination of cIAP was performed as follow. E1 (100 nM), Ube2D2 (200 nM), and cIAP (1 µM) were incubated with ubiquitin (10 µM) at 30° C. in buffers containing 25 mM Tris HCl, pH 7.4, 2 mM ATP, 5 mM MgCl$_2$, 5 mM MnCl$_2$, and 0.1 mM DTT. ITCH ubiquitination of Glow-fold by CHIP were performed using ubiquitin ligase kit (Boston Biochem K-260, K-270, K-280) following the manufacturer's instructions. 100 ng of EGFR or FGFR or 1 µg of Ub4 or phos-Ub4 were included in a 50 µL reaction to test their effect on ubiquitination.

In Vitro Kinase Assay

Purified active tyrosine kinases EGFR, PDGFR, FGFR2, KDR, EPHB3, Abl1, Ack1, JAK1, and MEK1 were purchased from Signal Chem. Tetra-ubiquitin (Ub4) chains Ml-linear, K6, K11, K29, K33, K48, and K63 were purchased from Bioston Biochem. 100 ng of purified tyrosine kinases were incubated with 1 µg of different Ub4 chains in the kinase reaction buffer (15 mM HEPES, pH 7.0, 1 mm dithiothreitol, 5 mM MgCl$_2$, 5 mM MnCl$_2$, and 1 mM ATP) at 30° C. for 30 minutes. The product was separated by SDS-PAGE and subjected to immunoblotting with pan pY antibody or pY59 antibody.

To generate phosphorylated Ub4, 1 μg of EGFR was mixed with 10 μg of K48 Ub4 chain in the kinase reaction buffer at 30° C. overnight. The reactions were stopped by adding 20 mM EDTA and passed through GSH-beads to remove EGFR in the reaction system. Phosphorylated Ub4 was further dialyzed to PBS and flash frozen in liquid nitrogen.

Antibody Generation

Antigen peptide (LSD(pY)NIQKESTLHLC; SEQ ID NO:1) was conjugated with KLH as immunogen, and rabbits were immunized with the conjugated peptide. The antisera were affinity-purified with AminoLink Plus immobilization and purification kit (Pierce).

In Vivo Tumorigenesis Study

For ubiquitin replacement doxycycline-inducible xenograft experiments, 5×10$^6$ cells were re-suspended in matrigel and injected subcutaneously into athymic nude mice. Two weeks after injection (tumor size around 100 mm$^3$), doxycycline was administered in drinking water. Tumor growth was measured using a vernier caliper at the indicated times after injection, and the tumor volume was calculated as length×width×height. Five weeks later, mice were euthanized, and tumors were removed and weighed.

Tissue Microarray

The tissue arrays of breast cancer samples were purchased from U.S. Biomax (BR-802 and BC08013). Samples were deparaffinized and rehydrated. Antigen retrieval was done by using 0.01 M sodium-citrate buffer (pH 6.0) in a microwave oven. To block endogenous peroxidase activity, the sections were treated with 1% hydrogen peroxide in methanol for 30 minutes. After 1-hour pre-incubation in 10% normal serum to prevent nonspecific staining, the samples were incubated with the antibodies against pY59 (homemade, 1:100) and K48 (Cell Signaling #, 4289, 1:500) at 4° C. overnight. The sections were then incubated with a poly-HRP secondary antibody, for 30 minutes at room temperature. Color was developed with the DAB. Counterstaining was carried out using hematoxylin. The immunostaining was scored by pathologists in a blinded manner.

Statistical Analyses

Unless otherwise specified, all experiments were performed at least three times. The sample size for each experiment was provided in the figure legends or elsewhere, and unless otherwise specified, represented biological replicates or independent experiments performed on different days, each with technical triplicates. All values were reported as mean±SD. Statistical significance for all pairwise comparisons was evaluated with a two-tailed Student's t-test or two-way ANOVA test, and a P value <0.05 was considered significant. P<0.01 was considered very significant. The biochemical measurements made provided data that was of a normal distribution, and there was a similar variance among the groups.

Di-Ub Synthesis Assay

UbcH5B (2.5 μM) was charged with mouse Uba1 (1 μM) and Biotin-Ahx-Ub or Biotin-Ahx phosUb (50 μM) for 15 minutes at 23° C. in buffer containing 50 mM Tris-HCl (pH 7.6), 50 mM NaCl, 5 mM MgCl$_2$, 5 mM ATP, and 1 mM DTT. The charging reaction was treated with 10 mM N-ethylmaleimide (NEM) and 50 mM EDTA for 15 minutes at room temperature. UbcH5B~bioitin-Ub variants were then mixed with Ub or phosUb (1 mM). The reactions were quenched at indicated times with 2×SDS loading buffer containing 500 mM DTT, resolved by SDS-PAGE, and stained with HRP conjugated streptavidin.

Colony and Soft Agar Colony-Formation Assays

The soft agar colony-formation assay was performed as described elsewhere (Shim et al PNAS, 94:6658-6663 (1997)). Cells were plated in 0.3% top agarose with 1% base agar in 35 mm dishes. Doxycycline and AG-148 were included in both top agarose and base agar as indicated. The cells in the plates were cultured for 2 weeks. Colonies were counted at room temperature under a light microscope.

E2 Charging Assay

The E2 panel including different E2 enzymes was purchased from Enzo (BML-UW9920-0001). For E2 charging assays, 100 nM of E1 was mixed with 2 μM E2 enzymes and 15 μM Ub or phosphoUb in ligation buffer (40 mM Tris pH 7.55 mM MgCl$_2$, 5 mM ATP, 0.6 mM DTT) and incubated at 30° C. At indicated time points, 10 μL samples were mixed with 10 μL 2×SDS loading buffer without reducing agent, resolved on 4-12% gradient SDS PAGE gels, and blotted with anti-Ub antibody.

Cell Proliferation and MTS Assay

90 μL of cells (5×10$^5$ cells/mL) were plated into each well of 96-well plates (Corning, Lowell, Mass.; MacLean et al., Bioinformatics, 26:966-968 (2010)) and were treated with 10 μL of bortezomib at the final concentrations of 0, 0.0457, 0.1372, 0.4115, 1.2346, 3.7037, 11.1111, 33.3333 and 100 nM. 72 hours after bortezomib treatment, 20 μL of MTS regent (Sigma) was added to each well and incubated for an additional 3 hours. Plates were then read in a microplate reader at absorbance of OD 490 (Tecan AG, Switzerland).

Preparation of Internal AQUA Peptides

Figure 2:
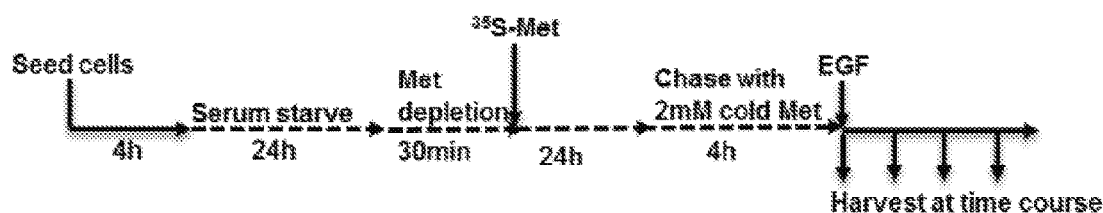
FIG. 2. EGFR activation increases proteasomal degradation and Ubiquitin Conjugates in cells. (A). Schematic diagram of the experimental design for the pulse-chase measurements of protein degradation. (B to J). Western blot images representative of the three independent experiments quantified in FIG. 3D (B to D), FIG. 3E (E to G), and FIG. 3F (H to J). (K). MDA-MB-468 cells were serum starved for 48 hours and then incubated in medium containing vehicle or 20 ng EGF for different time courses. Cells were harvested and processed to UB-AQUA proteomics analysis for individual UB chain linkage types. The intensities were quantitated and normalized to that of the non-treated group. Data were mean±SD of three independent experiments. (**: $p<0.01$, *: $p<0.05$, Student's t-test). (L). MDA-MB-468 cells were serum starved for 48 hours and then incubated in medium containing vehicle, 20 ng EGF, or 20 ng EGF and 100 μM AG-1478. Cells were harvested and processed to UB-AQUA proteomics analysis for individual UB chain linkage types. The amount of each Ub chain linkages were quantitated and normalized to that of the non-treated group. Data are mean±SD of three independent experiments. (**: $p<0.01$, *: $p<0.05$, Student's t-test). (M). AQUA peptides used to quantify diGLY and phosphopeptides. Internal standards were isotopically labelled ($^{13}C$, $^{15}N$), and the corresponding residue(s) were underlined. Modified residues with ubiquitination and phosphorylation were indicated by (GG) or p, respectively. Fragment ions used for quantitation are listed.
Figure 2:
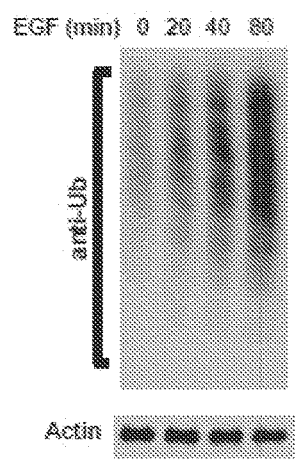
Figure 2:
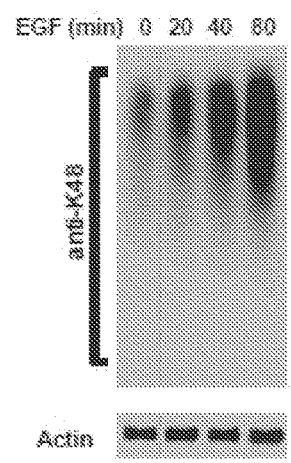
Figure 2:
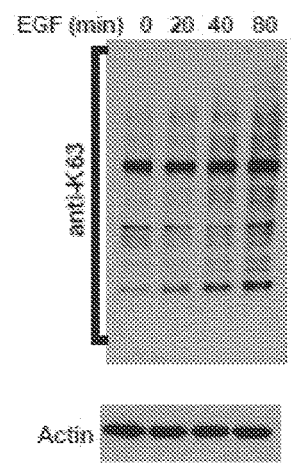
Figure 2:
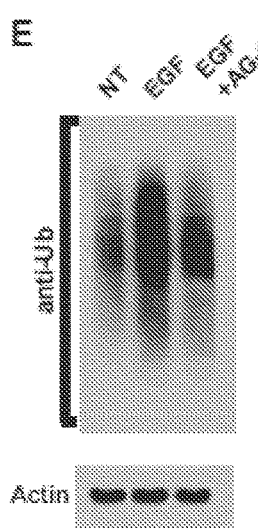
Figure 2:
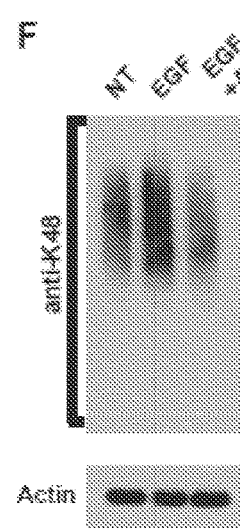
Figure 2:
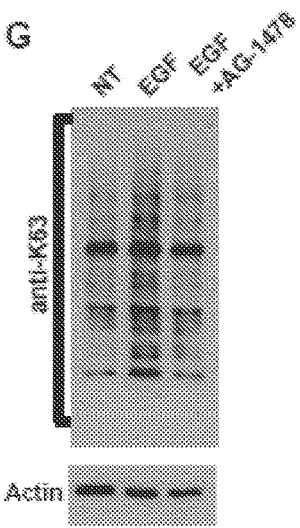
Figure 2:
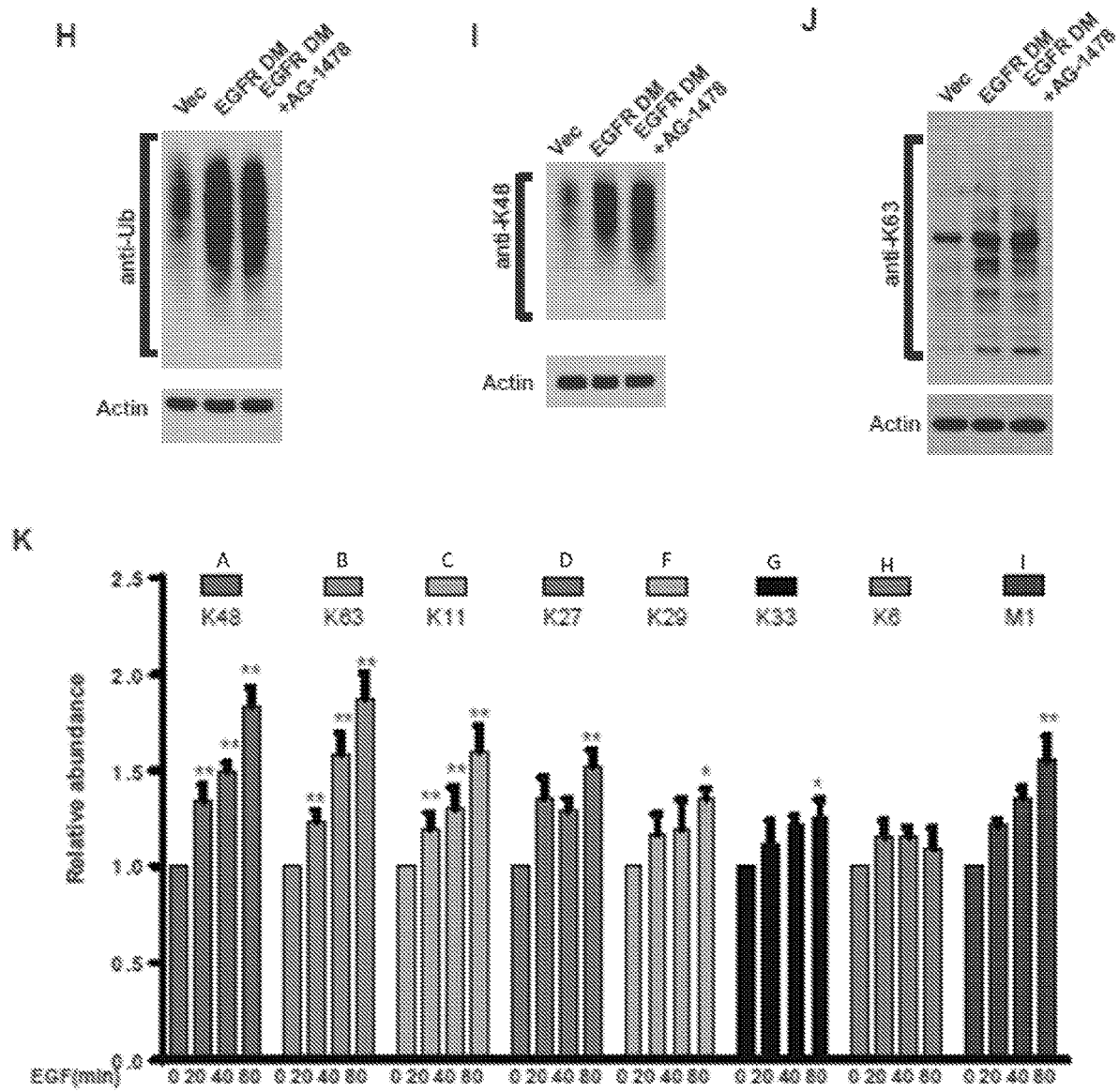
Figure 2:
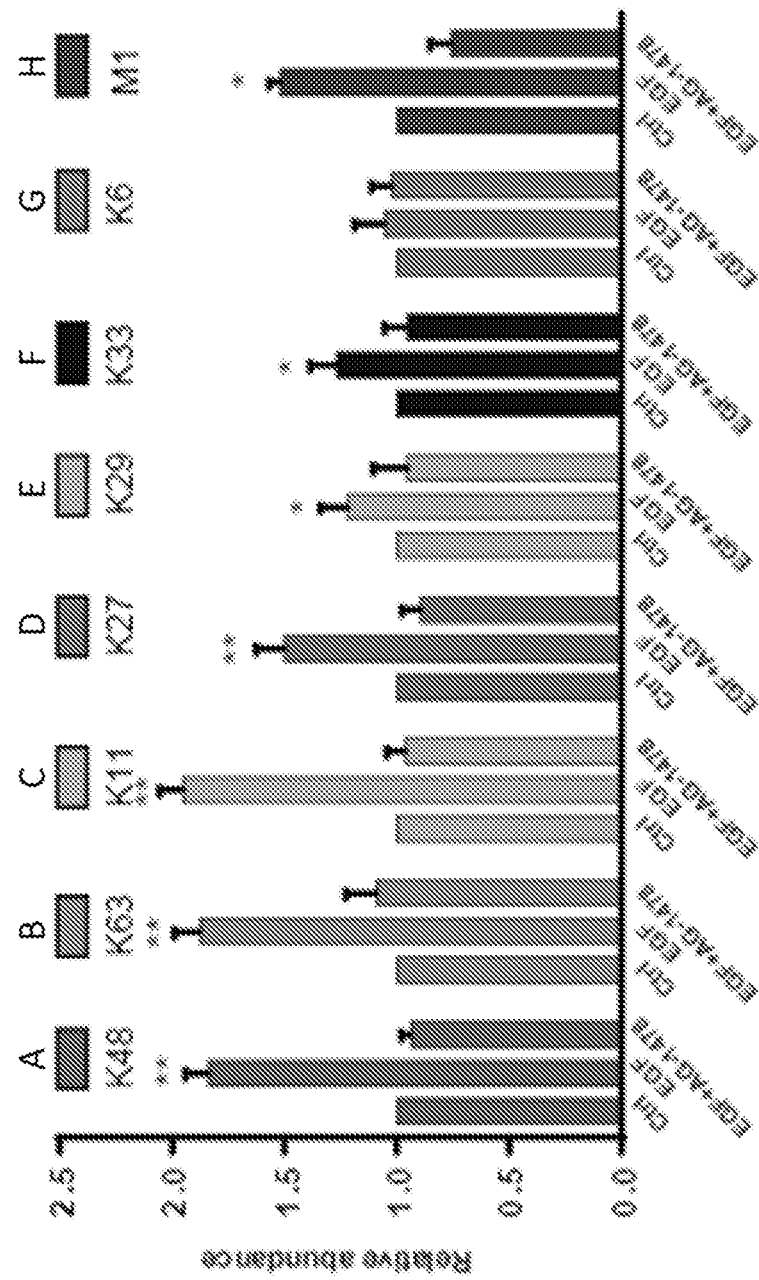

Synthetic isotopically labeled peptides were purchased form Cell Signaling Technologies as listed in FIG. 2M.

Trypsin Digestion and Sample Preparations

In-gel trypsin digestion was carried out as described elsewhere (Taelman et al., Cell, 143:1136-1148 (2010)) with modifications. After the gels were extensively washed with water, gels were excised, diced into 2×2 mm cubes, and de-stained using 1 mL of 50 mM ammonium bicarbonate (AMBC)/50% ACN with agitation for 1 hour. Then, the gels were further washed with 1 mL of 50 mM AMBC/50% ACN for three times. Finally, a 100% ACN wash was performed to ensure complete gel dehydration. Lys-C and trypsin mix solution (20 ng/μL) was prepared on ice by dilution of Trypsin/Lys-C Mix (Promega) using pre-chilled 50 mM AMBC pH 8.0. Trypsin solution was subsequently added to gel pieces at approximately equivalent volume and incubated on ice for 30 minutes. Another 1× gel volume of trypsin solution was added to gel samples, which were then incubated for an additional 1 hour on ice for a total incubation time of 1.5 hours prior to transferring samples to 37° C. for overnight digestion. Digests were quenched and extracted by addition of 50 μL of 50% ACN/0.3% formic acid (FA) for 1 hour by shaking. The digested peptides were recovered into fresh Protein Lobind tubes, and an additional extraction step was performed with 80% ACN/0.3% FA for 30 minutes. The extracted peptides were combined and dried in a speed-vac. The peptides were mixed with 5-50 fmol of ubiquitin AQUA peptides, 1% FA, and 0.01% H$_2$O$_2$ in a total volume of 25 μL and were incubated at 4° C. for overnight to oxidize Met.

Liquid Chromatography and Mass Spectrometry

Samples were loaded via partial loop injection directly onto a home-packed 75 μm×200 mm Luna C18 column (Emitter from New Objective, Woburn, Mass.; Luna C18 particles from Phenomenex, Torrance, Calif.) and separated by reverse phase chromatography where solvent A was 100% H$_2$O and 0.1% FA, and solvent B was 100% CAN and 0.1% FA. A 46-minute linear gradient was used (0 minute, 2% B, flow rate 1 µL/minute; 5 minute, 2% B, flow rate 1 µL/minute; 6 minute, 2% B, flow rate 0.3 µL/minute; 36 min, 42% B, flow rate 0.3 µL/minute; 37 minute, 90% B, flow rate 1 µL/minute; 40 min, 90% B, 1 µL/minute; 41 minute, 2% B, flow rate 1 µL/minute; 46 minute, 2% B, flow rate 1 µL/minute). The Thermo Fusion was operated in a scanning mode followed by targeted MS/MS mode, using Xcalibur software. For scanning mode, the orbitrap resolution was 15,000; scan range was 300-1500 m/z; AGC target was 2×10$^5$; maximum injection time was 100 ms. For targeted mode, the isolation window was 2 m/z; activation type was HCD with a collision energy of 28%; orbitrap resolution was 30,000; scan range was 300-1500 m/z; AGC target was 5×10$^4$; maximum injection time was 120 ms. Raw files were searched, and fragment ions quantified using Skyline (MacLean et al., *Bioinformatics*, 26:966-968 (2010)). The fragment ions used for quantitation were listed in FIG. 2M. Data generated from Skyline was exported into a Microsoft Excel spread sheet for further analysis (Kirkpatrick et al., *Nat. Cell Biol.*, 8:896-896 (2006)).

Results

Figure 3:
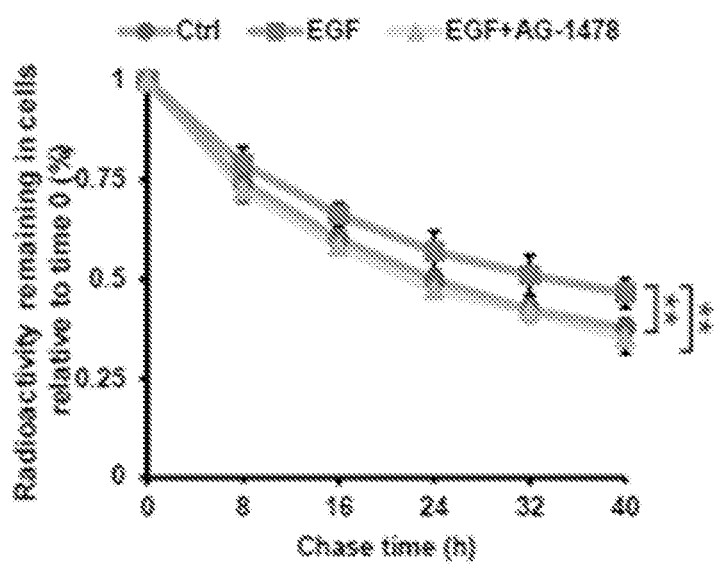
FIG. 3. EGFR enhances proteasomal degradation and promotes K48-linked ubiquitin conjugates. (A). MDA-MB-468 cells were serum starved for 24 hours and labeled with $^{35}$S-Met for 24 hours. After switching to medium containing 2 mM nonradioactive Met for 4 hours to allow the degradation of short-lived components, fresh chase medium containing vehicle, EGF, or EGF plus EGFR inhibitor AG1478 was added. The rate of protein degradation was shown as the fraction of radiolabelled protein remaining over time. Data were mean±SD of three independent experiments. (: $p<0.01$, two-way ANOVA test). (B and C). MDA-MB-468 cells were treated as in (A), except that 20 nM bortezomib (B) or 10 μM chloroquine (C) was present in the chase media. Data were mean±SD of three independent experiments. (: $p<0.01$, two-way ANOVA test). (D). MDA-MB- 468 cells were serum starved for 48 hours, then treated with 20 ng EGF and harvested at different times. Total Ub conjugates, K48-linked conjugates, and K63-linked conjugates were determined by Western blot, and their intensities were quantitated and normalized to that of β-actin and then to time 0 in each group. Data were mean±SD of three independent experiments. (: p<0.01, Student's t-test). (E). MDA-MB-468 cells were serum starved for 48 hours and then changed to medium containing vehicle, 20 ng EGF, or 20 ng EGF together with EGFR inhibitor AG-1478. Total Ub conjugates, K48-linked conjugates, and K63-linked conjugates were determined by Western blot, and their intensities were quantitated and normalized to that of β-actin and then to control in each group. Data were mean±SD of three independent experiments. (: p<0.01, Student's t-test). (F). HEK293 cells were transfected with empty vector (Ctrl) or constitutively-active EGFR (encoding the T790M/L858R mutation) and treated with AG-1478. Total Ub conjugates, K48-linked conjugates, and K63-linked conjugates were determined by Western blot, and their intensities were quantitated and normalized to that of β-actin and then to time 0 in each group. Data were mean±SD of three independent experiments. (**: p<0.01, Student's t-test).
Figure 3:
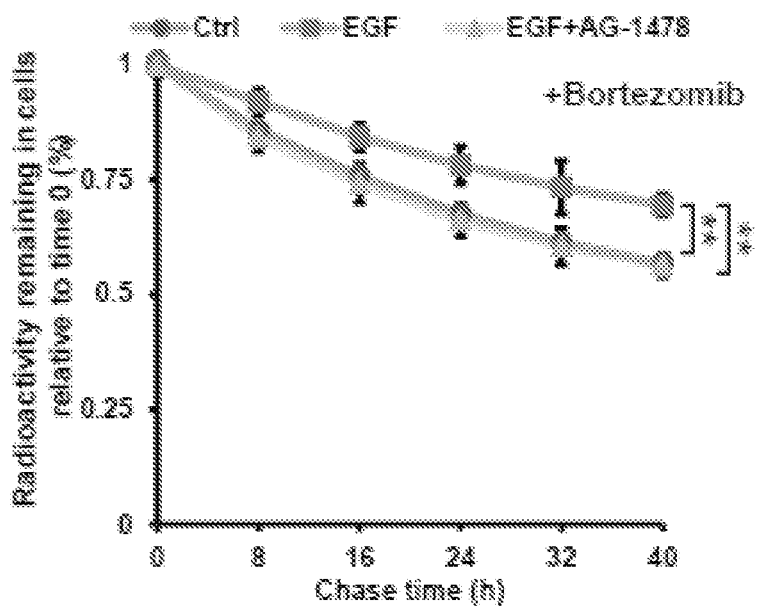
Figure 3:
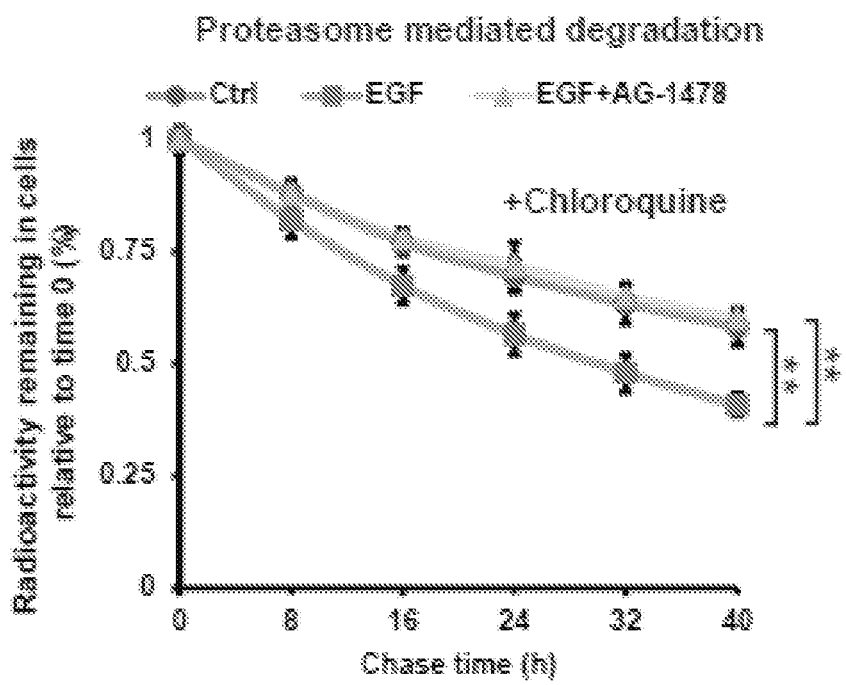
Figure 3:
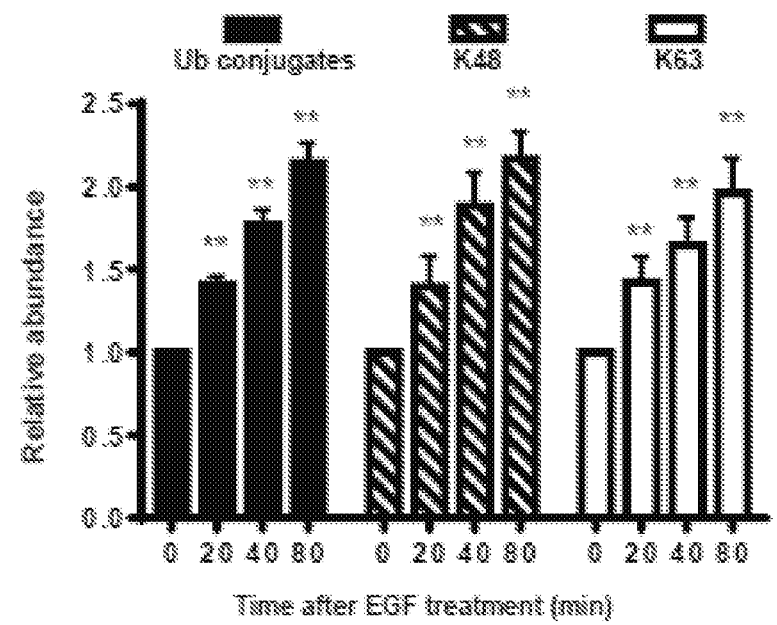
Figure 3:
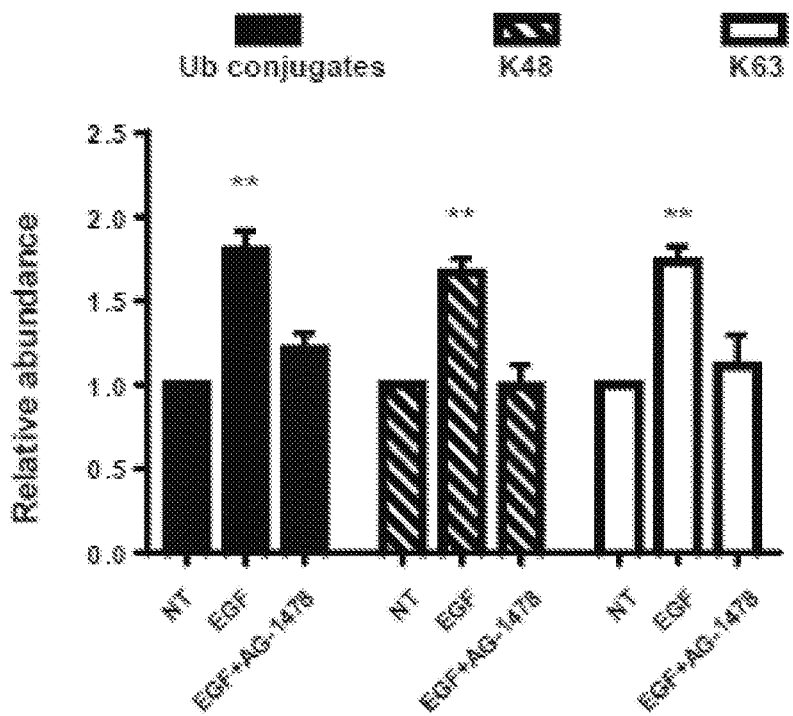
Figure 3:
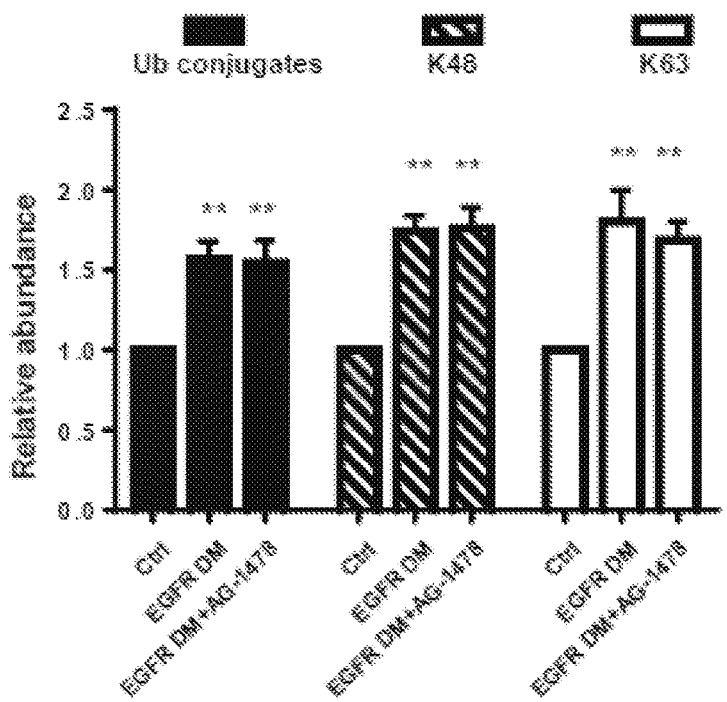

To evaluate whether EGFR activation regulates protein degradation, a human breast cancer cell line, MDA-MB-468, which highly expresses EGFR, was used. To analyze relative protein degradation rate, the percentage of total labelled proteins remaining over time was measured in a pulse-chase experiment (FIG. 2A) as described elsewhere (Taelman et al., *Cell*, 143:1136-1148 (2010)). EGF itself or an EGFR inhibitor, AG-1478, was included in the chase medium to activate or inhibit EGFR. As shown in FIG. 3A, cells treated with EGF displayed an AG-1478-sensitive decrease in the rate of protein degradation, consistent with results described elsewhere (Polet et al., *Biochim. Biophys. Acta*, 1013:279-286 (1989); and Gulve et al., *Biochem. J.*, 260:377-387 (1989)). Eukaryotic cells degrade proteins by both the autophagy-lysosome system and the ubiquitin proteasome system (UPS; Nedelsky et al., *Bba-Mol. Basis Dis.*, 1782:691-699 (2008)). The effects of EGF on the degradation mediated by proteasomes or lysosomes were measured by analyzing the fraction of overall proteolysis sensitive to the proteasome inhibitor, bortezomib, or to the inhibitor of lysosomal acidification, chloroquine, as described elsewhere (Zhao et al., *Cell Metab.*, 6:472-483 (2007)). The lysosome-dependent degradation (in the presence of bortezomib) was inhibited by EGF treatment (FIG. 3B), probably due to phosphorylation of Beclin1 by EGFR (Wei et al., *Cell*, 154:1269-1284 (2013)). Surprisingly, in contrast to the inhibited lysosome-dependent degradation, the proteasome-mediated proteolysis (in the presence of chloroquine) increased dramatically after EGF treatment, and this effect could be blocked by AG-1478 (FIG. 3C), indicating that EGFR signaling enhanced proteasomal degradation. The 26S proteasome recognizes the ubiquitin conjugates on protein and mediates their degradation (Lecker et al., *J. Am. Soc. Nephrol.*, 17:1807-1819 (2006)). To determine the mechanism of increase in proteasomal degradation downstream of EGFR, cellular ubiquitin conjugates were evaluated. Cells treated with EGF possessed significantly higher cellular ubiquitin conjugates in a time dependent manner (FIG. 3D and FIG. 2B). Different Ub chains are formed through isopeptide linkages between the C-terminal glycine of Ub and one of the lysines on the preceding Ub. K48-linked Ub chains are predominant for targeting proteins to 26S proteasomes (Nathan et al., *Embo Journal*, 32:552-565 (2013)). Using antibodies specific for K48 and K63 ubiquitin linkage, EGF was found to increase the overall cellular content of K48-linked Ub chains as well as K63-linked Ub chains (FIG. 3D and FIG. 2C-D). The EGF-induced increase of Ub conjugates as well as K48-linked Ub chains were sensitive to AG-1478 (FIG. 3E and FIG. 2E-G), indicating that this effect on Ub chain assembly was dependent on EGFR activity. Similar increases in Ub conjugate levels were seen in HEK293 cells expressing constitutively-active EGFR mutant (T790M/L858R) (FIG. 3F and FIG. 2H-J). As T790M/L858R (double mutant, DM) is resistant to AG-147820, the increases in Ub conjugate level of HEK293 cells expressing EGFR T790M/L858R mutant were not sensitive to AG-1478 (FIG. 3F and FIG. 2H-J). The enhancement of K48-linked Ub chain by EGFR activation was further confirmed quantitatively using Ub-AQUA (FIGS. 2K and 2L). Interestingly, EGFR activation also upregulated other types of Ub chain such as K63, K11, K33, K29, and linear Ub chain. The K48 chain was studied due to its important role in protein degradation.

Given that EGFR itself can be ubiquitinated and degraded following EGF treatment, whether the enhancement of Ub conjugates and proteasomal degradation is due to ubiquitination and degradation of EGFR itself was tested. Use of an EGFR Y1045F mutant (Ettenberg et al., *J. Biol. Chem.*, 276:27677-27684 (2001); and Levkowitz et al., *Mol. Cell*, 4:1029-1040 (1999)), which cannot be ubiquitinated or degraded after EGF treatment was employed. As shown in FIGS. 4A-E, in cells expressing either wild type EGFR or the EGFR Y1045F mutant, EGF induced similar levels of ubiquitin conjugates and proteasomal degradation, indicating that EGFR enhanced global cellular Ub conjugation independent of ubiquitination of EGFR itself.

Figure 4:
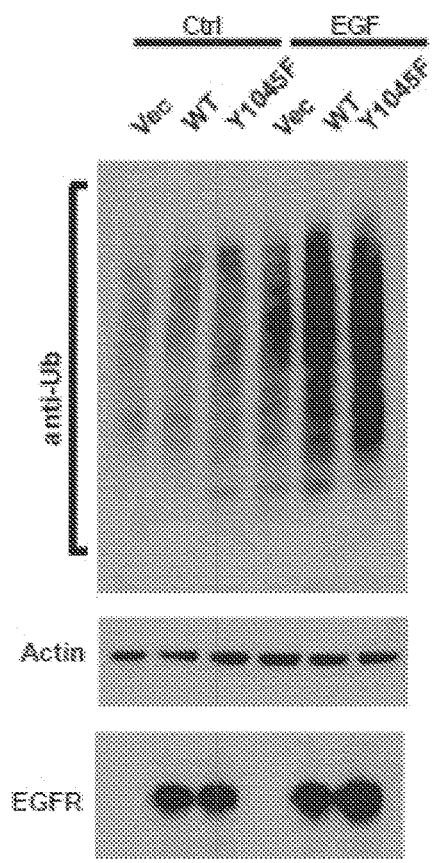
FIG. 4. EGF treatment raises the cellular content of Ub conjugates independent of EGFR ubiquitination and new protein synthesis. (A-D). NIH-3T3 stably expressing empty vector (Ctrl), wide type EGFR, or EGFR Y1045F mutant were serum starved for 48 hours and treated with or without 20 ng/mL EGF for 1 hour. Total Ub conjugates (A), K48-linked conjugates (B), and K63-linked conjugates were determined by Western Blot, and their intensities were quantitated and normalized to that of β-actin and then to control at time 0 in each group (D). Data were mean±SD of three independent experiments. (: p<0.01, Student's t-test). (E). NIH-3T3 stably expressing empty vector (Ctrl), wide type EGFR, or EGFR Y1045F mutant were serum starved for 48 hours and were labeled with $^{35}$S Met for 24 hours in the absence of serum. After switching to chase medium for 4 hours to allow the degradation of short-lived components, fresh chase medium containing vehicle or EGF was added in the present of 10 μM chloroquine. At different time points, cells were harvested, and radiolabeled protein remaining in the cell was measured. The rate of protein degradation was shown as the fraction of radiolabelled protein remaining over time. Data were mean±SD of three independent experiments. (: p<0.01, two-way ANOVA test). (F). Schematic diagram of the experimental design for the pulse-chase measurements of protein degradation within cycloheximide (CHX). MDA-MB-468 cells were serum starved for 24 hours and labeled with $^{35}$S-Met for 24 hours. After switching to medium containing 2 mM nonradioactive Met for 4 hours to allow the degradation of short-lived components, fresh chase medium containing 100 μg/mL CHX was added. After treatment with 100 μg/mL CHX for 1 hour, 20 ng/mL EGF and chloroquine were added. The rate of protein degradation was shown as the fraction of radiolabelled protein remaining over time. (G). Cells were treated as illustrated in (A), and the radioactivity of remaining in cells was measured. Data were mean±SD of three independent experiments (: p<0.01, by two-way ANOVA). (H and I). MDA-MB-468 cells were serum starved for 48 hours and then treated with 100 μg/mL cycloheximide for 1 hour, and 20 ng/mL EGF or vehicle was then added for 2 hours. The levels of Ub conjugates and β-actin were determined by Western blot (C) and quantitated (D). Data were mean±SD of three independent experiments. (: p<0.01, Student's t-test).
Figure 4:
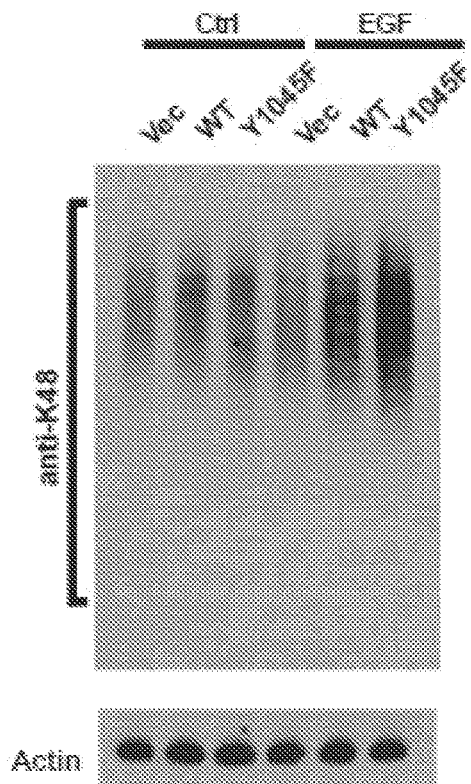
Figure 4:
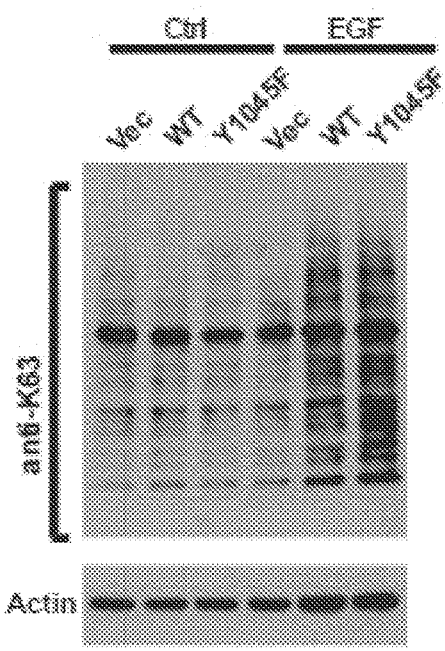
Figure 4:
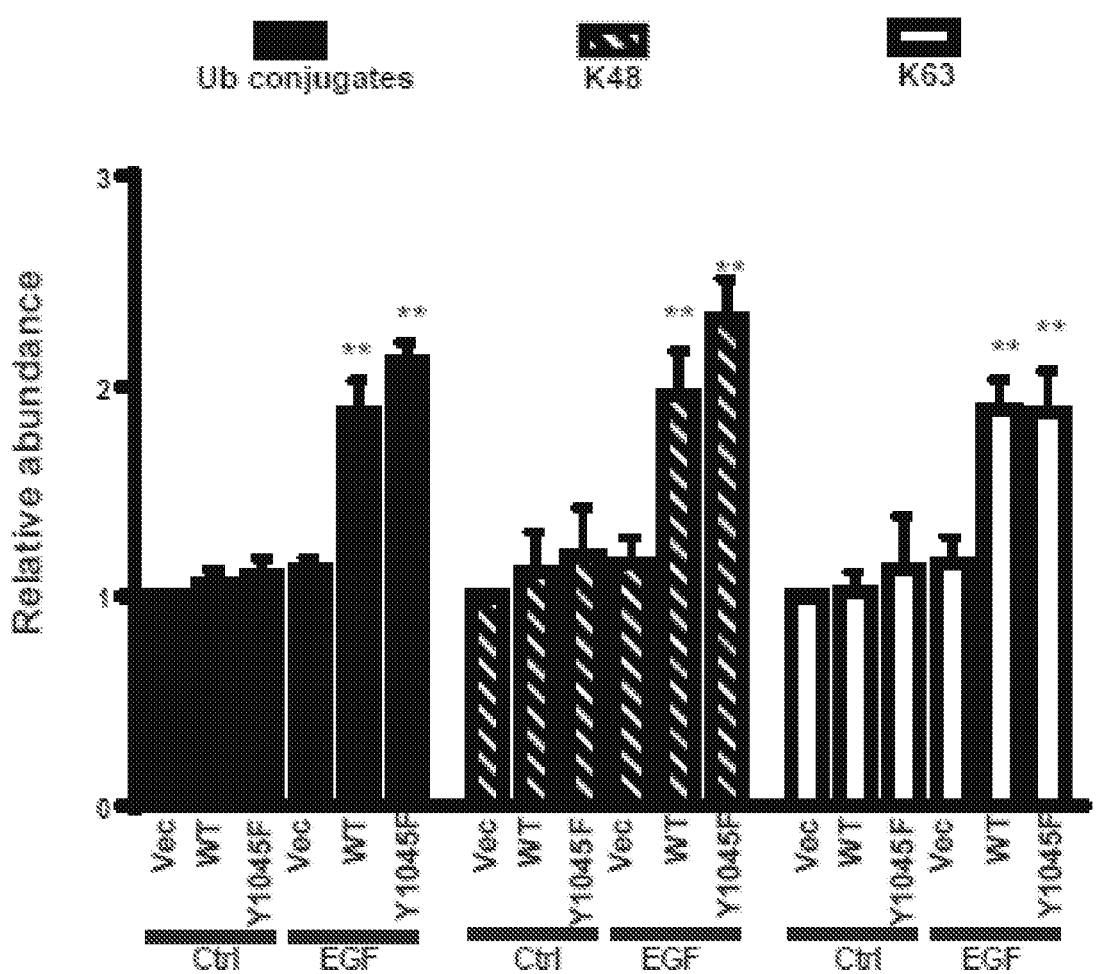
Figure 4:
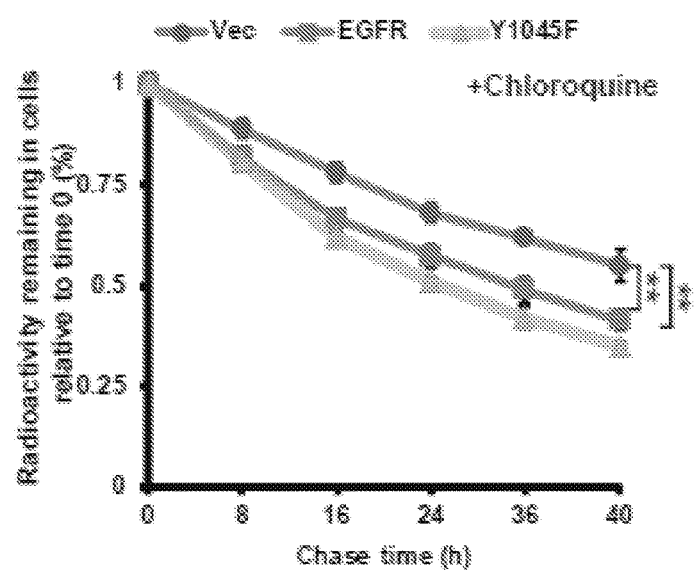
Figure 4:
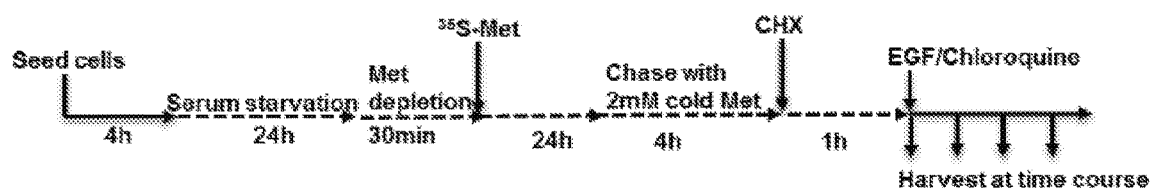
Figure 4:
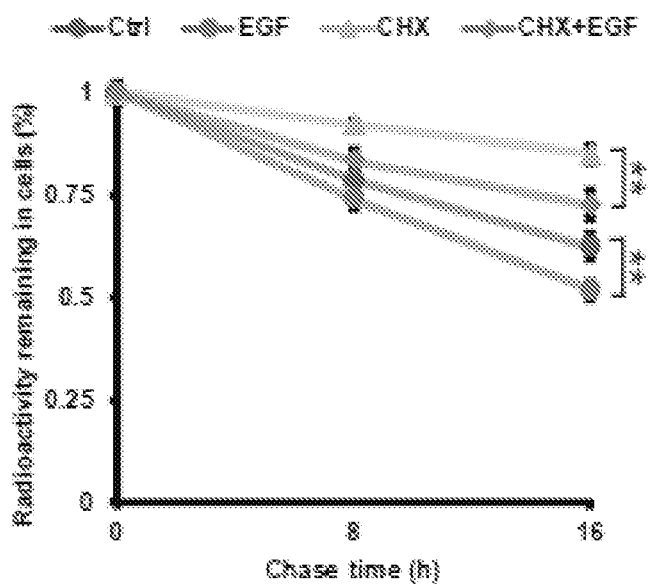
Figure 4:
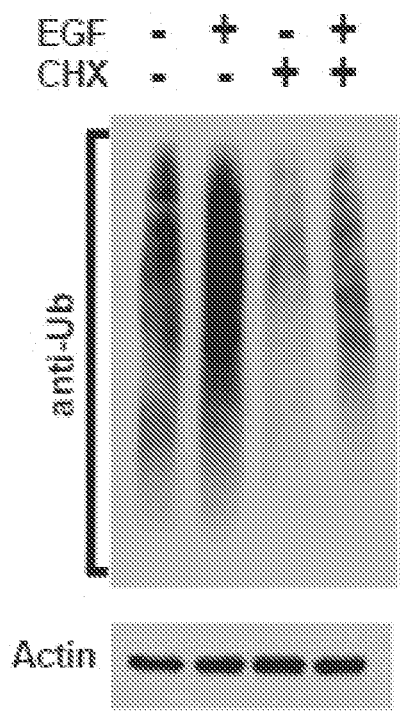
Figure 4:
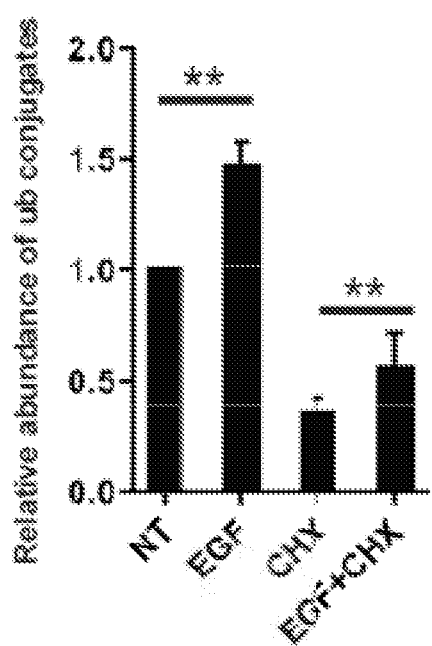

To learn whether the enhancement in proteasomal degradation and Ub conjugate level by EGF treatment is dependent on newly synthesized protein, cells were pretreated with cycloheximide for 1 hour before EGF treatment (FIG. 4F). Although cycloheximide by itself reduced proteasomal proteolysis, EGF caused a similar or greater increase in proteasomal proteolysis (FIG. 4G) as well as Ub conjugation level (FIGS. 4H and 4I). Thus, this rapid stimulation of Ub chain assembly by EGF did not require new protein synthesis.

Figure 5:
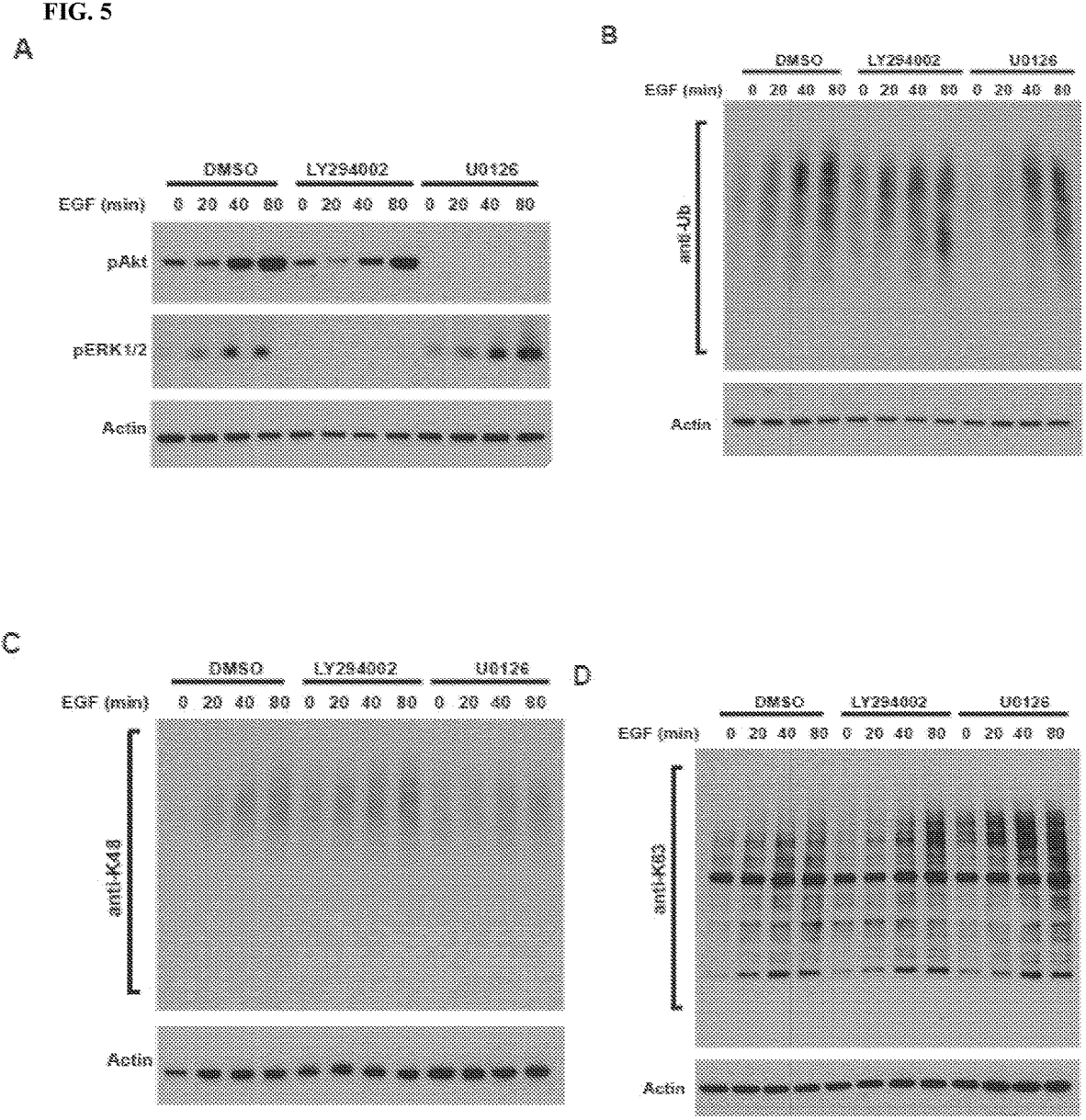
FIG. 5. PI3K and MEK inhibitors do not block the effect of EGF on cellular ubiquitin conjugates and ubiquitin phosphorylation. (A). MDA-MB-468 cells were serum starved for 36 hours, pretreated with PI3K inhibitor LY294002 or MEK inhibitor U0126 for 12 hours, then treated with 20 ng EGF, and harvested at different times. Cell lysates were extracted and blotted with the indicated antibodies. (B-E). MDA-MB-468 cells were serum starved for 36 hours, pretreated with PI3K inhibitor LY294002 or MEK inhibitor U0126 for 12 hours, then treated with 20 ng EGF, and harvested at different times. Total Ub conjugates (B), K48-linked conjugates (C), and K63-linked conjugates (D) were determined by Western blot, and their intensities were quantitated and normalized to that of β-actin and then to control at time 0 in each group (E). Data were mean±SD of three independent experiments (**: p<0.01, Student's t-test).
Figure 5:
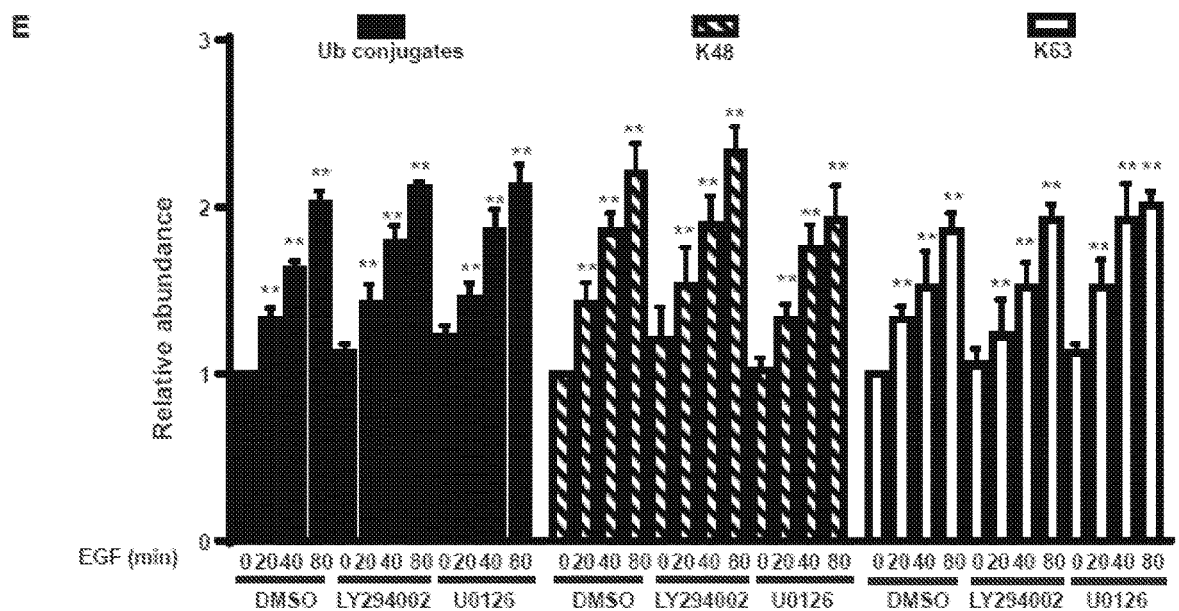
Figure 6:
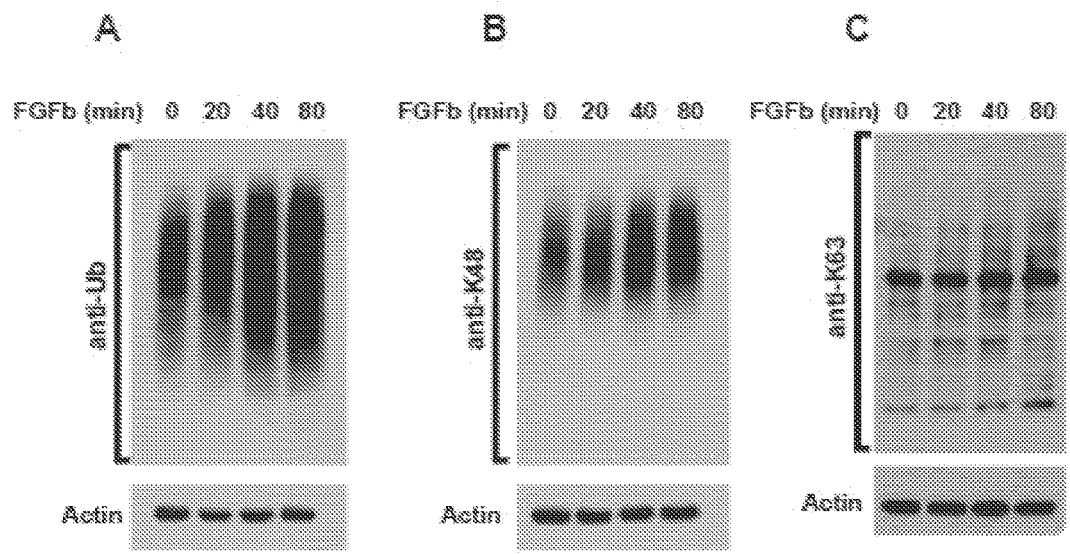
FIG. 6. FGFR activation increases cellular Ub conjugates. (A to D). NIH-3T3 cells were serum starved for 48 hours and then treated with 20 ng/mL FGFb and harvested at different time course. Total Ub conjugates (A), K48-linked conjugates (B), and K63-linked conjugates (C) were determined by Western blot, and their intensities were quantitated and normalized to that of β-actin and then to time 0 in each group (D). Data were mean±SD of three independent experiments. (: p<0.01, Student's t-test). (E to H). HEK293 cells were transfected with empty vector (Ctrl), FGFR2 wide type, or FGFR2 kinase dead mutant (KR). Total Ub conjugates (E), K48-linked conjugates (F), and K63-linked conjugates (G) were determined by Western blot, and their intensities were quantitated and normalized to that of β-actin and then to control in each group (H). Data were mean±SD of three independent experiments. (: p<0.01, Student's t-test). (I to L). NIH-3T3 cells were serum starved for 48 hours and then treated with vehicle, FGFb, or FGFb and FGF inhibitor TKI-258. Total Ub conjugates (I), K48-linked conjugates (J), and K63-linked conjugates (K) were determined by Western blot, and their intensities were quantitated and normalized to that of β-actin and then to control in each group (L). Data were mean±SD of three independent experiments. (**: p<0.01, Student's t-test).
Figure 6:
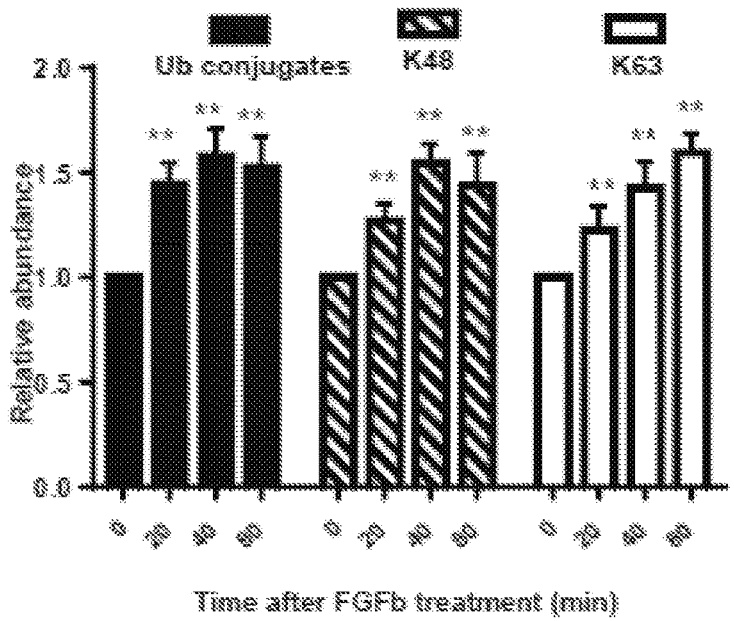
Figure 6:
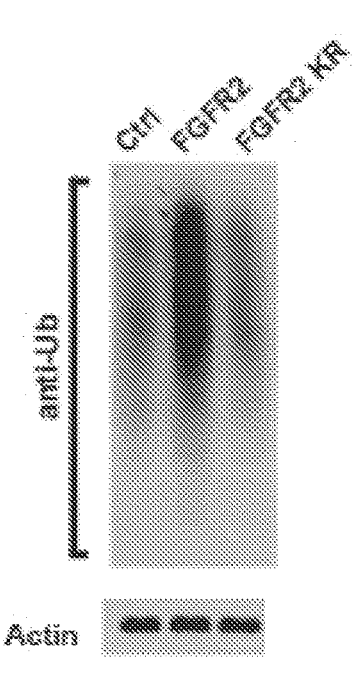
Figure 6:
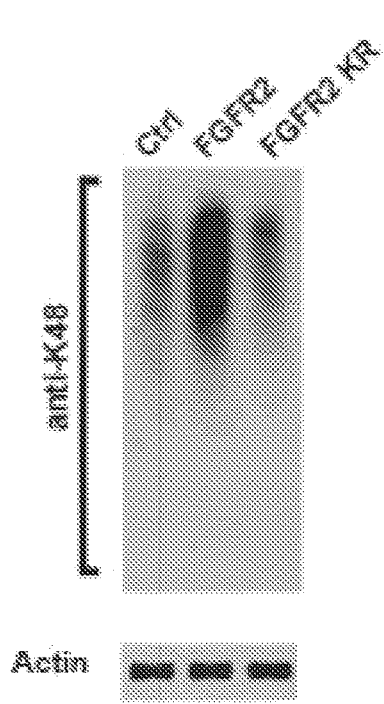
Figure 6:
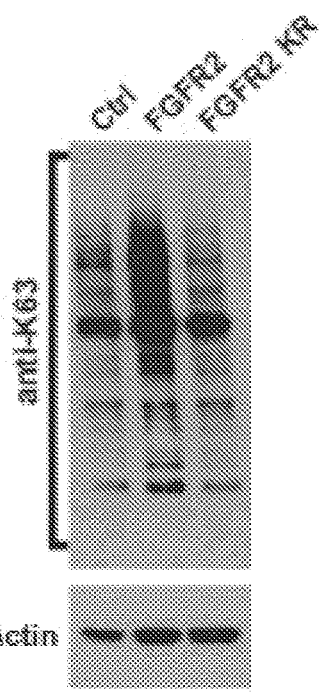
Figure 6:
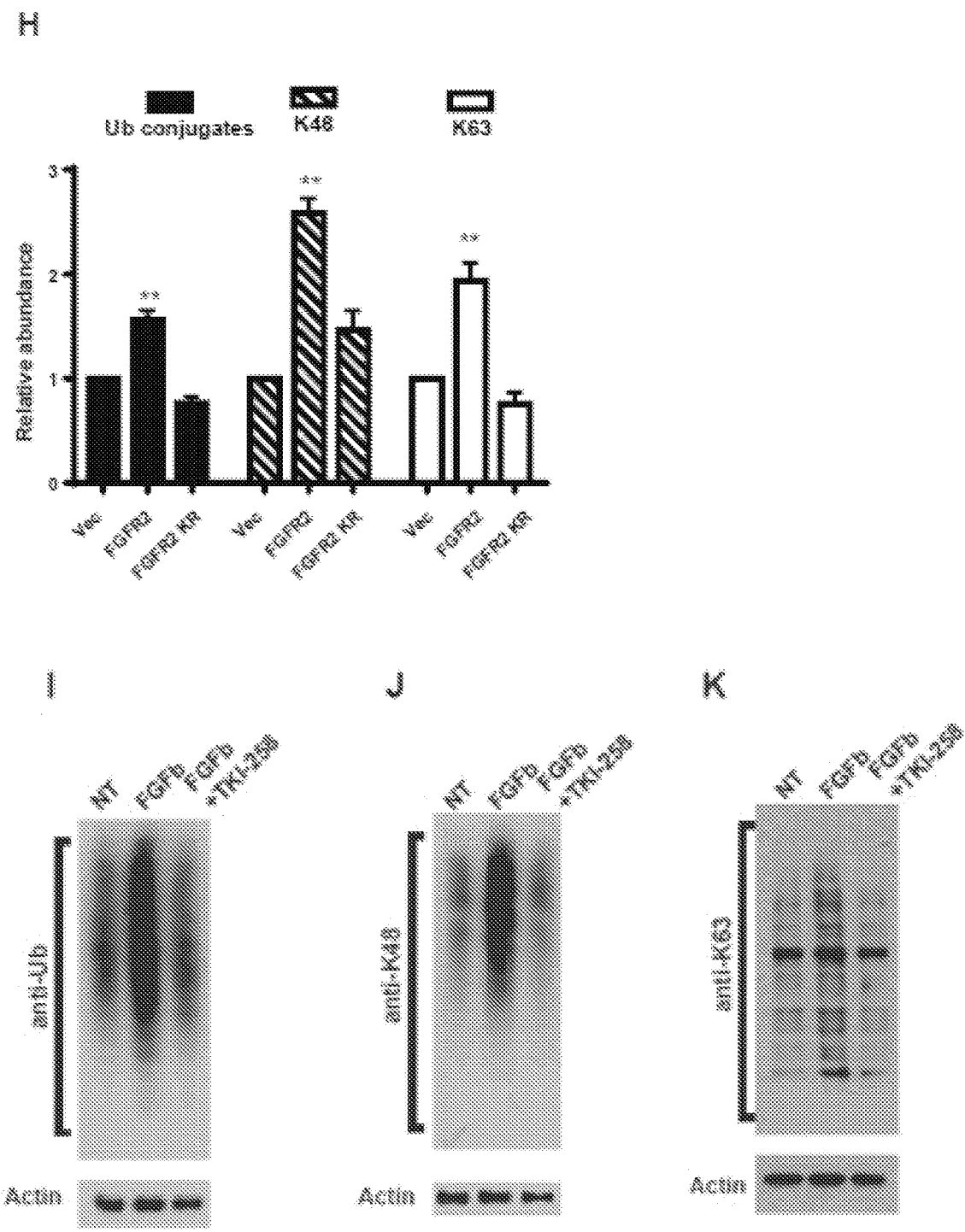
Figure 6:
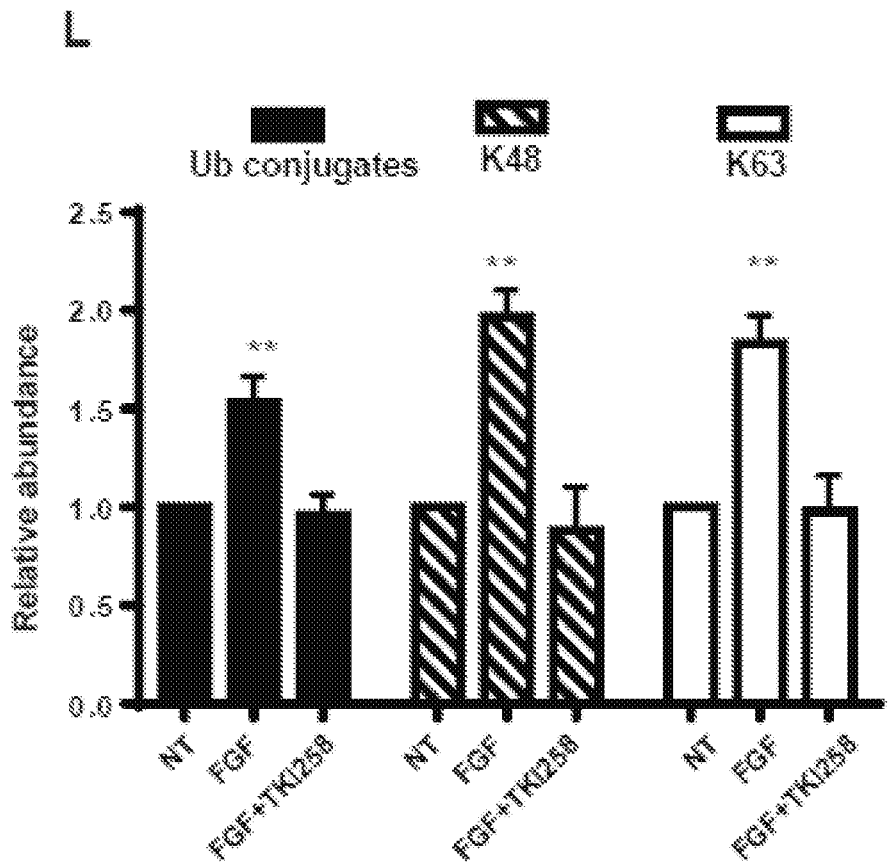

To study whether the enhancement of Ub conjugate level by EGF treatment was dependent on EGFR downstream effectors such as PI3K and MEK, the cells were pretreated with PI3K inhibitor LY294002 or MEK inhibitor U0126 for 12 hours before EGF treatment (FIG. 5A). As shown in FIGS. 5B-E, inhibitors of PI3K or MEK did not affect the stimulation of Ub chain assembly by EGF, indicating that this enhancement of Ub conjugate level was independent of PI3K or MEK pathway.

To test whether other receptor tyrosine kinases (RTKs) could also increase Ub conjugates, a mouse fibroblast cell line, NIH-3T3, that expresses FGFR1 and FGFR2 was used. Addition of FGFb for 20 minutes resulted in a highly reproducible 50% increase in the total content of ubiquitinated proteins as well as K48-linked Ub conjugates (FIGS. 6A-D). This increase in Ub conjugates was maximal after only a 40-minute treatment (FIGS. 6A-D). Similar increases in Ub conjugate levels were observed in HEK293 cells expressing wild type FGFR2 but not the kinase dead mutant (KR) (FIGS. 6E-H). The increase in Ub conjugates induced by FGFb was dependent on FGFR activation as this effect was blocked by FGFR inhibitor TKI-258 (FIGS. 6I-L). These results indicated, similar to EGFR signaling, FGFR signaling also induced overall K48-linked ubiquitin chain assembly.

Figure 7:
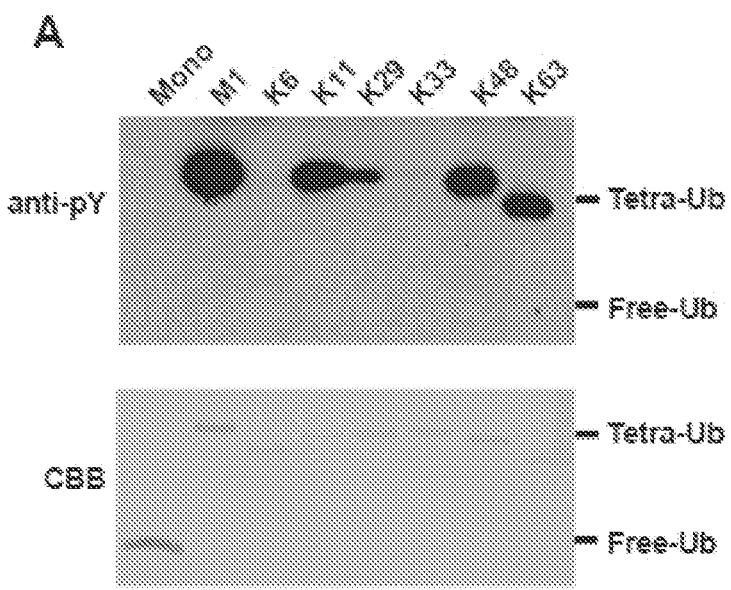
FIG. 7. EGFR phosphorylates ubiquitin. (A). An in vitro kinase assay was performed at 30° C. for 1 hour in the presence of EGFR and different tetra-Ub chain or free Ub. The gels were subjected to western blot with anti-phosphortyrosine antibody (upper panel) or Coomassie brilliant blue (CBB) staining (lower panel). (B). Lysates from EGF treated cells was trypsinized and subjected to liquid chromatography tandem mass spectrometry (LC-MS/MS) analysis. (C). MDA-MB-468 cells were serum starved for 48 hours and then incubated in medium containing vehicle or 20 ng EGF for 80 min. Absolute quantification of TLSDYNIQKESTLHLVLR and TLSD(pY)NIQKESTLHLVLR from control of EGF treated cells were quantified by Parallel Reaction Monitoring. Data were mean±SD of three independent experiments. (**: p<0.01, Student's t-test). (D) MDA-MB-468 cells were serum starved for 48 hours and then incubated in medium containing 20 ng EGF for different times. Cell lysates were blotted with the anti-pY59 antibody. (E). MDA-MB-468 cells were serum starved for 48 hours and then incubated in medium containing vehicle, 20 ng EGF, or 20 ng EGF and 100 μM AG-1478. Cell lysates were blotted with antibodies against pY59 and β-actin. (F). WT Ub- and Ub Y59F-replacement cells were serum starved and induced with DOX for 72 hours to replace endogenous Ub with WT Ub or Ub Y59F. Cells were then treated with 20 ng EGF and harvested at different time points. Cell lysates were blotted with antibodies against pY59 and β-actin.
Figure 7:
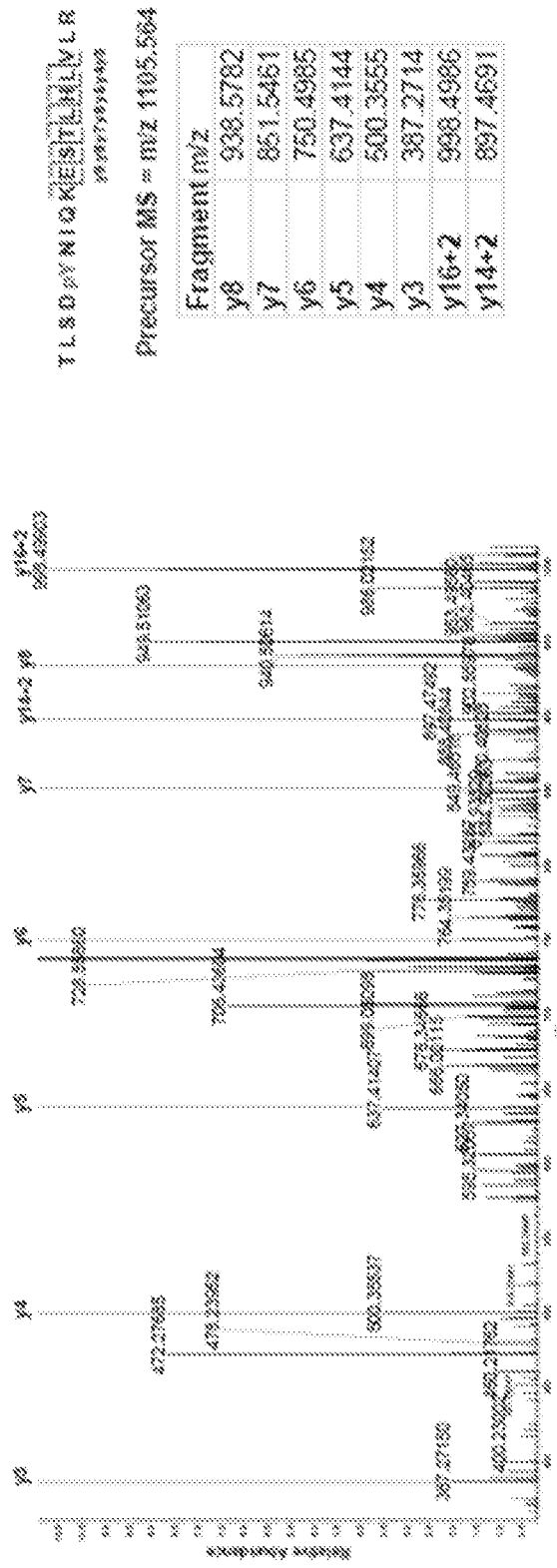
Figure 7:
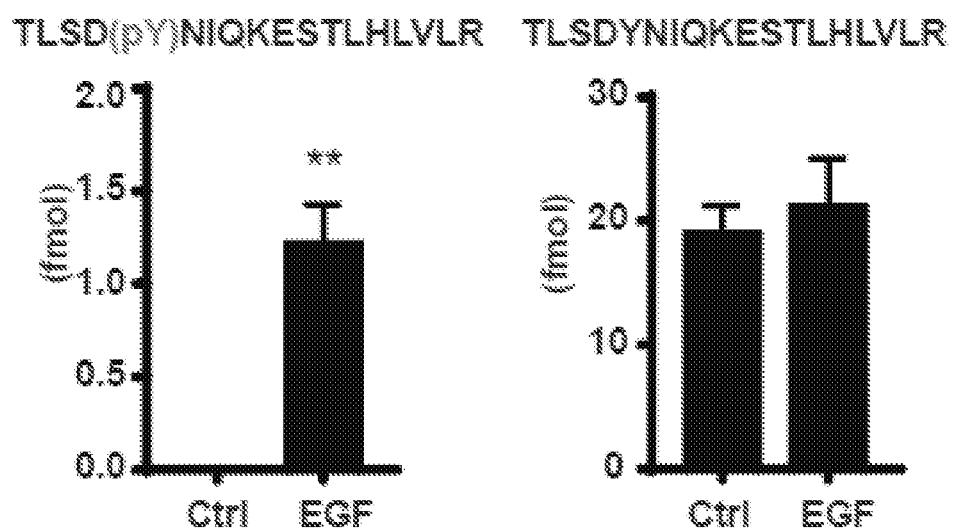
Figure 7:
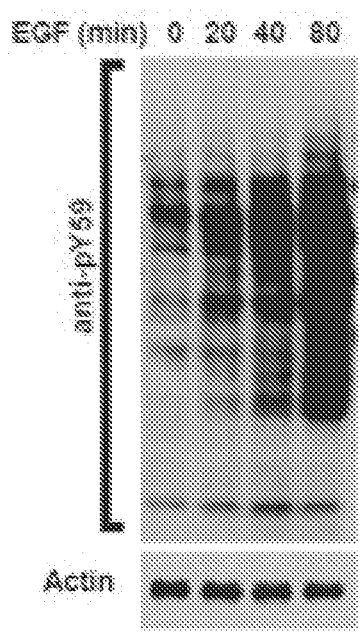
Figure 7:
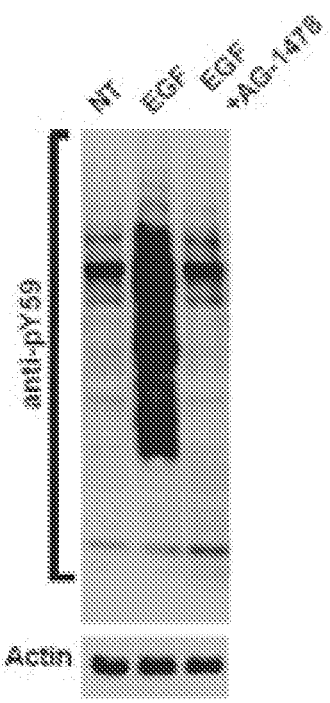
Figure 7:
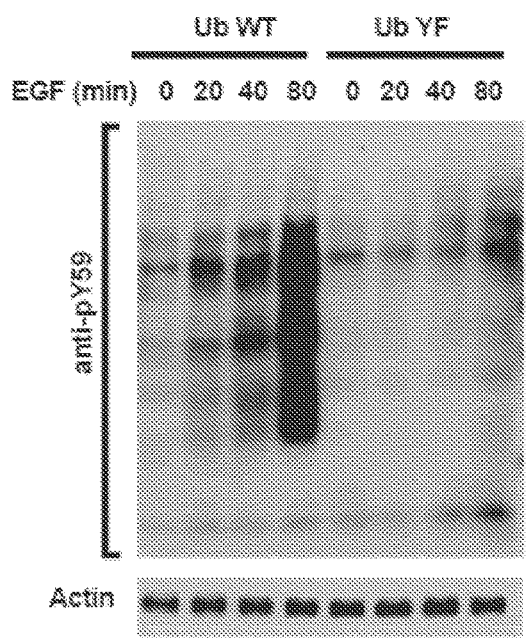

Given that both EGFR and FGFR are receptor tyrosine kinases and ubiquitin can be phosphorylated at Tyr 59 (Y59) (Hornbeck et al., *Nucleic Acids Res.*, 43:D512-D520 (2015); and Schweppe et al., *J. Proteomics*, 91:286-296 (2013)), it was speculated that one possibility was that these receptor tyrosine kinases could phosphorylate ubiquitin and thus affect ubiquitin chain assembly. Mono-Ub could be hardly phosphorylated by EGFR. With a panel of different tetra-Ub chain, EGFR also was fond to phosphorylate tetra Ub chains (Ub4) such as Ml, K11, K29, K33, K48, and K63 (FIG. 7A). To determine the phosphorylation of Ub in cells, lysates from EGF treated cells were trypsinized and subjected to liquid chromatography tandem mass spectrometry (LC-MS/MS) analysis. The 55-72 pY59 were identified with high confidence, suggesting Y59 phosphorylation (FIG. 7B). Next, the absolute levels of phosphorylated ubiquitin in EGF treated cell lysates were determined using absolute quantification (AQUA) peptides as standards (FIG. 2M). The non-phosphorylated 55-72 peptide derived from endogenous ubiquitin were detected both in treated and untreated cells, whereas the 55-72 pY59 phosphopeptide was only detected in EGF treated cells (FIGS. 7C-D). 5% of the 55-72 peptide was phosphorylated after EGF treatment (FIG. 7C), indicating a significant pool of ubiquitin was phosphorylated.

Figure 8:
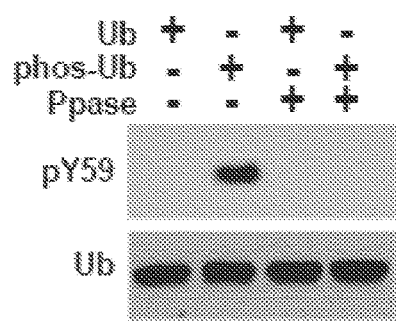
FIG. 8. EGFR activation regulates phosphorylation of Ubiquitin. (A). Synthesized biotin-Ahx-ubiquitin Ub and biotin-Ahx-ubiquitin Ub pY59 were treated with or without Lambda Protein Phosphatase and blotted with anti-Ub and anti-pY59 antibodies. (B). Lysates of MDA-MB-468 cells treated with EGF were treated with indicated PPase or USP2cc at 37° C. for 1 hour. The lysates were blotted with anti-Ub and anti-pY59 antibodies. (C and D). MDA-MB-468 cells were treated with vehicle or EGF and fixed with 4% paraformaldehyde. Immunofluorescence (C) or Immunohistochemical staining (D) were performed with anti-pY59 antibody or anti-pY59 antibody blocked with indicated peptides. (E). Schematic of the Ub-replacement system used to replace endogenous Ub with Ub Y59F. (F) Validation of Ub-replacement cells. The indicated cells were serum starved and DOX induced for 72 hours. The levels of HA-Ub and Ub were measured by immunoblotting. Actin was used as a loading control. (G). NIH-3T3 stably expressing empty vector (Ctrl), wide type EGFR, or the EGFR Y1045F mutant were serum starved for 48 hours and treated with or without 20 ng/mL EGF for 1 hour. The lysates were blotted with anti-actin and anti-pY59 antibodies. (H). MDA-MB-468 cells were serum starved for 36 hours, pretreated with PI3K inhibitor LY294002 or MEK inhibitor U0126 for 12 hours, then treated with 20 ng EGF, and harvested at different times. Cell lysates were blotted with an anti-pY59 antibody.
Figure 8:
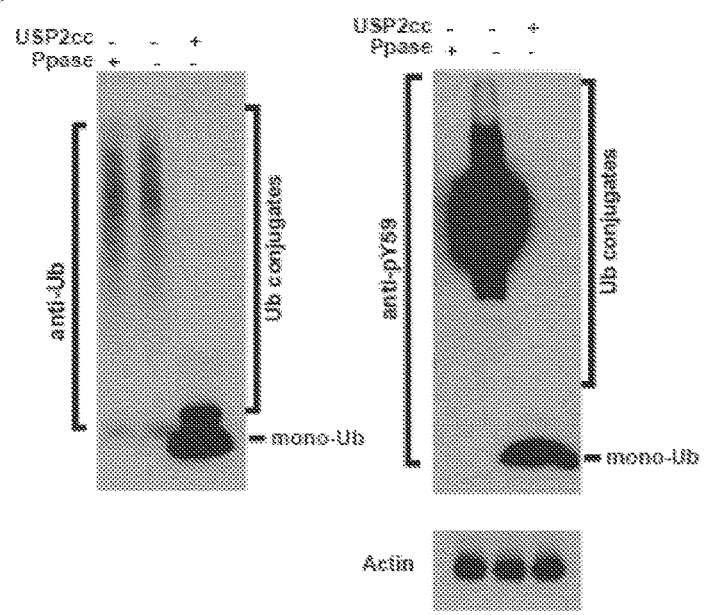
Figure 8:
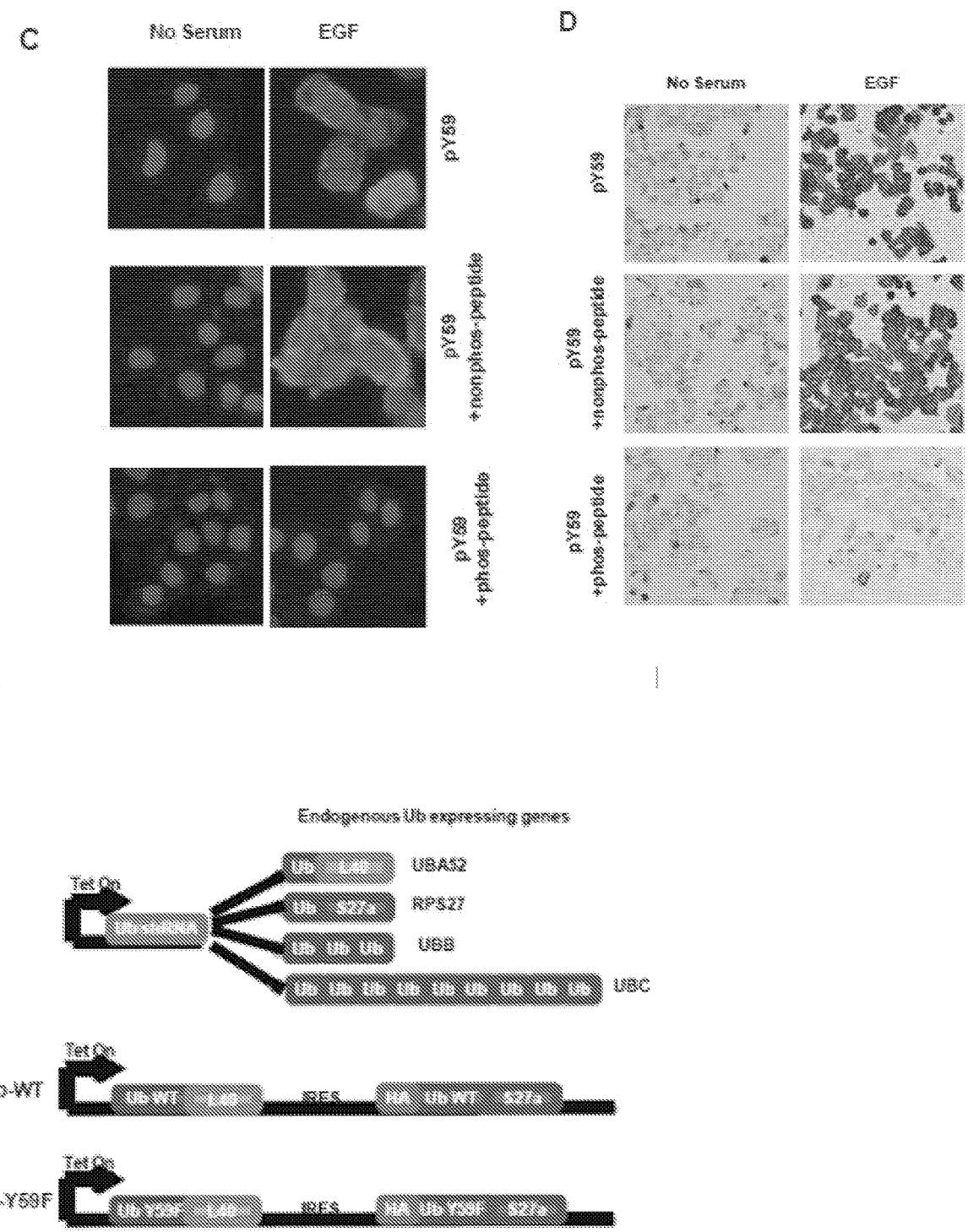
Figure 8:
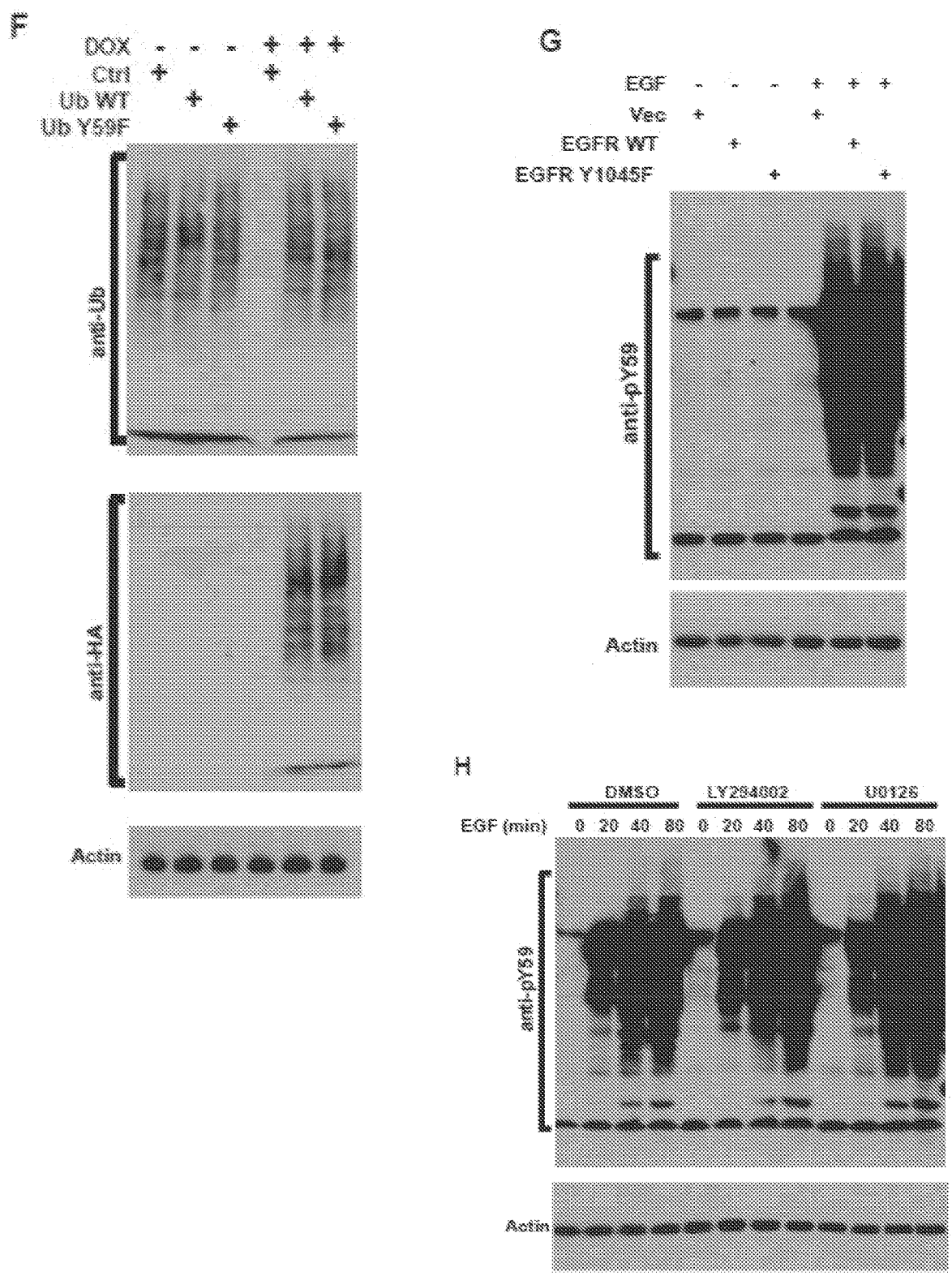

A specific pY59 antibody that only recognizes phosphorylated Ub (FIGS. 8A-D) was generated and used to detect phosphorylation of Ub in cells. EGF treatment induced a dramatic increase in the phosphorylation of Ub in a time dependent manner (FIG. 7D). Furthermore, this increase was blocked by the EGFR inhibitor, AG-1478 (FIG. 7E). To confirm Ub phosphorylation directly in cell, an Ub replacement strategy in MDA-MB-468 cells was used, wherein all endogenous copies of Ub were depleted by doxycycline (DOX)-inducible RNAi while simultaneously expressing shRNA-resistant Ub WT and Ub Y59F fused to the N terminus of ribosomal proteins L40 and S27a from a DOX-responsive promoter (FIG. 8E) (Xu et al., *Mol. Cell*, 36:302-314 (2009)). Immunoblotting of extracts demonstrated similar levels of Ub WT and Ub Y59F proteins after DOX induction for 3 days in the absence of serum (FIG. 8F). In this Ub replacement system, where endogenous Ub was replaced by wild type Ub or the Y59F mutant, EGF induced Ub phosphorylation only in cells expressing wild type Ub, but not Ub Y59F (FIG. 7F), further confirming that EGFR activation led to the phosphorylation of Ub at Y59 in cells. The EGFR Y1045F mutant also induced ubiquitin Y59 phosphorylation at the similar level as wild type EGFR (FIG. 8G), suggesting that Ub phosphorylation induced by EGF was independent of ubiquitin conjugated to EGFR itself. Furthermore, the PI3K or MEK pathway was not required for the phosphorylation of ubiquitin induced by EGFR activation (FIG. 8H), suggesting that EGFR probably phosphorylated ubiquitin directly in cells although other tyrosine kinases may also contribute to the phosphorylation.

Figure 9:
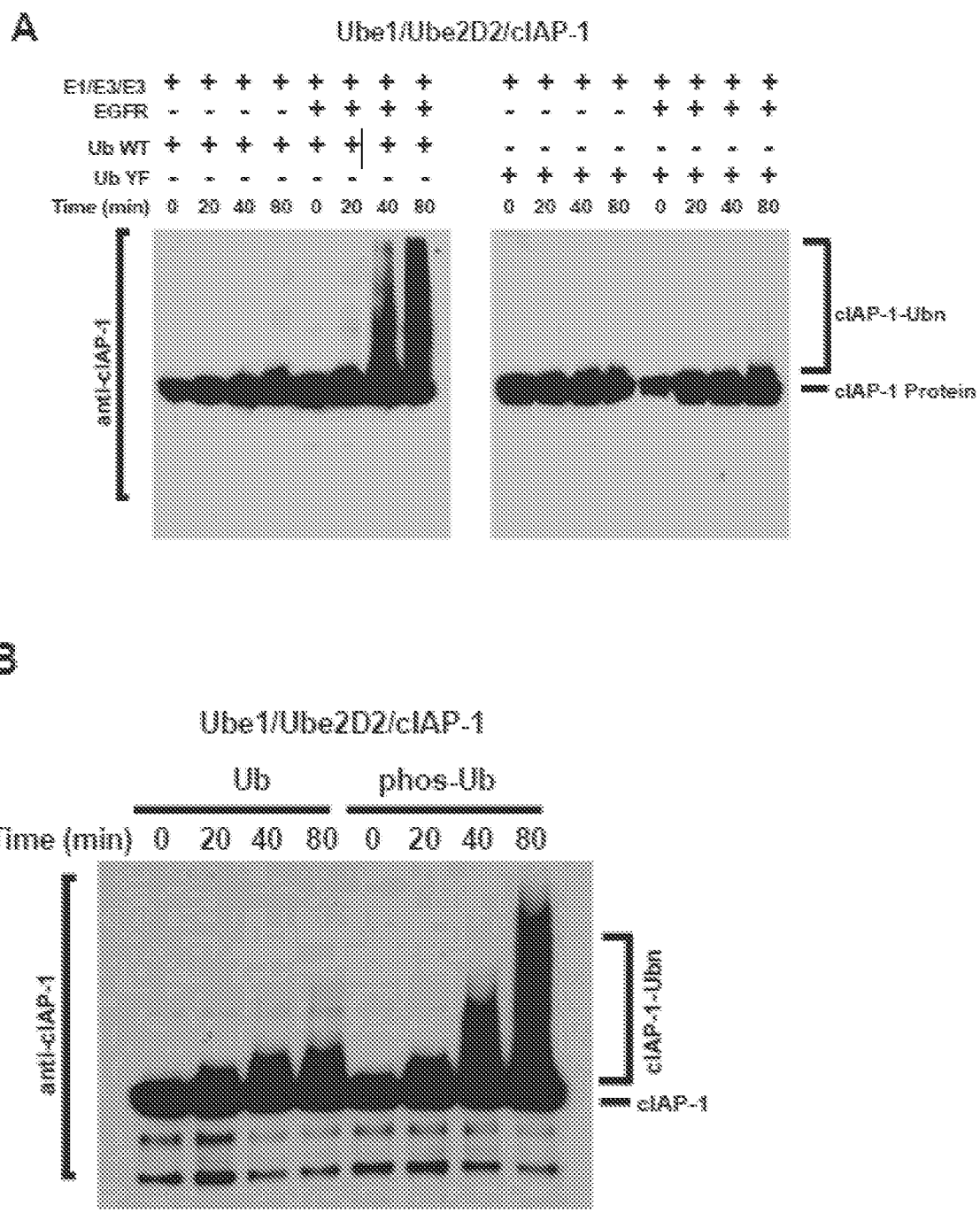
FIG. 9. Phosphorylation of Ub promotes Ub chain assembly. (A). The assembly of ubiquitin chains was determined at 30° C. in the presence of EGFR, Ube1, Ube2g2, gp78, and indicated Ub variants. Samples were taken at the indicated time points, and polyubiquitin chains were detected by immunoblotting with an anti-Ub antibody. (B). The assembly of ubiquitin chains was determined at 30° C. in the presence of Ube1, Ube2D2, cIAP-1, and indicated Ub variants. Samples were taken at the indicated time points, and polyubiquitin chains were detected by immunoblotting with an anti-cIAP-1 antibody. (C). Di-Ub synthesis assay. Reduced SDS-PAGE showing diUb formation over time by Ube2D2. In the upper panel, UbcH5B~biotin-Ahx-Ub or UbcH5B~bioitin-Ahx-phosUb were mixed with Ub (1 mM). In the lower panel, UbcH5B~bioitin-Ub was mixed with Ub or phos-Ub (1 mM). The reactions were quenched at the indicated times with 2×SDS loading buffer containing 500 mM DTT, resolved by SDS-PAGE, and stained with HRP-conjugated streptavidin. (D to E). WT Ub- and Ub Y59F-replacement cells were serum starved and DOX induced for 72 hours to replace endogenous Ub with Ub WT or Ub Y59F and then treated with 20 ng EGF for different times. Total Ub conjugates (D) and K48-linked conjugates (F) were determined by Western blot, and their intensities quantitated and normalized to that of β-actin. Data were mean±SD of three independent experiments. (: $p<0.01$, Student's t-test). (F). WT Ub- and Ub Y59F replacement cells were serum starved and DOX induced for 48 hours to replace endogenous Ub with Ub WT or Ub Y59F and were labeled with $^{35}$S Met for 24 hours in the absence of serum. After switching to chase medium for 4 hours to allow the degradation of short-lived components, fresh chase medium containing vehicle or EGF was added. At different time points, cells were harvested, and radiolabeled protein remaining in the cell was measured. The rate of protein degradation was shown as the fraction of radiolabeled protein remaining over time. Data were mean±SD of three independent experiments. (: $p<0.01$, two-way ANOVA test). (G). WT Ub- and Ub Y59F-replacement cells were serum starved and DOX induced for 72 hours to replace endogenous Ub with Ub WT or Ub Y59F and were changed to medium containing vehicle or EGF for 8 hours. Amino acid levels were shown as mean±SD of three independent experiments (: $p<0.01$, Student's t-test). (H). Rates of protein synthesis in cells treated as in (G) were shown as mean±SD of three independent experiments (: $p<0.01$, Student's t-test).
Figure 9:
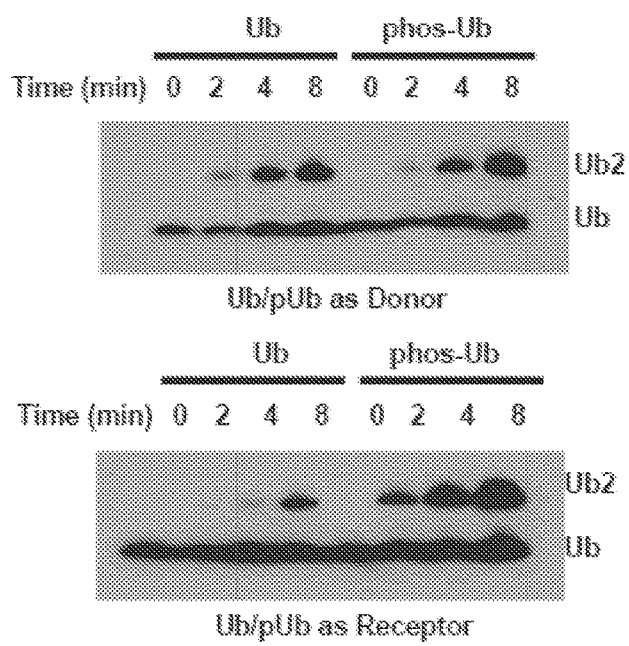
Figure 9:
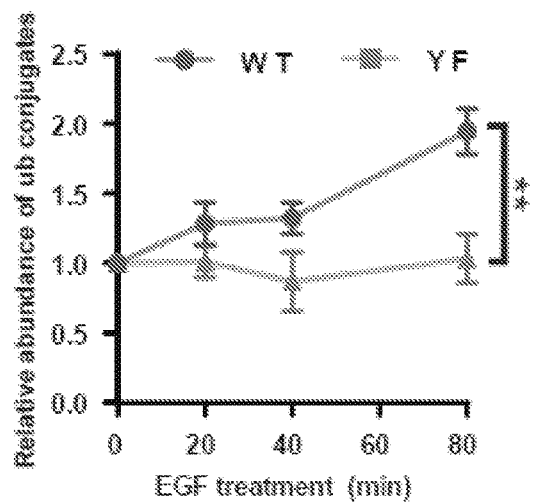
Figure 9:
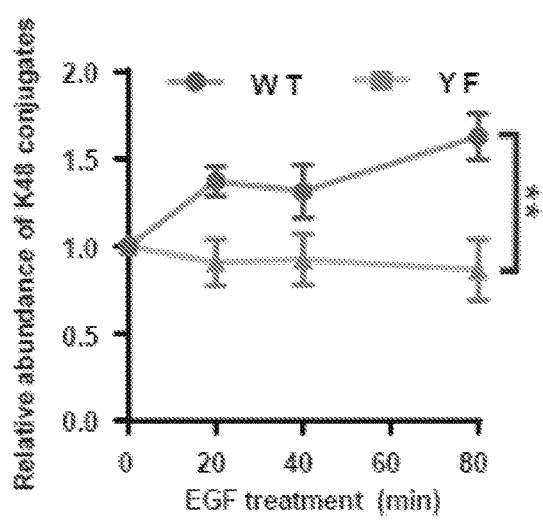
Figure 9:
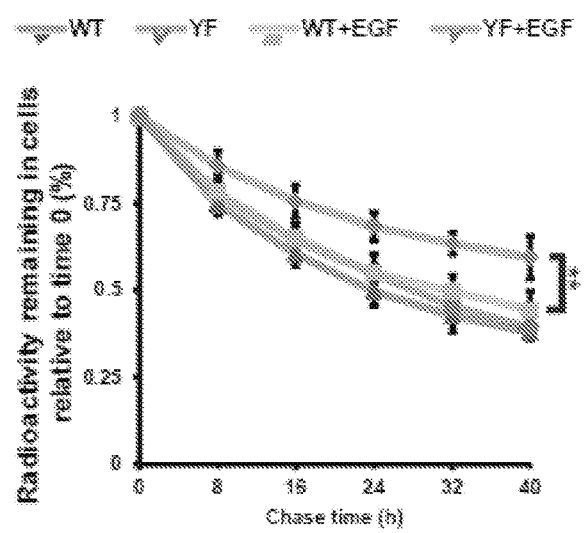
Figure 9:
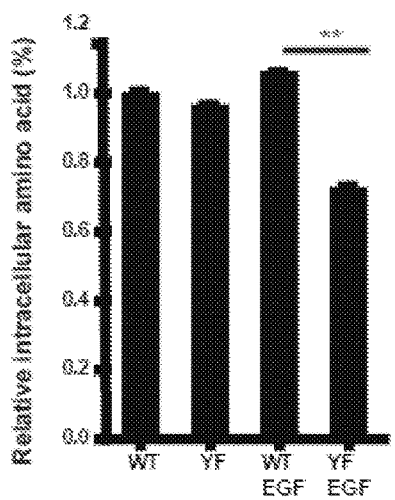
Figure 9:
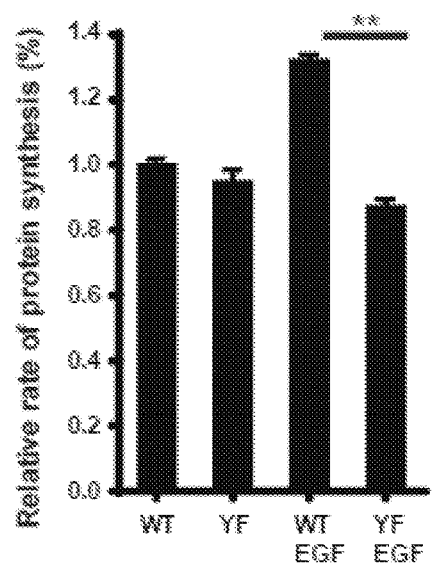
Figure 10:
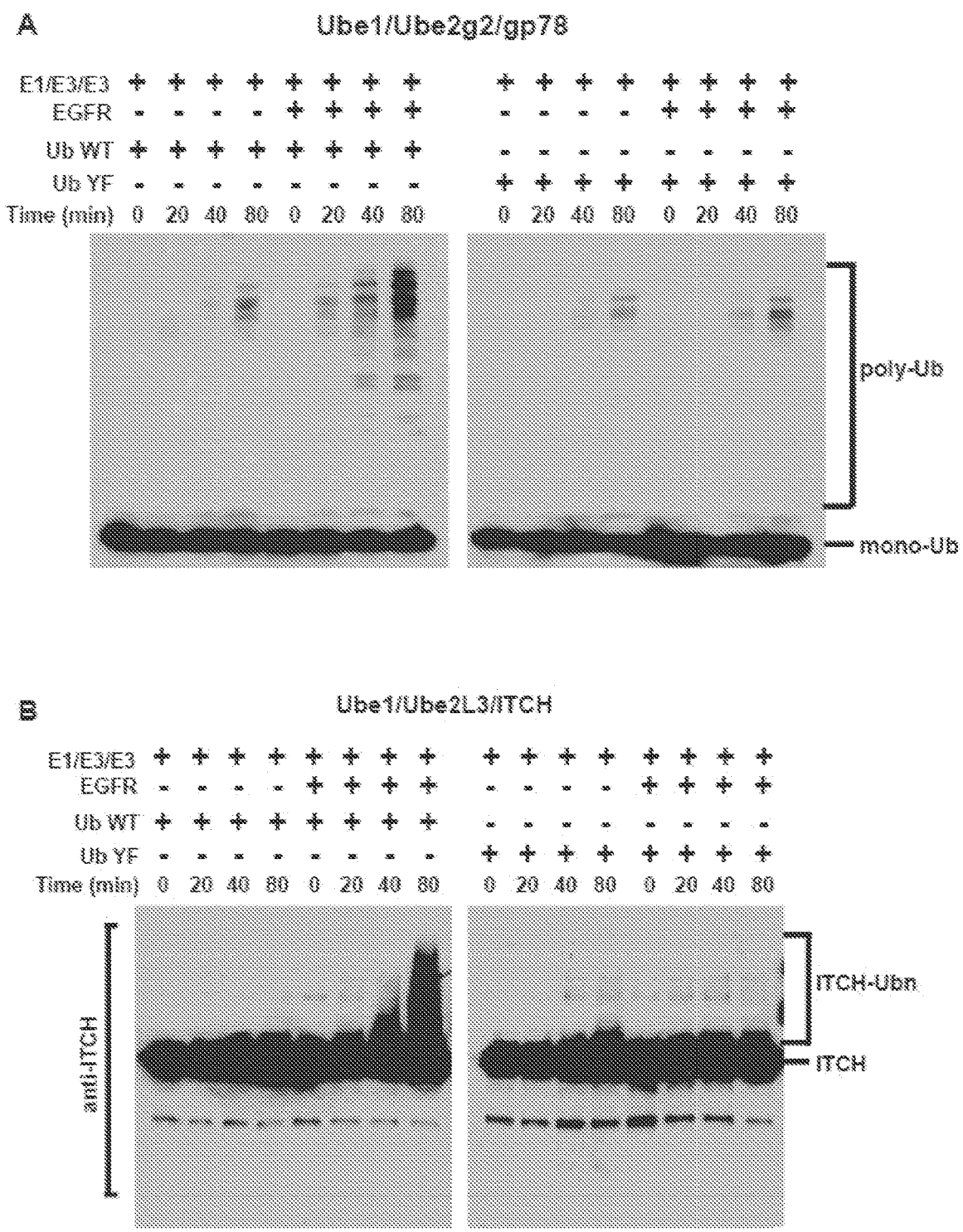
FIG. 10. EGFR promotes ubiquitin chain assembly in vitro. (A). The assembly of ubiquitin chains was determined at 30° C. in the presence of EGFR, Ube1, Ube2g2, gp78, and indicated Ub variants. Samples were taken at the indicated time points, and polyubiquitin chains were detected by immunoblotting with an anti-Ub antibody. (B). The assembly of the ITCH auto-ubiquitin chains was determined at 30° C. in the presence of EGFR, Ube1, UBE2L3, ITCH, and indicated Ub variants. Samples were taken at the indicated time points, and auto-ubiquitination of ITCH was detected by immunoblotting with an anti-ITCH antibody. (C). The assembly of the Diablo linked ubiquitin chains was determined at 30° C. in the presence of EGFR, Ube1, UBE2D2, XIAP, Diablo, and indicated Ub variants. Samples were taken at the indicated time points, and ubiquitin was detected by immunoblotting with an anti-Ub antibody. (D). The assembly of the p53 linked ubiquitin chains was determined at 30° C. in the presence of EGFR, Ube1, UBE2D3, MDM2, p53, and indicated Ub variants. Samples were taken at the indicated time points, and ubiquitin was detected by immunoblotting with an anti-Ub antibody. (E). HSP70/40 were first incubated with Glow Fold protein at 43° C. for 7 minutes. After incubated on ice for 10 minutes, EGFR, Ube1, Ube2d3, CHIP, and indicated Ub variants were added and incubated at 30° C. Samples were taken at the indicated time points, and ubiquitin of Glow Flow protein was detected by immunoblotting with an anti-Glow Fold antibody. (F). The assembly of ubiquitin chains was determined at 30° C. in the presence of Ube1, Ube2D2, cIAP-1, ubiquitin, and substrates (either Tetra-Ub(Ub4) or phosphorylated Tetra-Ub(phos-Ub4)). Samples were taken at the indicated time points, and auto-ubiquitination of cIAP-1 was detected by immunoblotting with an anti-cIAP-1 antibody.
Figure 10:
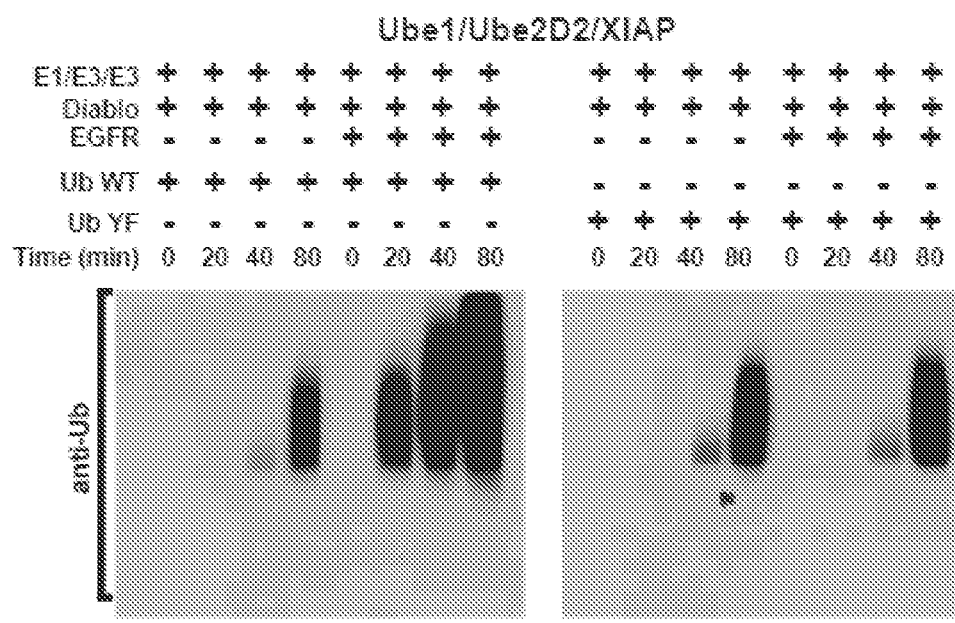
Figure 10:
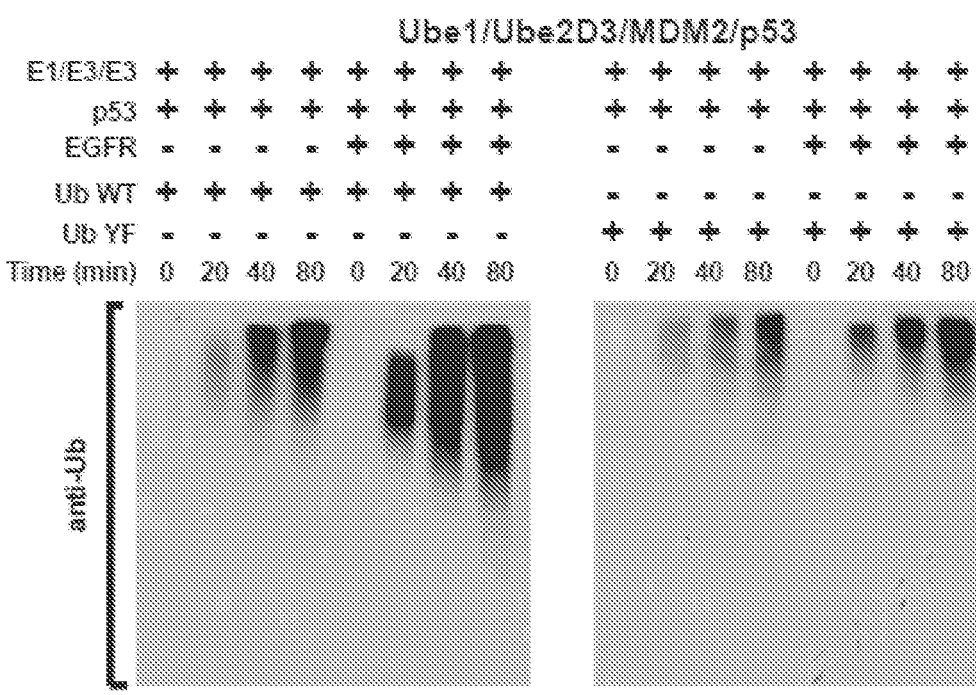
Figure 10:
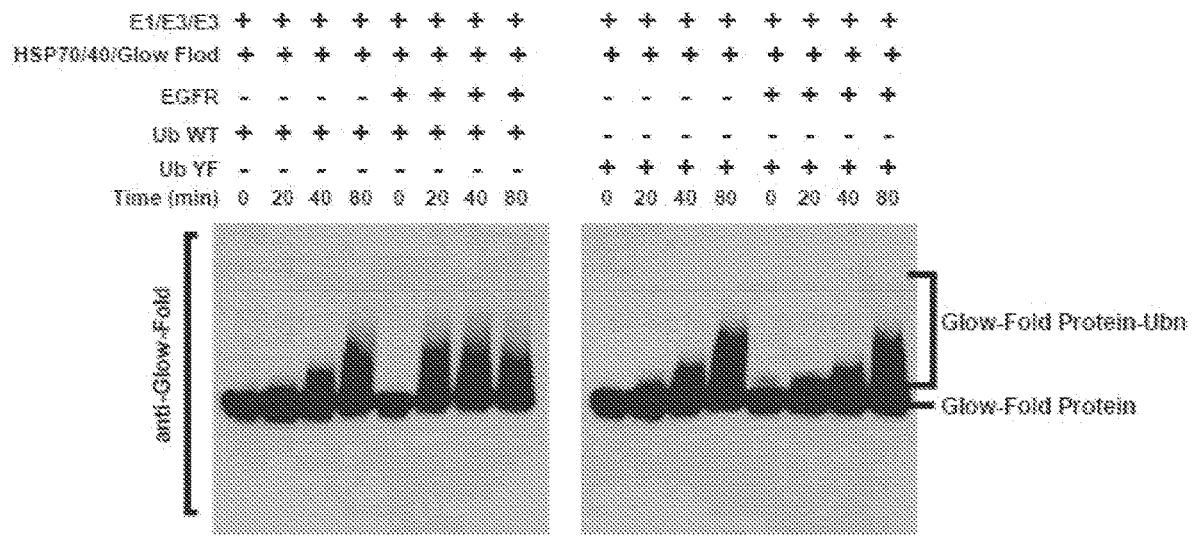
Figure 10:
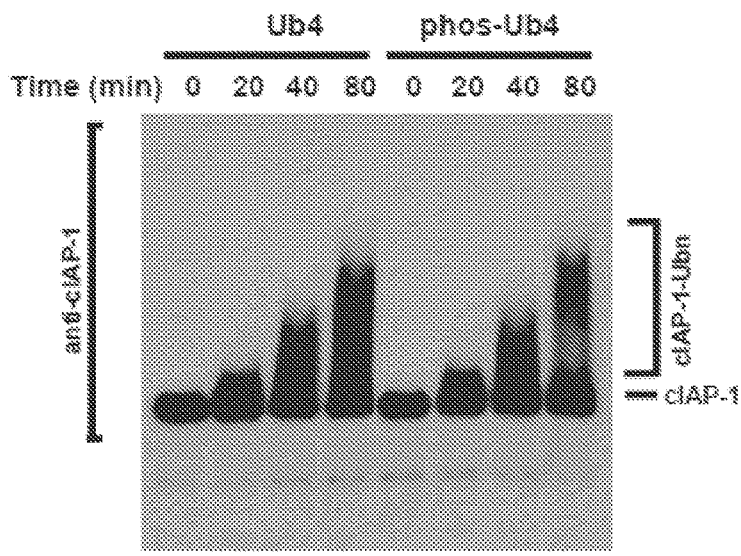

Since EGFR phosphorylated Ub, whether EGFR promotes Ub chain assembly in vitro was tested. The in vitro cIAP auto-ubiquitination system was first used to test the effect of EGFR on Ub chain assembly. A significant increase in Ub chain assembly was observed when EGFR together with WT Ub was included in the in vitro reaction system (FIG. 9A). Notably, EGFR also was highly effective in promoting multiple ubiquitination assays including substrate free K48 ubiquitin chain assembly by Ube2g2/gp78 (FIG. 10A) (Li et al., *Nature*, 446:333-337 (2007)), auto-ubiquitination of ITCH (FIG. 10B), poly-ubiquitination of Diablo catalyzed by XIAP (FIG. 10C), poly-ubiquitination of p53 catalyzed by MDM2 (FIG. 10D), and poly-ubiquitination of Glow-Fold protein by CHIP (FIG. 10E). Mutation of Ub Y59 (Y59F) abolished these increases, indicating that phosphorylation of Ub was essential for EGFR-enhanced ubiquitin chain assembly.

Given that poly-Ub chains were phosphorylated in this experimental system, whether phosphorylated poly-Ub chain could directly activate the E1-E2-E3 system was tested. As shown in FIG. 10F, adding the phosphorylated Ub4 K48 chain in the reaction did not enhance c-IAP auto-ubiquitination, suggesting that phosphorylated Ub4 K48 chain was not an allosteric activator of ubiquitination in this experimental system.

To purify the phos-Ub for further functional study, a Ub auto-phosphorylation system was developed. In this system, FGFR kinase domain was fused to the C-terminal with a His6 tag. The fused protein auto-phosphorylated itself in bacteria. Given there was only one tyrosine site on Ub sequence, only Y59 could be phosphorylated on Ub. After removing the FGFR and His6 tag by USP2cc, free phosphorylated Ub was obtained. Phos-tag gel analysis indicated that ubiquitin purified with this construct was completely phosphorylated. With the purified phosUb, an in vitro ubiquitin assay was performed. Phos-Ub was found to dramatically promote Ub chain assembly in different in vitro ubiquitination systems (FIG. 9B and FIGS. 1C-F). E2 charging assay with different E2s indicated that phos-Ub did not affect E1-mediated charging of E2 enzymes (FIG. 1G). Using a di-Ub synthesis assay that produces K48-linked conjugates, phos-Ub was found to promote the receptor Ub function rather than affecting the donor Ub activity (FIG. 9C). These results established that phos-Ub specifically enhanced the receptor Ub function, enabling E2 to build Ub chain in vitro.

Figure 11:
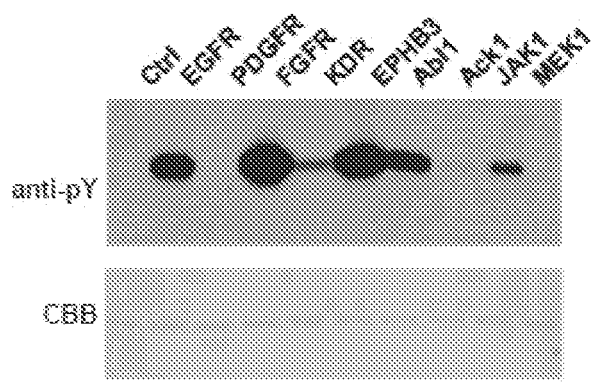
FIG. 11. FGFR2 phosphorylates ubiquitin and promote ubiquitination. (A) An in vitro kinase assay was performed at 30° C. in the presence of K48 tetra-Ub chain and different tyrosine kinases. The reactions were stopped by adding 2× loading buffer and separated on an SDS-PAGE gel. The gels were subjected to western blot with anti-phosphor-tyrosine antibody (upper panel) or Coomassie brilliant blue (CBB) staining (lower panel). (B). NIH-3T3 cells were serum starved for 48 hours and then incubated in medium containing 20 ng/mL FGFb for different time course. Cell lysates were blotted with an anti-pY59 and anti-actin antibody. (C). NIH-3T3 cells were serum starved for 48 hours and then incubated in medium containing vehicle, FGFb, or FGFb and TKI-258. Cell lysates were blotted with an anti-pY59 antibody. (D). HEK293 cells were transfected with empty vector (Ctrl), FGFR2 wide type, or FGFR2 KR. Cell lysates were blotted with an anti-pY59 antibody. (E). The assembly of the Ube2g2-linked ubiquitin chains was determined at 30° C. in the presence of FGFR2, Ube1, Ube2g2, gp78, and indicated Ub variants. Samples were taken at the indicated time points, and polyubiquitin chains were detected by immunoblotting with an anti-Ub antibody.
Figure 11:
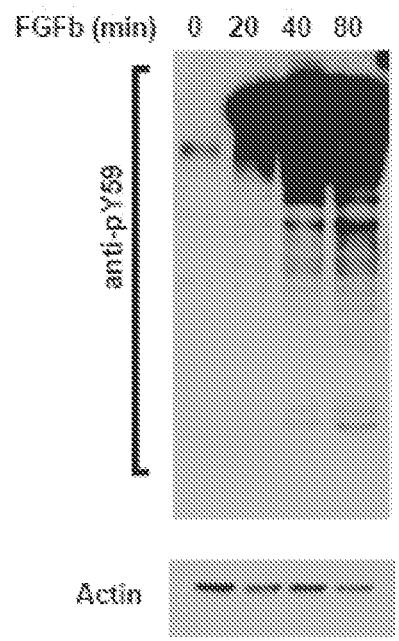
Figure 11:
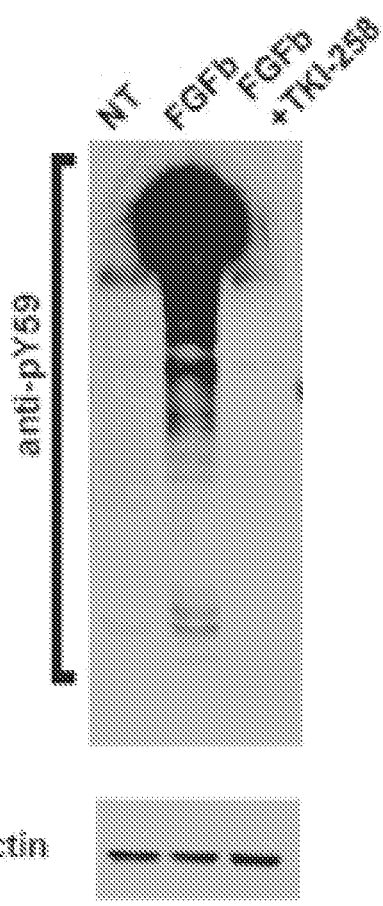
Figure 11:
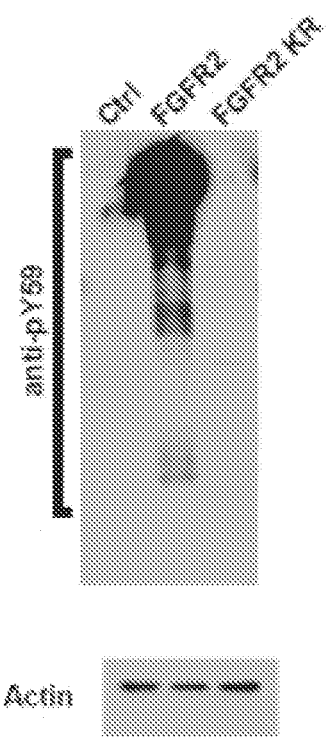
Figure 11:
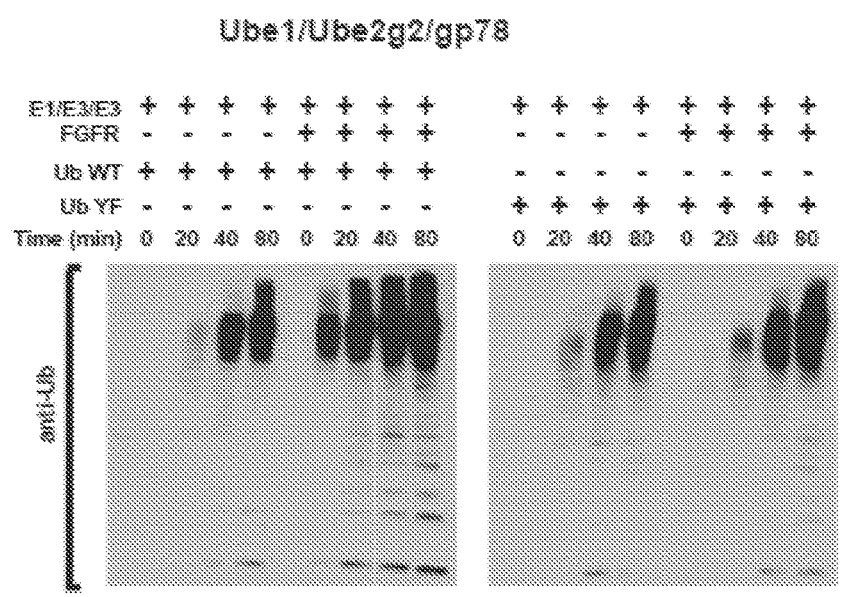
Figure 12:
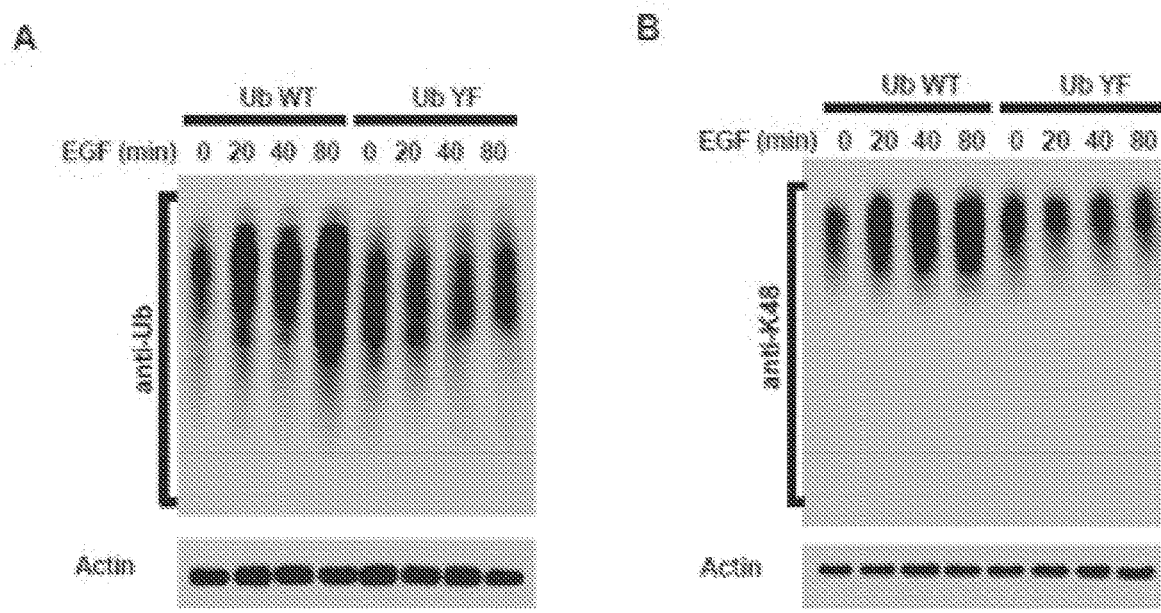
FIG. 12. Phosphorylation of Ub promotes Ub chain assembly. (A to B). Western blot images representative of the three independent experiments quantified in FIG. 9D (A)
Figure 12:
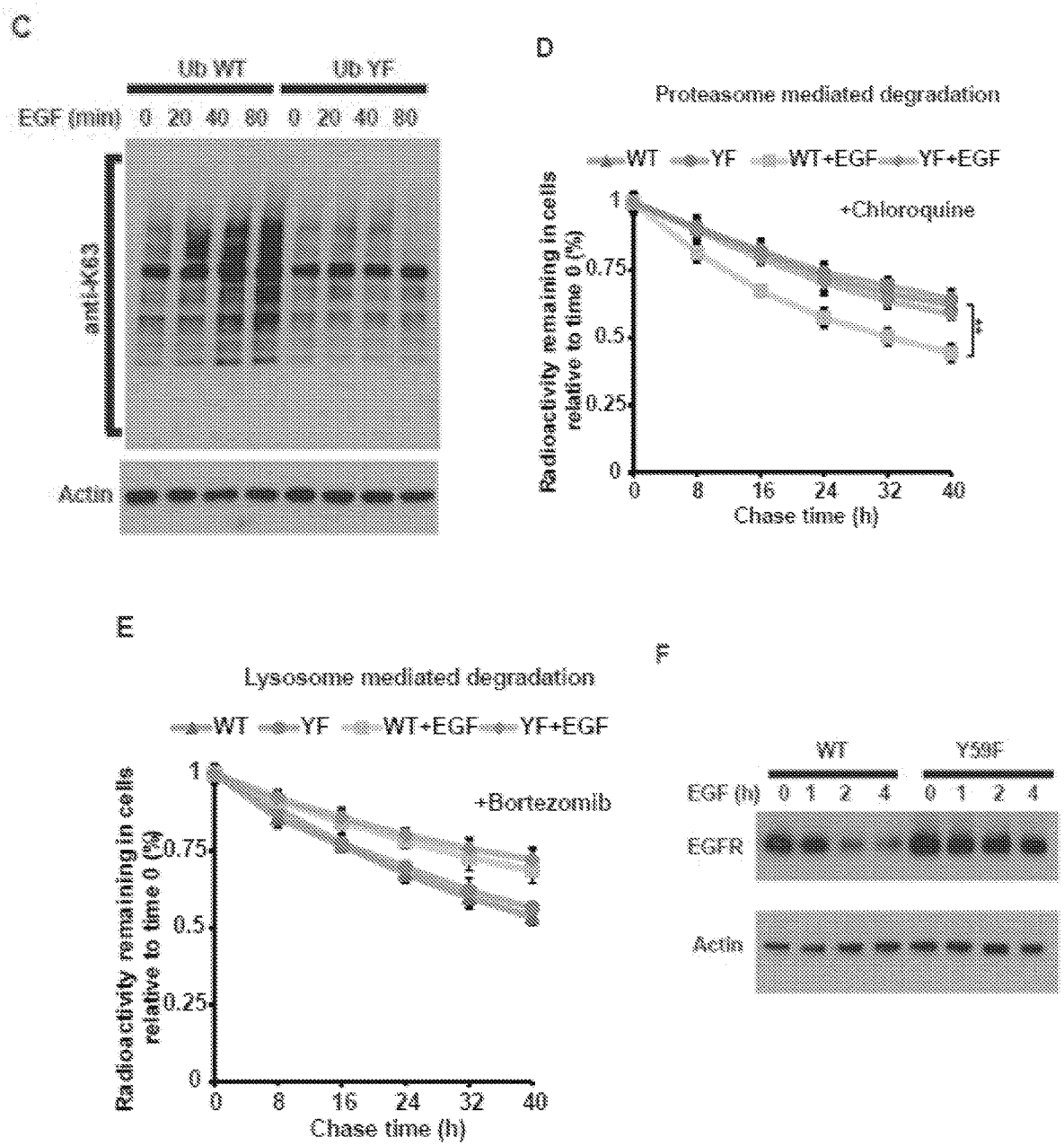
Figure 12:
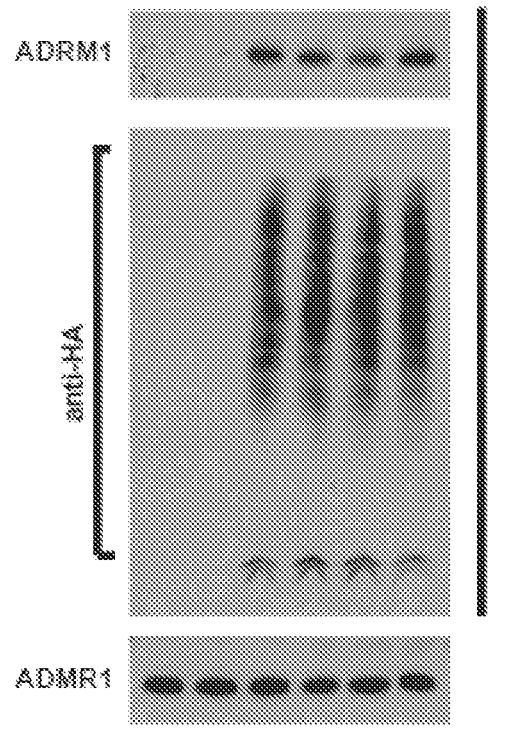

Since EGFR phosphorylates Ub and thus regulates Ub chain assembly, whether other tyrosine kinases could phosphorylate Ub chains was tested. As shown in FIG. 11A, multiple tyrosine kinases phosphorylated Ub4 in vitro, suggesting that Ub chain might be a common substrate for tyrosine kinases. Activation of FGFR increased Ub phosphorylation in NIH-3T3 cells (FIGS. 11B-D). FGFR also promoted Ub chain assembly by Ube2g2/gp78 in vitro (FIG. 11E). These results indicate that FGFR also phosphorylated ubiquitin to promote poly-ubiquitination.

Next, the Ub replacement cells were utilized to test the role of Ub phosphorylation directly in cells. After EGF treatment, total ubiquitin conjugates as well as K48-linked conjugates increased by about 1.5 to 2 fold in cells expressing WT Ub, but not in those expressing Ub Y59F (FIGS. 9D-E and FIGS. 12A-C). Notably, the levels of Ub WT and Ub Y59F proteins after DOX induction for 3 days in the absence of serum was comparable, suggesting the Y59F mutation did not affect basal Ub function. Collectively, these results demonstrate that phosphorylation of Ub promotes K48-linked Ub chain formation.

To further study the function of Ub phosphorylation in cells, the Ub replacement cells were used to assess the role of the Ub phosphorylation on protein degradation. After treatment with EGF, the protein degradation rate was much higher in cells expressing Ub WT than those expressing Ub Y59F mutant (FIG. 9F). To clarify the effect of Ub phosphorylation on UPS and autophagy system, bortezomib or chloroquine were added in the chase media. While EGF treatment accelerated proteasomal degradation in cells expressing Ub WT, it had no significant effect in cells expressing the Ub Y59F mutant (FIG. 12D), indicating that Ub phosphorylation mediated EGF induced proteasomal protein degradation. Ub phosphorylation had no significant effects on global lysosome-mediated degradation (FIG.

12E). Notably, Ub phosphorylation affected EGFR degradation (FIG. 12F), which was probably mediated by proteasomal degradation (Ettenberg et al., *J. Biol. Chem.*, 276: 27677-27684 (2001); and Longva et al., *J. Cell Biol.*, 156:843-854 (2002)). Phosphorylation of Ub did not affect the interaction between Ub chain and proteasomal receptor ADMR1 (FIG. 12G), demonstrating that phos-Ub induced proteasomal degradation might largely depend on the enhancement of Ub chain assembly.

Given that protein degradation contributes an important fraction of the supply of amino acids (Suraweera et al., *Mol. Cell*, 48:242-253 (2012)), it was hypothesized that the enhanced proteasomal degradation upon EGFR activation could serve to maintain adequate pools of amino acids to sustain new protein synthesis. The effect of ubiquitin phosphorylation on amino acid level and protein synthesis rate were assessed. Cells expressing the Ub Y59F mutant, compared to cells expressing Ub WT, exhibited significant decreased intracellular amino acid (FIG. 9G) levels as well as protein synthesis rates (FIG. 9H) after treatment with EGF, indicating the importance of Ub phosphorylation for amino acid and protein homeostasis in the context of EGFR activation.

Figure 13:
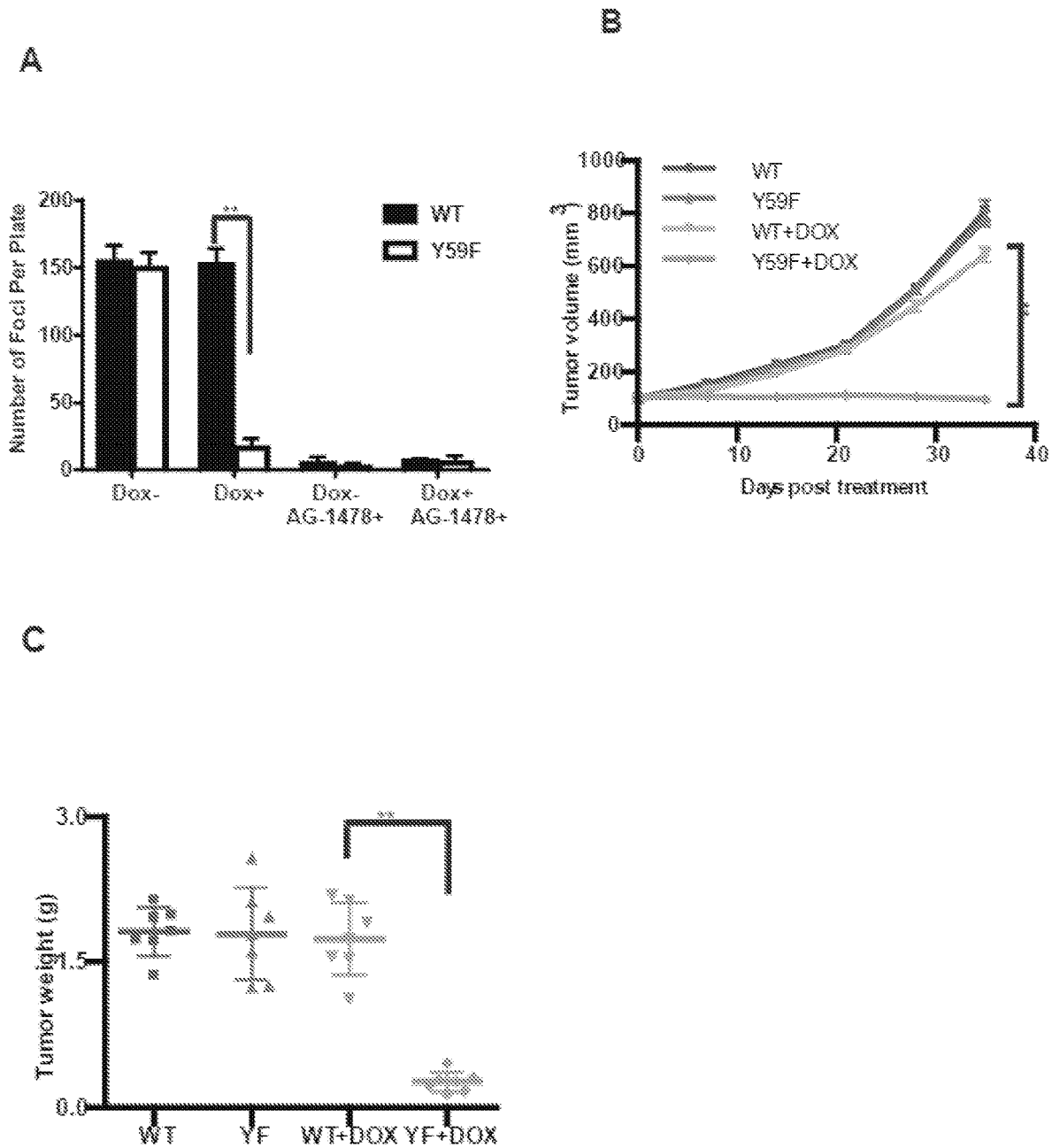
FIG. 13. Phosphorylation of ubiquitin is required for tumor growth and is upregulated in human breast cancer. (A). Soft agar colony-formation assay was performed using WT Ub- and Ub Y59F-replacement cells. Cells were plated in 0.3% top agarose in 35 mm dishes with or without DOX and AG-1478. Colonies were counted two weeks later. Data were mean±SD of three independent experiments. (: p<0.01, Student's t-test). (B). $5 \times 10^6$ WT Ub- and Ub Y59F-replacement cells were subcutaneously injected into nude mice. After the tumor size reached 100 mm$^3$, vehicle or doxycycline was administered in drinking water. Tumor growth was measured at the indicated times after doxycycline treatment. n=6 for each group. (p<0.01, by two-way ANOVA). (C). Tumor weight of mice with subcutaneous injection as (B) at day 35 after doxycycline treatment. **p<0.01, by two-way ANOVA. (D). Immunohistochemical staining of pY59 and K48-linked Ub conjugates in representative normal breast and breast carcinoma specimens on the TMAs. Brown staining indicated positive immunoreactivity. (E and F). pY59 (E) and K48-linked Ub conjugates (F) status in normal breast (n=40) and breast carcinoma (n=40) specimens. Statistical significance in (E) and (F) was determined by $\chi^2$ test. (G). Correlation between pY59 and K48-linked Ub conjugates levels in human breast tumors (n=77). R: correlation coefficient.
Figure 13:
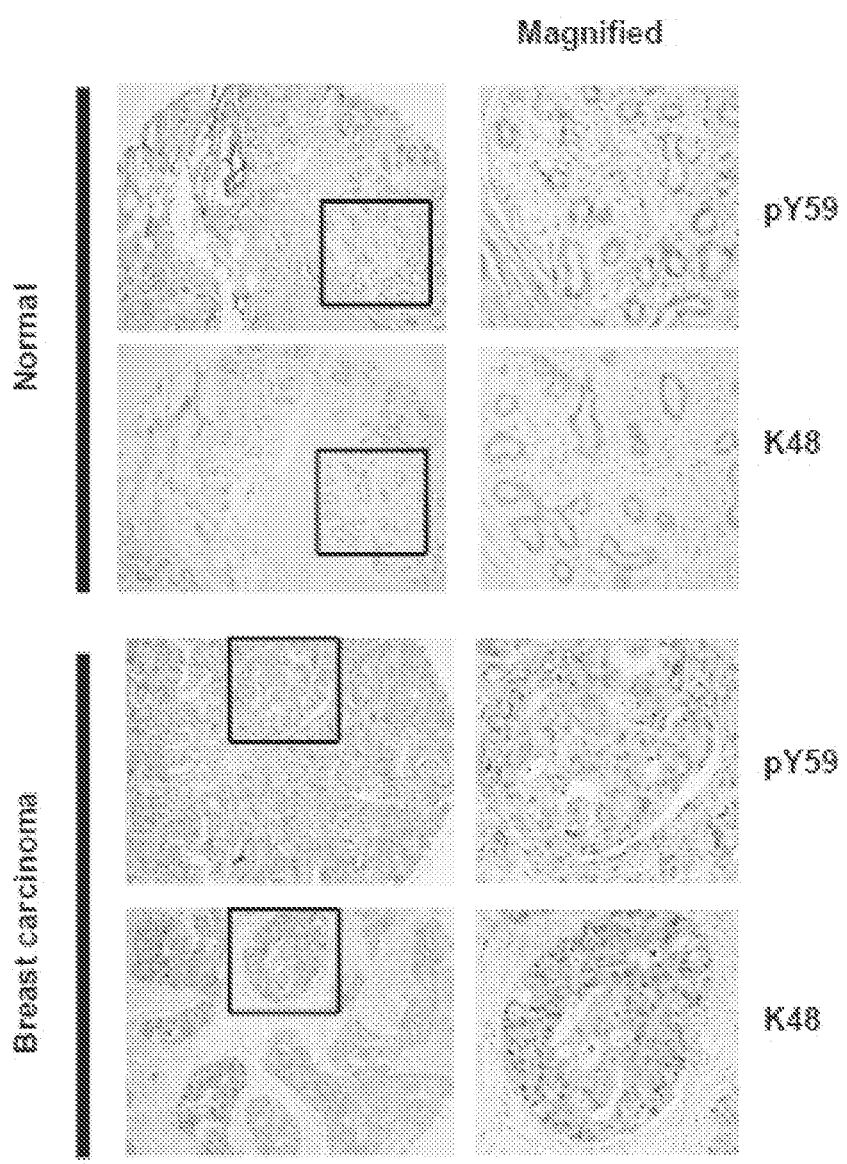
Figure 13:
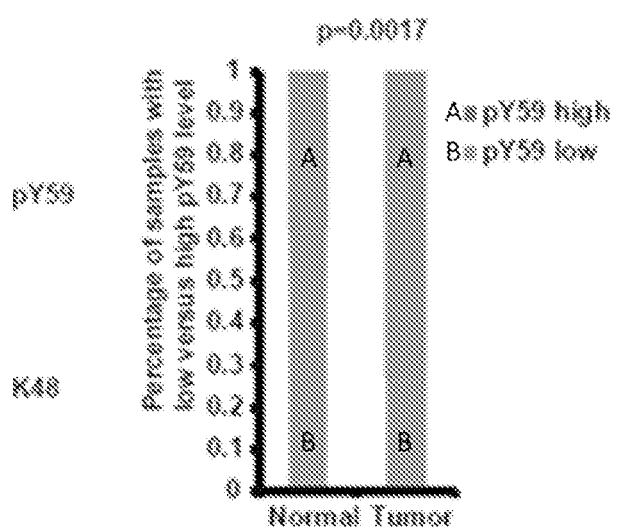
Figure 13:
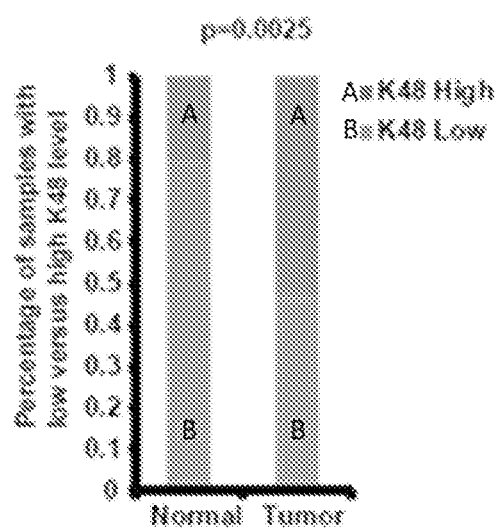
Figure 13:
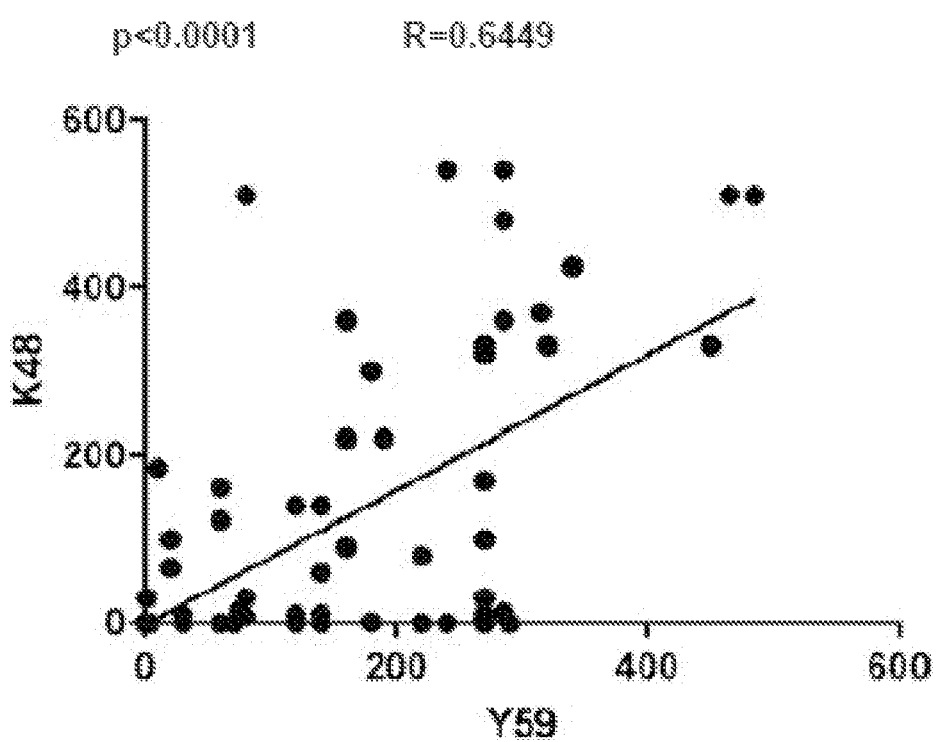

Given that EGFR promotes tumor cell growth, whether the phosphorylation of Ub regulated tumor cell growth was studied. As shown in FIG. 13A, after Ub replacement cells were treated with DOX, the growth of Y59F cells was dramatically inhibited compared to wild type cells. To investigate the biological function of Ub phosphorylation in vivo, Ub replacement cells were subcutaneously implanted into nude mice. After the tumor reached 100 mm$^3$, DOX was added in drinking water to induce ubiquitin replacement. Tumor growth was then monitored for five weeks. Mice bearing Ub YF expressing cells exhibited decreased tumor growth throughout the experiment compared to mice implanted with Ub WT expressing cells (FIG. 13B). At 35 days after DOX induction, a significant decrease (around 90%) in the weight of the tumors formed by cells expressing Ub YF was observed (FIG. 13C). Notably, without DOX induction, the tumor growth between Ub WT and YF expressing cells was almost the same (FIGS. 13A-B). These results demonstrate that Y59 phosphorylation is important for tumor growth in vivo.

Figure 14:
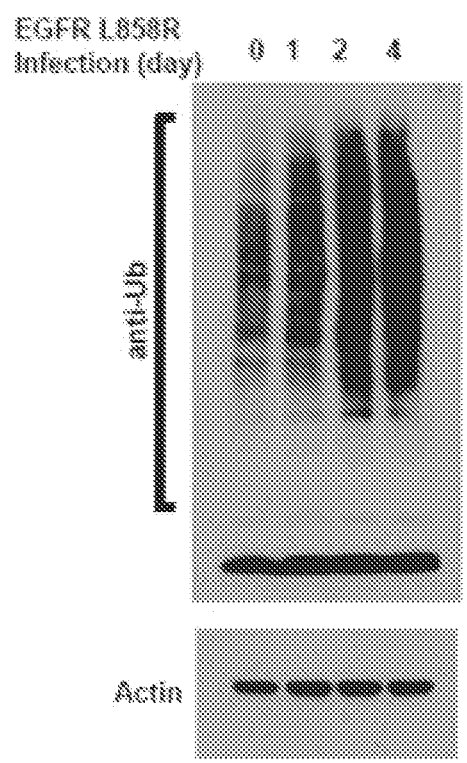
FIG. 14. NIH-3T3 transformed by EGFR L858R mutant shows enhanced cellular ubiquitin conjugates and proteasomal degradation. (A-D). NIH-3T3 cells were infected with virus expressing EGFR DM mutant. Cells were harvested at different times after infection. Total Ub conjugates (A), K48-linked conjugates (B), and K63-linked conjugates (C) were determined by Western blot, and their intensities were quantitated and normalized to that of β-actin. Data were mean±SD of three independent experiments. (: p<0.01, Student's t-test). (E) NIH-3T3 cells were infected with virus expressing EGFR DM mutant. Cells were harvested at different times after infection. Cell lysates were blotted with an anti-pY59 antibody. (F). NIH-3T3 stably expressing empty vector (Ctrl) or EGFR L858R mutant were serum starved for 48 hours and were labeled with $^{35}$S Met for 24 hours in the absence of serum. After switching to chase medium for 4 hours to allow the degradation of short-lived components, fresh chase medium containing vehicle or EGF was added in the presence of 10 µM chloroquine. At different time points, cells were harvested, and radiolabeled protein remaining in the cell was measured. The rate of protein degradation was shown as the fraction of radiolabeled protein remaining over time. Data were mean±SD of three independent experiments. (: p<0.01, two-way ANOVA test). (G) NIH-3T3 cells transformed by EGFR L858R, and Ctrl cells were plated in 96 well plate with 500 cell per well. Cells were treated with different doses of bortezomib for 48 hours and proceeded to MTS assay. Data were mean±SD of three independent experiments. (**: p<0.01, two-way ANOVA test).
Figure 14:
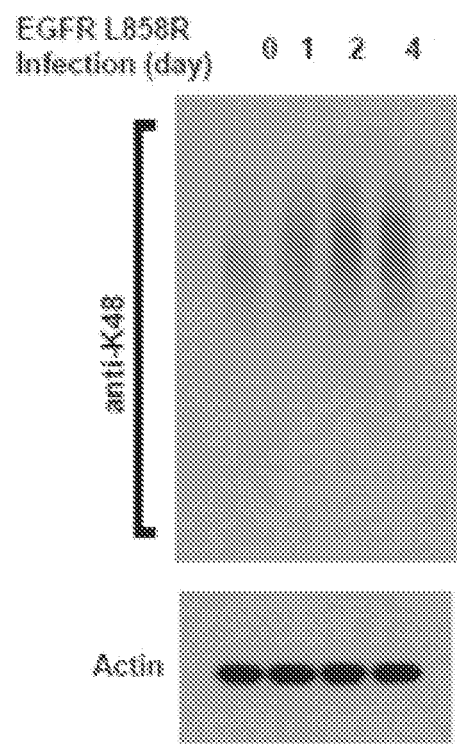
Figure 14:
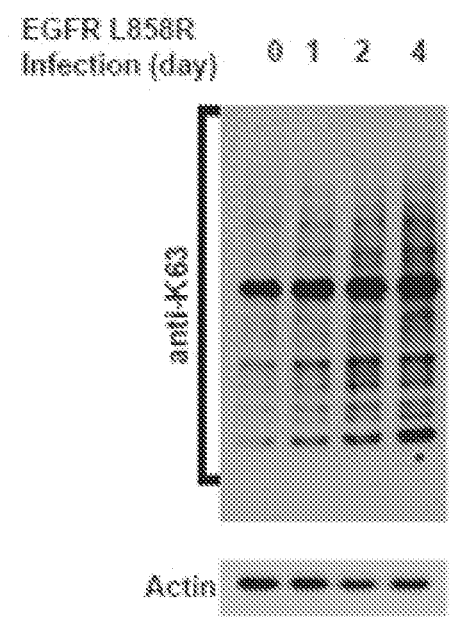
Figure 14:
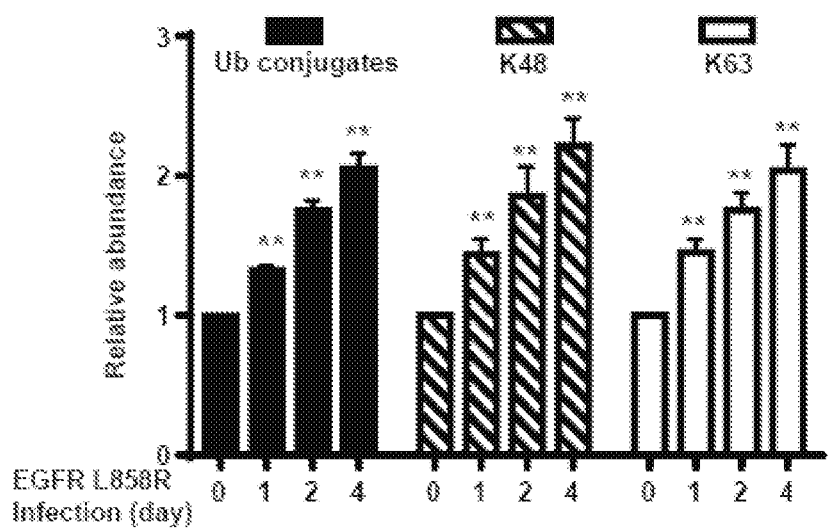
Figure 14:
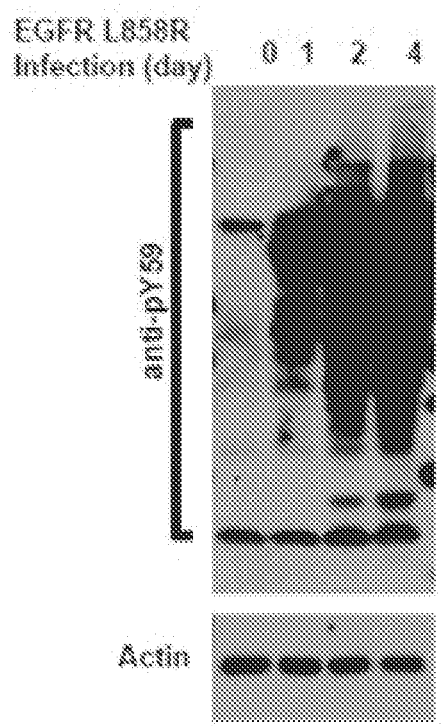
Figure 14:
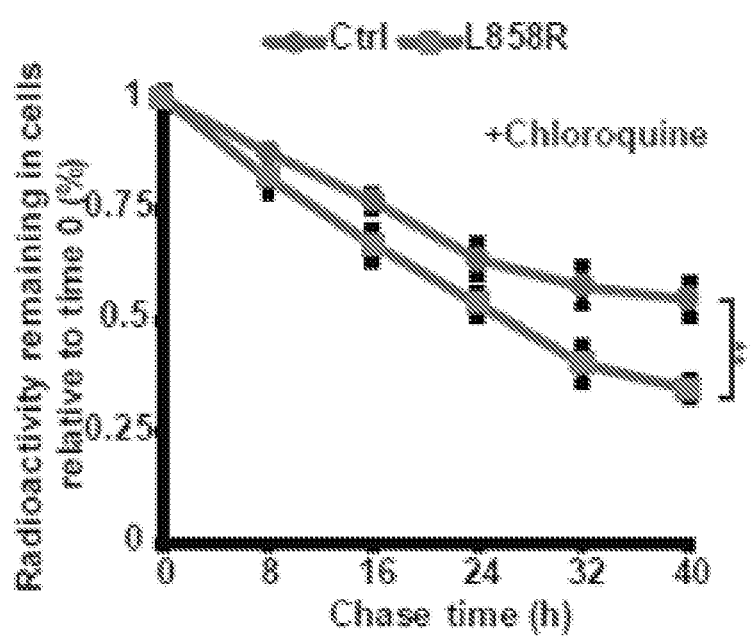
Figure 14:
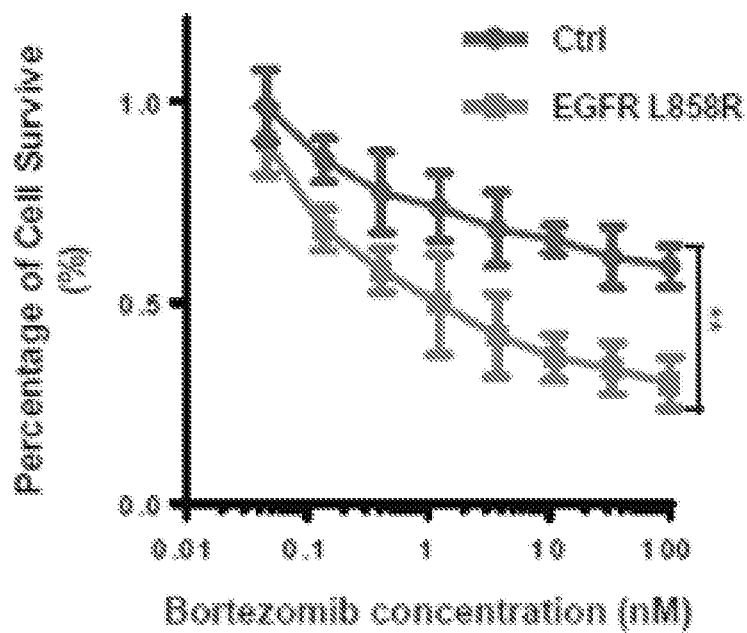

EGFR is involved in the pathogenesis and progression of different carcinoma types. To determine the relevance of regulation of Ub chain formation by phosphorylation during EGFR oncogenic pathway, NIH-3T3 cells were transformed with constitutively active EGFR mutant L858R. After infection with virus expressing EGFR L858R, the ubiquitin and K48-linked conjugates increased dramatically (FIGS. 14A-D), together with the level of phosphorylation of Ub Y59 (FIG. 14E). Proteasomal degradation also increased in transformed cells compared to control cells (FIG. 14F). Furthermore, transformed cells exhibited much higher bortezomib sensitivity (FIG. 14G). These results indicated that during EGFR mediated transformation, phosphorylation of Ub can promote K48-linked Ub chain assembly, facilitating the high proteasomal activity in tumor cells, which is important for the maintenance of the transformed phenotype (Pray et al., *Drug Resist. Updat.*, 5:249-258 (2002); and Voorhees et al., *Clin. Cancer Res.*, 9:6316-6325 (2003)).

To determine the relevance of regulation of Ub chain formation by phosphorylation in patients, immunohistochemical staining of pY59 and K48-linked Ub conjugates was performed using breast cancer progression tissue microarrays from Biomax Inc., with antibodies validated for immunohistochemistry. Notably, upregulation of pY59 and K48 was observed in 52.5% (21 of 40) and 30% (12 of 40) of breast tumors, whereas only 7.5% (5 of 40) and 2.5% (1 of 40) of normal mammary tissues exhibited high expression of pY59 and K48 (FIGS. 13D-F), respectively, suggesting that both pY59 and K48 were upregulated in human breast tumors. Moreover, a significant positive correlation (R=0.6449, $P<1\times10^{-4}$) between pY59 and K48 protein levels was observed in these breast carcinomas (FIG. 13G). These results demonstrate that high pY59 may contribute to high K48-linked chains in a substantial fraction of human tumors and might contribute to tumor initiation or progression.

Collectively, the results provided herein demonstrate that EGFR can phosphorylate poly-Ub to stimulate Ub chain assembly and subsequently increase cellular protein degradation, which can provide essential amino acids for cell growth. This mechanism can also be shared by FGFR and other pro-proliferative receptor tyrosine kinases.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer, wherein said method comprises:
   (a) identifying a mammal as having cancer cells comprising an elevated level of Y59 phosphorylated Ub polypeptides, and
   (b) administering a tyrosine kinase inhibitor to said mammal, thereby reducing the number of said cancer cells within said mammal, wherein said tyrosine kinase inhibitor is an epidermal growth factor receptor (EGFR) inhibitor or is a fibroblast growth factor receptor (FGFR) inhibitor.

2. The method of claim 1, wherein said mammal is a human.

3. The method of claim 1, wherein said cancer is breast cancer.

4. The method of claim 1, wherein said tyrosine kinase inhibitor is said EGFR inhibitor.

5. The method of claim 4, wherein said EGFR inhibitor is PD153035 HCl, PD168393, Erlotinib, AZD3759, Cetuximab, AZD9291, Gefinitib, Panitumumab, ZD1839, Afatinib, Tyrphostin (AG-1478), Lapatinib, Rociletinib (CO-1686), or Neratinib.

6. The method of claim 1, wherein said tyrosine kinase inhibitor is said FGFR inhibitor.

7. The method of claim 6, wherein said FGFR inhibitor is Infigratinib (BGJ398), BLU9931, AZD4547, FGF401, Debio-1347, JNJ-42756493, TAS 120, FIIN-2, LY2874455, Derazantinib ARQ 087, or BAY 1163877.

8. A method for treating cancer, wherein said method comprises administering a tyrosine kinase inhibitor to a mammal identified as having cancer cells comprising an elevated level of Y59 phosphorylated Ub polypeptides, thereby reducing the number of said cancer cells within said mammal, wherein said tyrosine kinase inhibitor is an epidermal growth factor receptor (EGFR) inhibitor or is a fibroblast growth factor receptor (FGFR) inhibitor.

9. The method of claim 8, wherein said mammal is a human.

10. The method of claim 8, wherein said cancer is breast cancer.

11. The method of claim 8, wherein said tyrosine kinase inhibitor is said EGFR inhibitor.

12. The method of claim 11, wherein said EGFR inhibitor is PD153035 HCl, PD168393, Erlotinib, AZD3759, Cetuximab, AZD9291, Gefinitib, Panitumumab, ZD1839, Afatinib, Tyrphostin (AG-1478), Lapatinib, Rociletinib (CO-1686), or Neratinib.

13. The method of claim 8, wherein said tyrosine kinase inhibitor is said FGFR inhibitor.

14. The method of claim 13, wherein said FGFR inhibitor is Infigratinib (BGJ398), BLU9931, AZD4547, FGF401, Debio-1347, JNJ-42756493, TAS 120, FIIN-2, LY2874455, Derazantinib ARQ 087, or BAY 1163877.

* * * * *